(12) United States Patent
Temkin et al.

(10) Patent No.: US 11,177,027 B2
(45) Date of Patent: Nov. 16, 2021

(54) SYSTEMS AND METHODS FOR DATA PROCESSING AND PERFORMING STRUCTURED AND CONFIGURABLE DATA COMPRESSION

(71) Applicant: Pleiotek, Bethesda, MD (US)

(72) Inventors: Joshua Michael Temkin, Bethesda, MD (US); Melissa Greenfield Temkin, Bethesda, MD (US); Johna Noelle Morris, Silver Spring, MD (US); Eric Wesley Herring, Bluemont, VA (US)

(73) Assignee: Pleiotek, Bethesda, MD (US)

( * ) Notice: Subject to any disclaimer, the term of this patent is extended or adjusted under 35 U.S.C. 154(b) by 0 days.

(21) Appl. No.: 17/316,784

(22) Filed: May 11, 2021

(65) Prior Publication Data
US 2021/0327549 A1 Oct. 21, 2021

Related U.S. Application Data

(63) Continuation-in-part of application No. 17/034,312, filed on Sep. 28, 2020, now Pat. No. 11,013,639.
(Continued)

(51) Int. Cl.
*G16H 10/60* (2018.01)
*H04W 4/80* (2018.01)
(Continued)

(52) U.S. Cl.
CPC .......... *G16H 10/60* (2018.01); *G06F 16/288* (2019.01); *H04W 4/80* (2018.02); *H04W 28/06* (2013.01)

(58) Field of Classification Search
CPC ................................ H04Q 4/80; H04Q 28/06
See application file for complete search history.

(56) References Cited

U.S. PATENT DOCUMENTS 8,190,089 B2   5/2012  Heo
8,552,730 B2  10/2013  Chiao et al.
(Continued)

FOREIGN PATENT DOCUMENTS

EP    2836269 B1    8/2019
EP    2081488 B1    5/2020
(Continued)

OTHER PUBLICATIONS

International Search Report, dated Jan. 13, 2021, from corresponding International Application No. PCT/US2020/061757.
(Continued)

*Primary Examiner* — Robert A Sorey
(74) *Attorney, Agent, or Firm* — Brient IP Law, LLC

(57) ABSTRACT

A wearable data storage and transmission device and related systems that collect and store sensor data from sensors worn by a user. The device components can include a processor, battery, data storage media, NFC components, Bluetooth components, Wi-Fi components, and wired communications components. The device can remain powered down, powering up periodically to collect sensor data using low energy methods and/or in response to receiving a signal (e.g., NFC, power, Bluetooth, etc.) from an external device that causes the device to power up its components and make sensor data available to the external device. The collected sensor data may be encoded, compressed, stored, and/or exchanged in one or more structured records using various methods to improve the information storage capabilities of the device, including using the disclosed QR coding methods.

20 Claims, 13 Drawing Sheets

Related U.S. Application Data which is a continuation-in-part of application No. 16/882,837, filed on May 26, 2020, now Pat. No. 10,786,395, application No. 17/316,784, which is a continuation-in-part of application No. 16/882,836, filed on May 26, 2020, now Pat. No. 11,011,258.

(60) Provisional application No. 62/978,353, filed on Feb. 19, 2020, provisional application No. 62/978,350, filed on Feb. 19, 2020.

(51) Int. Cl.
*H04W 28/06* (2009.01)
*G06F 16/28* (2019.01)

(56) References Cited

U.S. PATENT DOCUMENTS

| | | | |
|---|---|---|---|
| 8,861,733 | B2 | 10/2014 | Benteo et al. |
| 9,136,980 | B2 | 9/2015 | Baheti |
| 9,451,340 | B2 | 9/2016 | Duesterhoft et al. |
| 9,455,768 | B2 | 9/2016 | Griffin et al. |
| 9,633,097 | B2 | 4/2017 | Tidwell et al. |
| 9,778,131 | B2 | 10/2017 | Everett et al. |
| 10,022,613 | B2 | 7/2018 | Tran et al. |
| 10,240,557 | B2 | 3/2019 | Boczek et al. |
| 10,265,219 | B2 | 4/2019 | Duesterhoft et al. |
| 10,366,315 | B1* | 7/2019 | Kumar ............ G06K 19/06131 |
| 10,652,504 | B2 | 5/2020 | Shibaev et al. |
| 10,659,586 | B2 | 5/2020 | Cheng et al. |
| 10,666,325 | B2 | 5/2020 | Zhou et al. |
| 10,786,395 | B1 | 9/2020 | Temkin et al. |
| 10,847,268 | B1* | 11/2020 | Burnett ................ G16H 40/20 |
| 2003/0023580 | A1 | 1/2003 | Braud et al. |
| 2006/0252372 | A1 | 11/2006 | Liu et al. |
| 2009/0033469 | A1 | 2/2009 | Seppae |
| 2010/0053208 | A1* | 3/2010 | Menningen ............ G06T 19/00 345/619 |
| 2011/0237230 | A1 | 9/2011 | Li |
| 2013/0053659 | A1 | 2/2013 | Melchert et al. |
| 2014/0100879 | A1 | 4/2014 | Kharebov et al. |
| 2015/0297437 | A1 | 10/2015 | Neuenhahn et al. |
| 2016/0156603 | A1 | 6/2016 | Janik |
| 2016/0353270 | A1 | 12/2016 | Brisebois |
| 2017/0265800 | A1 | 9/2017 | Auchinleck |
| 2017/0347940 | A1 | 12/2017 | Carr |
| 2017/0348156 | A1 | 12/2017 | Duesterhoft et al. |
| 2018/0296836 | A1 | 10/2018 | Creasey et al. |
| 2018/0350180 | A1* | 12/2018 | Onischuk ............... G07C 13/00 |
| 2019/0046813 | A1* | 2/2019 | Zhou ..................... G16H 50/70 |
| 2019/0087554 | A1 | 3/2019 | Fish et al. |
| 2019/0108907 | A1* | 4/2019 | Kadri ..................... G16H 80/00 |
| 2019/0114619 | A1 | 4/2019 | Wilson |
| 2019/0147452 | A1 | 5/2019 | Leung |
| 2019/0183426 | A1 | 6/2019 | Paquet et al. |
| 2019/0209022 | A1 | 7/2019 | Sobol et al. |
| 2019/0328327 | A1 | 10/2019 | Kim et al. |
| 2019/0349652 | A1 | 11/2019 | Greenewald et al. |
| 2019/0365571 | A1 | 12/2019 | O'Mahony et al. |
| 2020/0121245 | A1 | 4/2020 | Barclay et al. |
| 2020/0188161 | A1 | 6/2020 | Seres et al. |
| 2020/0381094 | A1 | 12/2020 | Ryan et al. |

FOREIGN PATENT DOCUMENTS

| | | |
|---|---|---|
| EP | 3449882 B1 | 9/2020 |
| WO | 2015168720 A1 | 11/2015 |

OTHER PUBLICATIONS

Notice of Allowance, dated Aug. 12, 2020, from corresponding U.S. Appl. No. 16/882,837.
Notice of Allowance, dated Feb. 3, 2021, from corresponding U.S. Appl. No. 16/882,836.
Office Action, dated Dec. 31, 2020, from corresponding U.S. Appl. No. 17/034,312.
Office Action, dated Jul. 9, 2020, from corresponding U.S. Appl. No. 16/882,837.
Office Action, dated Oct. 29, 2020, from corresponding U.S. Appl. No. 16/882,836.
Restriction Requirement, dated Jul. 16, 2020, from corresponding U.S. Appl. No. 16/882,836.
Written Opinion of the International Searching Authority, dated Jan. 13, 2021, from corresponding International Application No. PCT/US2020/061757.
Notice of Allowance, dated Apr. 13, 2021, from corresponding U.S. Appl. No. 17/034,312.
Office Action, dated Sep. 27, 2021, from corresponding U.S. Appl. No. 17/316,786.

* cited by examiner

SYSTEMS AND METHODS FOR DATA PROCESSING AND PERFORMING STRUCTURED AND CONFIGURABLE DATA COMPRESSION

CROSS-REFERENCE TO RELATED APPLICATIONS

This application is a continuation-in-part of U.S. patent application Ser. No. 16/882,836, filed May 26, 2020, which claims priority to U.S. Provisional Patent Application Ser. No. 62/978,350, filed Feb. 19, 2020, and to U.S. Provisional Patent Application Ser. No. 62/978,353, filed Feb. 19, 2020. This application is also a continuation-in-part of U.S. patent application Ser. No. 17/034,312, filed Sep. 28, 2020, which is a continuation-in-part of U.S. patent application Ser. No. 16/882,837, filed May 26, 2020, now U.S. Pat. No. 10,786,395, issued Sep. 29, 2020, which claims priority to U.S. Provisional Patent Application Ser. No. 62/978,353, filed Feb. 19, 2020, and to U.S. Provisional Patent Application Ser. No. 62/978,350, filed Feb. 19, 2020. The disclosures of each of these applications are hereby incorporated herein by reference in its entirety.

BACKGROUND

In modern medical settings, the collection, storage, and processing of health data is commonplace, resulting in the accumulation and processing of large amounts of data for each patient and procedure occurring in a typical medical facility. There are environments and operating conditions where patients may have urgent medical needs, but the access to, and ability to process, health data associated with such patients is limited. Such environments and operating conditions are known as "disconnection, intermittent, or low-bandwidth" (DIL) environments or conditions and include any situation where there are limits on the size and/or amount of data that can be transmitted, received, processed, and/or stored at any given time. However, in such environments, the need to collect, store, and exchange information remains. Examples of such environments include battlefields, remote operations, temporary emergency medical facilities, remote military operations, medical operations in times of natural disaster, etc. There are many other environments and operating conditions in which the collection, storage, and/or exchange of data may be challenging. For example, military operations and athletic competitions, as well as training for such activities, are often performed in environments that can make the collection, storage, and/or exchange of relatively large amounts of participant data difficult (e.g., DIL environments).

SUMMARY

A computer-implemented data processing method for encoding healthcare data, according to various embodiments, may include: transmitting, by one or more near-field communications (NFC) components configured at an NFC initiator device, an NFC initiation signal to a recipient device, wherein the recipient device comprises a water-resistant flexible encapsulation portion configured to encapsulate a plurality of electronic components; establishing, by one or more computer processors configured at the NFC initiator device, using the one or more NFC components configured at the NFC initiator device, an NFC field with the recipient device; receiving, by the one or more NFC components configured at the NFC initiator device, a data exchange message from the recipient device; determining, by the one or more computer processors configured at the NFC initiator device, based at least in part on the data exchange message, a BLUETOOTH address for the recipient device; establishing, by one or more BLUETOOTH components configured at the NFC initiator device, a BLUETOOTH bond with the recipient device using the BLUETOOTH address for the recipient device; receiving, by the one or more computer processors configured at the NFC initiator device, healthcare data comprising a plurality of pieces of healthcare data; compressing, by the one or more computer processors configured at the NFC initiator device, the healthcare data by: determining a value of a first piece of healthcare data of the plurality of pieces of healthcare data; determining one or more attributes of the first piece of healthcare data; determining, using a look-up table, a byte position for the first piece of healthcare data based on the one or more attributes of the first piece of healthcare data; determining, using the look-up table, an encoding type for the first piece of healthcare data based on the one or more attributes of the first piece of healthcare data; generating, based on the encoding type for the first piece of healthcare data, an encoded byte representing the first piece of healthcare data; inserting the encoded byte representing the first piece of healthcare data into a sequence of encoded bytes at the byte position for the first piece of healthcare data; and generating a dataset comprising the sequence of encoded bytes; separating, by the one or more computer processors configured at the NFC initiator device, the dataset into a plurality of subsets of the dataset; determining, by the one or more computer processors configured at the NFC initiator device, a sequence position for each subset of the plurality of subsets based on a position within the dataset of each respective subset of the plurality of subsets; generating, by the one or more computer processors configured at the NFC initiator device, a respective quick response (QR) code for each subset of the plurality of subsets, wherein each respective QR code comprises: a first visual indicator representing a respective subset of the plurality of subsets; and a second visual indicator representing a sequence position for the respective subset of the plurality of subsets; and presenting, by the one or more computer processors configured at the NFC initiator device, to a user, each respective QR code for each subset of the plurality of subsets.

In particular embodiments, the second visual indicator further represents a total quantity of subsets in the plurality of subsets. In particular embodiments, separating the dataset into the plurality of subsets of the dataset comprises: determining a data capacity of a single QR code; determining a size of the dataset; determining that the size of the dataset exceeds the data capacity of the single QR code; and in response to determining that the size of the dataset exceeds the data capacity of the single QR code, separating the dataset into the plurality of subsets of the dataset. In particular embodiments, determining the data capacity of the single QR code comprises: determining a size of a visual indicator representing a sequence position for a subset of the plurality of subsets; and determining the data capacity of the single QR code based at least in part on the size of the visual indicator representing the sequence position for the subset of the plurality of subsets. In particular embodiments, each subset of the plurality of subsets has a maximum size of about 1100 bytes. In particular embodiments, presenting the QR code for each subset of the plurality of subsets to the user comprises displaying the QR code for each subset of the plurality of subsets on a display of the NFC initiator device. In particular embodiments, presenting the QR code for each subset of the plurality of subsets to the user comprises printing the QR code for each subset of the plurality of subsets onto one or more stickers.

A non-transitory computer-readable medium comprising computer executable instructions for processing data, according to various embodiments, may include instructions for: transmitting, by one or more communications components configured at an initiator device, an initiation signal to a recipient device, wherein the recipient device comprises a data collection device comprising a flexible encapsulation portion configured to encapsulate a plurality of electronic components; establishing, by one or more computer processors configured at the initiator device, using the one or more communications components, a communications session with the recipient device; transmitting, from the one or more communications components to the recipient device, a request for data collected by the recipient device; receiving, by the one or more communications components from the recipient device, the data collected by the recipient device, the data comprising a plurality of pieces of healthcare data; compressing, by the one or more computer processors configured at the initiator device, the data by: determining a first piece of data of the plurality of pieces of data; determining one or more attributes of the first piece of data; determining, using a look-up table and based on the one or more attributes of the first piece of data, a byte position for the first piece of data; determining, using the look-up table and based on the one or more attributes of the first piece of data, an encoding type for the first piece of data; generating, based on the encoding type for the first piece of data, an encoded byte representing the first piece of data; inserting the encoded byte representing the first piece of data into a sequence of encoded bytes at the byte position for the first piece of data; and generating a dataset comprising the sequence of encoded bytes; identifying one or more subsets of the dataset; determining a sequence position indicator for each subset of the one or more subsets based on a position within the dataset of each respective subset of the one or more subsets; generating a respective quick response (QR) code for each subset of the one or more subsets, wherein each respective QR code comprises: a visual representation of the respective subset of the one or more subsets; and a visual representation of a sequence position indicator for the respective subset of the one or more subsets; and presenting each respective QR code for each subset of the one or more subsets to a user.

In particular embodiments, the data collected by the recipient device comprises sensor data collected from one or more sensors configured on a wearer of the recipient device. In particular embodiments, the one or more communications components comprise one or more wireless communications components; and establishing the communications session with the recipient device comprises establishing a wireless communications session with the recipient device. In particular embodiments, the one or more communications components comprise one or more wired communications components; and establishing the communications session with the recipient device comprises establishing a wired communications session with the recipient device. In particular embodiments, presenting each respective QR code for each subset of the one or more subsets to the user comprises: generating a plurality of display images, wherein each display image of the plurality of display images comprises one or more QR codes, and wherein each of the one or more QR codes is associated with a respective subset of the one or more subsets; and sequentially presenting the plurality of display images on a display of the initiator device. In particular embodiments, presenting each respective QR code for each subset of the one or more subsets to the user comprises: generating a plurality of display images, wherein each display image of the plurality of display images comprises one or more QR codes, and wherein each of the one or more QR codes is associated with a respective subset of the one or more subsets; and storing each display image of the plurality of display images as a video frame in video content data. In particular embodiments, each respective QR code further comprises a visual representation of a total quantity of subsets of the one or more subsets. In particular embodiments, the total quantity of subsets of the one or more subsets equals the sequence position indicator.

A data processing system for decoding encoded data, according to various embodiments, may include: one or more processors; one or more digital image capture components; and computer memory storing computer-executable instructions that, when executed by the one or more processors, cause the one or more processors to perform operations comprising: capturing, by the one or more digital image capture components, one or more images; identifying, by the one or more processors, one or more quick response (QR) codes in each of the one or more images; analyzing, by the one or more processors, each of the one or more QR codes to determine, for each respective QR code of the one or more QR codes: a sequence position for a respective QR code; and a subset of data represented by the respective QR code; generating, by the one or more processors, a dataset comprising each subset of data represented by each of the one or more QR codes based at least in part on each respective sequence position for each of the one or more QR codes; identifying, by the one or more processors, a sequence of encoded bytes within the dataset; decompressing, by the one or more processors, the dataset by: determining a first byte position within the sequence of encoded bytes for a first encoded byte of the sequence of encoded bytes; determining, based on the first byte position within the sequence of encoded bytes for the first encoded byte, using a look-up table, one or more data attributes associated with a first piece of data; determining, based on the one or more data attributes associated with the first piece of data, a decoding type for the first piece of data; generating, based on the decoding type for the first piece of data, a value of the first piece of data using the first encoded byte; storing, in the computer memory, the one or more data attributes associated with the first piece of data and the value of the first piece of data; associating, in the computer memory, the one or more data attributes associated with the first piece of data and the value of the first piece of data; generating a structured record comprising the one or more data attributes associated with the first piece of data and the value of the first piece of data; determining a second byte position within the sequence of encoded bytes for a second encoded byte of the sequence of encoded bytes; determining, based on the second byte position within the sequence of encoded bytes for the second encoded byte, using the look-up table, that the second encoded byte indicates the end of the structured record; and storing the structured record in computer memory.

In particular embodiments, the sequence position for the respective QR code comprises: a position of the subset of data within the dataset; and a total quantity of subsets of data within the dataset. In particular embodiments, capturing the one or more images comprises capturing a sequence of images presented as frames of video content. In particular embodiments, each of the one or more images comprises a plurality of representations of QR codes. In particular embodiments, one or more subsets of data within the dataset comprises healthcare data or sensor data.

A wearable data processing system for processing sensor data, according to various embodiments, may include: a housing; a moisture-resistant encapsulation portion configured within the housing; a microprocessor configured within the moisture-resistant encapsulation portion; a power supply configured within the moisture-resistant encapsulation portion and configured to supply power to the microprocessor; data storage media configured within the moisture-resistant encapsulation portion and communicatively connected to the microprocessor; a Bluetooth communications processor configured within the moisture-resistant encapsulation portion and communicatively connected to the microprocessor; one or more Bluetooth communications antennas configured within the moisture-resistant encapsulation portion and communicatively connected to the Bluetooth communications processor; wherein the microprocessor is configured to: transmit a first activation signal to the Bluetooth communications processor; instruct the Bluetooth communications processor to collect sensor data from one or more sensors configured on a wearer of the wearable data processing system; receive the sensor data from the Bluetooth communications processor; and store the sensor data in the data storage media; a near-field communications (NFC) processor configured within the moisture-resistant encapsulation portion and communicatively connected to the microprocessor; and an NFC antenna configured within the moisture-resistant encapsulation portion and communicatively connected to the NFC processor; wherein the NFC processor is configured to: at least partially in response to receiving an NFC signal from an NFC initiator device via the NFC antenna, establish an NFC field with the NFC initiator device; and at least partially in response to establishing the NFC field with the NFC initiator device, transmit a second activation signal to the microprocessor; and wherein the microprocessor is further configured to: at least partially in response to receiving the second activation signal from the NFC processor, provide power to the data storage media; receive a request for the sensor data from an external device; at least partially in response to receiving the request the sensor data from the external device, retrieve the sensor data from the data storage media; and transmit the sensor data to the external device.

In particular embodiments, the microprocessor configured to transmit the sensor data to the external device comprises the microprocessor configured to: instruct the Bluetooth communications processor to establish a Bluetooth communications session with the external device; and instruct the Bluetooth communications processor to transmit the sensor data to the external device via the Bluetooth communications session. In particular embodiments, the data processing system further comprises: a Wi-Fi communications processor configured within the moisture-resistant encapsulation portion and communicatively connected to the microprocessor; and one or more Wi-Fi communications antennas configured within the moisture-resistant encapsulation portion and communicatively connected to the wireless communications processor; wherein the microprocessor configured to transmit the sensor data to the external device comprises the microprocessor configured to: instruct the Wi-Fi communications processor to establish a Wi-Fi communications session with the external device; and instruct the Wi-Fi communications processor to transmit the sensor data to the external device via the Wi-Fi communications session. In particular embodiments, the microprocessor configured to store the sensor data in the data storage media comprises the microprocessor configured to: encode the sensor data to generate encoded sensor data; and store the encoded sensor data in the data storage media. In particular embodiments, the NFC processor is further configured to: detect a breaking of the NFC field; and at least partially in response to detecting the breaking of the NFC field, transmit a deactivation signal to the microprocessor. In particular embodiments, the microprocessor configured to store the sensor data in the data storage media comprises the microprocessor configured to: generate a structured record based at least in part on the sensor data; and store the structured record in the data storage media. In particular embodiments, the microprocessor is configured to: receive a time period from the external device; and transmit the first activation signal to the Bluetooth communications processor and instruct the Bluetooth communications processor to collect the sensor data from the one or more sensors periodically based at least in part on the time period.

A user-affixable device configured to perform data processing of sensor data, according to various embodiments, may include: a housing comprising an encapsulation portion configured to encapsulate a plurality of electronic components, and wherein the plurality of electronic components comprises: a microprocessor; data storage media communicatively connected to the microprocessor; a power supply configured to supply power to the microprocessor; a first communications signal reception component communicatively connected to the microprocessor; and a second communications signal reception component communicatively connected to the microprocessor, wherein the microprocessor is configured to: analyze a timer to determine whether a time period has expired; at least partially in response to determining that the time period has expired: activate the first communications signal reception component; retrieve sensor data from each of one or more sensors affixed to a user using the first communications signal reception component; aggregate the sensor data with historical sensor data to generate aggregated sensor data; store the aggregated sensor data in the data storage media; deactivate the first communications signal reception component; and reset the timer; receive a request from an external device for the aggregated sensor data via the second communications signal reception component; at least partially in response to receiving the request from the external device, retrieve the aggregated sensor data from the data storage media; and transmit the aggregated sensor data to the external device using the second communications signal reception component.

In particular embodiments, the second communications signal reception component comprises a physical communications signal reception component comprising one of: (a) a universal serial bus (USB) component; (b) a mini-USB component; or (c) a micro-USB component. In particular embodiments, the second communications signal reception component is further configured to: receive power via the communications signal reception component; and supply power one or more of the plurality of electronic components. In particular embodiments, the second communications signal reception component comprises a wireless communications signal reception component comprising one of: (a) a Bluetooth component; (b) a near-field communications (NFC) component; or (c) a Wi-Fi component. In particular embodiments, the microprocessor configured to retrieve the sensor data from each of the one or more sensors comprises the microprocessor configured to retrieve health-related data from one or more of: a heart rate sensor; a body temperature sensor; a sweat sensor; and a biosensor. In particular embodiments, the first communications signal reception component comprises one or more Bluetooth communications components; and the microprocessor configured to retrieve the sensor data from each of the one or more sensors comprises the microprocessor configured to: establish a Bluetooth Low Energy communications session with one or more of the one or more sensors; and retrieve at least a subset of the sensor data from the one or more of the one or more sensors using the Bluetooth Low Energy communications session. In particular embodiments, the first communications signal reception component comprises a physical communications signal reception component; the physical communications signal reception component is communicatively connected to one or more of the one or more sensors with a physical connection; and the microprocessor configured to retrieve the sensor data from each of the one or more sensors comprises the microprocessor configured to retrieve at least a subset of the sensor data from the one or more of the one or more sensors using the physical connection between the physical communications signal reception component and the one or more of the one or more sensors.

A data processing method for collection and processing of sensor data, according to various embodiments, may include: periodically activating, by a microprocessor, Bluetooth communications components configured within a moisture-resistant encapsulation portion configured within a housing, wherein: the microprocessor is configured within the moisture-resistant encapsulation portion of the housing; the housing is removably affixed to a wearer; and the Bluetooth communications components comprise: a Bluetooth communications processor communicatively connected to a microprocessor; and one or more Bluetooth communications antennas communicatively connected to the Bluetooth communications processor; at least partially in response to activating the Bluetooth communications components, transmitting an instruction, from the microprocessor to the Bluetooth communications components, instructing the Bluetooth communications components to: establish a Bluetooth communications session with each of one or more sensors removably affixed to the wearer; and collect sensor data from one or more of the one or more sensors using a respective Bluetooth communications session; receiving, at the microprocessor from the Bluetooth communications components, the collected sensor data; at least partially in response to receiving the collected sensor data, deactivating, by the microprocessor, the Bluetooth communications components; storing, by the microprocessor in a data storage component, the collected sensor data, wherein the data storage component configured within the moisture-resistant encapsulation portion of the housing; receiving, at the microprocessor from an external device, a request for sensor data; at least partially in response to receiving the request: retrieving, by the microprocessor from the data storage component, responsive data comprising the collected data; and transmitting, by the microprocessor to the external device, the responsive data.

In particular embodiments, the method may also include periodically activating, by the microprocessor, physical communications components configured within the moisture-resistant encapsulation portion of the housing; at least partially in response to activating the physical communications components, transmitting an instruction, from the microprocessor to the physical communications components, instructing the physical communications components to collect sensor data from one or more of the one or more sensors using a physical communications connection; receiving, at the microprocessor from the physical communications components, second collected sensor data; at least partially in response to receiving the second collected sensor data, deactivating, by the microprocessor, the physical communications components; and storing, by the microprocessor in the data storage component, the second collected sensor data. In particular embodiments, the method may also include aggregating, by the microprocessor, the collected sensor data and the second collected sensor data to generate the responsive data; and storing, by the microprocessor in a data storage component, the responsive data. In particular embodiments, the housing is removably affixed to an exoskeleton that is removably affixed to the wearer. In particular embodiments, the wearer is one of a soldier or an athlete. In particular embodiments, the one or more sensors comprise one or more of: an environmental sensor; a movement sensor; or a geographic location sensor.

A computer-implemented data processing method for encoding healthcare data, according to various embodiments, may include: receiving, by one or more computer processors, healthcare data comprising a plurality of pieces of healthcare data; determining, by one or more computer processors, a value of a first piece of healthcare data of the plurality of pieces of healthcare data; determining, by one or more computer processors, one or more attributes of the first piece of healthcare data; determining, by one or more computer processors using a look-up table, a byte position for the first piece of healthcare data based on the one or more attributes of the first piece of healthcare data; determining, by one or more computer processors using the look-up table, an encoding type for the first piece of healthcare data based on the one or more attributes of the first piece of healthcare data; generating, by one or more computer processors based on the encoding type for the first piece of healthcare data, an encoded byte representing the first piece of healthcare data; inserting, by one or more processors, the encoded byte representing the first piece of healthcare data into a sequence of encoded bytes at the byte position for the first piece of healthcare data; generating, by one or more computer processors, a data stream comprising the sequence of encoded bytes; and transmitting, by one or more computer processors using one or more wireless communications components, the data stream to a recipient device.

In particular embodiments, the method may include inserting a special byte code into the sequence of encoded bytes, wherein the special byte code indicates one of: (a) a separation of complete medical data records; (b) a separation of medical values; (c) a separation of types of medical data; (d) an end of a complete medical data record; (e) an end of a structure of a medical data record; and (f) an end of a substructure of a medical data record. In particular embodiments, one or more of the plurality of pieces of healthcare data is a piece of healthcare data selected from a group consisting of: (a) a vital sign code; (b) a unit of measurement; (c) an observed measurement; and (d) a timestamp. In particular embodiments, the look-up table comprises a plurality of encoding bytes, and for each encoding byte of the plurality of encoding bytes, the look-up table comprises a respective code system, a respective code value, and a respective display text. In particular embodiments, the look-up table is one of a plurality of look-up tables, and each look-up table of the plurality of look-up tables is associated with a distinct medical domain. In particular embodiments, that method may also include determining that there are no remaining pieces of healthcare data of the plurality of pieces of healthcare data to encode; and at least partially in response to determining that there are no remaining pieces of healthcare data of the plurality of pieces of healthcare data to encode, inserting a special encoded byte into the sequence of encoded bytes at a position in the sequence of encoded bytes immediately following a position of a last encoded byte in the sequence of encoded bytes, wherein the special encoded byte indicates the end of the sequence of encoded bytes. In particular embodiments, the method may also include determining that there is unused space in an amount of data space allotted to the sequence of encoded bytes; and the special encoded byte into the sequence of encoded bytes at a position in the sequence of encoded bytes immediately following a position of a last encoded byte in the sequence of encoded bytes is further inserted into the sequence of encoded bytes at least partially in response to determining that there is unused space in the amount of data space allotted to the sequence of encoded bytes. In particular embodiments, determining the encoding type for the first piece of healthcare data based on the one or more attributes of the first piece of healthcare data comprises determining that the encoding type for the first piece of healthcare data is binary encoding. In particular embodiments, the first piece of healthcare data comprises a character string representation of a numeric value; and generating the encoded byte representing the first piece of healthcare data based on the encoding type for the first piece of healthcare data comprises: converting the character string representation of the numeric value to a binary representation of the numeric value; and generating the encoded byte comprising the binary representation of the numeric value.

A data processing system for encoding healthcare data, according to various embodiments, may include: data reception means for receiving healthcare data comprising a plurality of pieces of healthcare data; healthcare data value determination means for determining a value of a first piece of healthcare data of the plurality of pieces of healthcare data; healthcare data attribute determination means for determining one or more attributes of the first piece of healthcare data; healthcare data encoded byte position determination means for determining a byte position for the first piece of healthcare data based on the one or more attributes of the first piece of healthcare data using a look-up table; healthcare data encoding type determination means for determining an encoding type for the first piece of healthcare data based on the one or more attributes of the first piece of healthcare data using a look-up table; healthcare data encoded byte generation means for generating an encoded byte representing the first piece of healthcare data based on the encoding type for the first piece of healthcare data; encoded byte insertion means for inserting the encoded byte representing the first piece of healthcare data into a sequence of encoded bytes at the byte position for the first piece of healthcare data; data stream generation means for generating a data stream comprising the sequence of encoded bytes; and wireless transmission means for wirelessly transmitting the data stream to a recipient device.

A data processing system for decoding encoded healthcare data, according to various embodiments, may include: one or more processors; one or more wireless communications components; and computer memory storing computer-executable instructions that, when executed by the one or more processors, cause the one or more processors to perform operations comprising: receiving, at the one or more processors via the one or more wireless communications components, a data stream comprising a sequence of encoded bytes; determining a first byte position within the sequence of encoded bytes of a first encoded byte of the sequence of encoded bytes; determining, based on the first byte position within the sequence of encoded bytes of the first encoded byte, using a look-up table, one or more healthcare data attributes associated with a first piece of healthcare data; determining, based on the one or more healthcare data attributes associated with the first piece of healthcare data, a decoding type for the first piece of healthcare data; generating, based on the decoding type for the first piece of healthcare data, a value of the first piece of healthcare data using the first encoded byte; storing, in the computer memory, the one or more healthcare data attributes associated with the first piece of healthcare data and the value of the first piece of healthcare data; associating, in the computer memory, the one or more healthcare data attributes associated with the first piece of healthcare data and the value of the first piece of healthcare data; and generating a healthcare record comprising the one or more healthcare data attributes associated with the first piece of healthcare data and the value of the first piece of healthcare data.

In particular embodiments, determining the decoding type for the first piece of healthcare data comprises determining that the decoding type for the first piece of healthcare data is binary encoding. In particular embodiments, the first encoded byte comprises a binary representation of a numeric value; and generating, based on the decoding type for the first piece of healthcare data, the value of the first piece of healthcare data using the first encoded byte comprises converting the binary representation of the numeric value to a character string representation of the numeric value. In particular embodiments, one or more of the one or more healthcare data attributes associated with the first piece of healthcare data comprise one or more attributes selected from a group consisting of: (a) a code system; (b) a code value; and (c) a display text. In particular embodiments, one or more healthcare data attributes associated with the first piece of healthcare data comprises a code system, and wherein the code system is the Logical Observation Identifiers Names and Codes (LOINC) system health measurement terminology system. In particular embodiments, the operations may include: determining a second byte position within the sequence of encoded bytes of a second encoded byte of the sequence of encoded bytes; determining, based on the second byte position within the sequence of encoded bytes of the second encoded byte, using the look-up table, that the second encoded byte is a special byte code. In particular embodiments, the special byte code indicates the termination of the data stream.

A non-transitory computer-readable medium, according to various embodiments, may include computer executable instructions for: receiving, by one or more computer processors, healthcare data comprising a plurality of pieces of healthcare data; determining, by one or more computer processors, a first piece of healthcare data of the plurality of pieces of healthcare data; determining, by one or more computer processors, one or more attributes of the first piece of healthcare data; determining, by one or more computer processors, using a look-up table and based on the one or more attributes of the first piece of healthcare data, a byte position for the first piece of healthcare data; determining, by one or more computer processors, using the look-up table and based on the one or more attributes of the first piece of healthcare data, an encoding type for the first piece of healthcare data, wherein the encoding type comprises binary encoding; determining, by one or more computer processors, a numeric value associated with the first piece of healthcare data, wherein the numeric value is representing in the first piece of healthcare data by a character string; determining, by one or more computer processors based on the encoding type for the first piece of healthcare data, a binary representation of the numeric value associated with the first piece of healthcare data; generating, by one or more computer processors, an encoded byte representing the first piece of healthcare data comprising the numeric value associated with the first piece of healthcare data; inserting, by one or more processors, the encoded byte representing the first piece of healthcare data into a sequence of encoded bytes at the byte position for the first piece of healthcare data; generating, by one or more computer processors, a data stream comprising the sequence of encoded bytes; and transmitting, by one or more computer processors using one or more wireless communications components, the data stream to a recipient device.

In particular embodiments, the computer executable instructions for may further include instructions for determining, using the look-up table based on the one or more attributes of the first piece of healthcare data, a type of units for the first piece of healthcare data. In particular embodiments, the plurality of pieces of healthcare data comprises a data structure representing a patient encounter with a healthcare provider. In particular embodiments, the data structure comprises a first substructure comprising a first subset of the plurality of pieces of healthcare data comprising demographic data associated with a patient. In particular embodiments, the data structure comprises a second substructure comprising a second subset of the plurality of pieces of healthcare data comprising vital signs data associated with the patient.

A user-affixable device configured to transmit, receive, and store healthcare data, according to various embodiments, may include: a bandage comprising an adhesive portion, an absorbent portion, and a water-resistant flexible encapsulation portion, wherein the water-resistant flexible encapsulation portion is configured to encapsulation plurality of electronic components, and wherein the plurality of electronic components comprises: a microprocessor; data storage media communicatively connected to the microprocessor; a near-field communications (NFC) processor communicatively connected to the microprocessor; an NFC antenna communicatively connected to the NFC processor, wherein the NFC processor is configured to: at least partially in response to receiving an NFC signal from an NFC initiator device via the NFC antenna, establish an NFC field with the NFC initiator device; and at least partially in response to establishing the NFC field with the NFC initiator device, transmit an activation signal to the microprocessor; a power supply configured to supply power to the microprocessor; a Bluetooth processor communicatively connected to the microprocessor; and a Bluetooth antenna communicatively connected to the NFC Bluetooth processor; wherein the microprocessor is configured to, at least partially in response to receiving the activation signal from the NFC processor, provide power to the data storage media and the Bluetooth processor; and wherein the Bluetooth processor is configured to, at least partially in response to receiving power from the microprocessor, establish a Bluetooth communications session with a wireless communications device.

In particular embodiments, the NFC processor is further configured to: detect a breaking of the NFC field; and at least partially in response to detecting the breaking of the NFC field, transmit a deactivation signal to the microprocessor. In particular embodiments, the microprocessor is further configured to: at least partially in response to receiving the deactivation signal from the NFC processor, cease providing power to the data storage media and the Bluetooth processor. In particular embodiments, the Bluetooth processor is further configured to: detect a termination of the Bluetooth communications session with the wireless communications device; and at least partially in response to detecting the termination of the Bluetooth communications session with the wireless communications device, transmit a deactivation signal to the microprocessor. In particular embodiments, the microprocessor is further configured to: at least partially in response to receiving the deactivation signal from the Bluetooth processor, cease providing power to the data storage media and the Bluetooth processor. In particular embodiments, the wireless communications device is a device distinct from the NFC initiator device. In particular embodiments, the Bluetooth processor is configured to, at least partially in response to receiving power from the microprocessor, transmit a message to the NFC initiator device indicating that the user-affixable device has Bluetooth capabilities. In particular embodiments, the Bluetooth processor is configured to establish the Bluetooth communications session with the NFC initiator device via the Bluetooth antenna. In particular embodiments, the Bluetooth processor is configured to: receive healthcare data via the Bluetooth antenna; and transmit the healthcare data to the microprocessor for storage at the data storage media.

A smart bandage system for processing healthcare data, according to various embodiments, may include: an adhesive means for adhering the smart bandage system to skin of a human patient; an absorbent means for absorbing moisture from the human patient; a flexible, water-resistant encapsulation means for housing a plurality of electronic components; a computer processing means for processing healthcare data and for providing power to one or more of the plurality of electronic components at least partially in response to receiving an activation signal from short-range wireless communications means; a data storage means for storing healthcare data; the short-range wireless communications means for communicating with one or more short-range wireless initiator devices using short-range wireless communications and for transmitting the activation signal to the computer processing means upon establishing short-range wireless communications session with the one or more short-range wireless initiator devices; a battery means for supplying power to the microprocessor; and a Bluetooth communications means for communicating with one or more Bluetooth-capable devices and for, at least partially in response to receiving power from the computer processing means, establishing a Bluetooth communications session with the one or more NFC initiator devices.

A data processing system for processing healthcare data, according to various embodiments, may include: a housing; a moisture-resistant encapsulation portion configured within the housing; a microprocessor configured within the moisture-resistant encapsulation portion; data storage media configured within the moisture-resistant encapsulation portion and communicatively connected to the microprocessor; a near-field communications (NFC) processor configured within the moisture-resistant encapsulation portion and communicatively connected to the microprocessor; an NFC antenna configured within the moisture-resistant encapsulation portion and communicatively connected to the NFC processor, wherein the NFC processor is configured to: at least partially in response to receiving an NFC signal from an NFC initiator device via the NFC antenna, establish an NFC field with the NFC initiator device; and at least partially in response to establishing the NFC field with the NFC initiator device, transmit an activation signal to the microprocessor; a power supply configured within the moisture-resistant encapsulation portion and configured to supply power to the microprocessor; a wireless communications processor configured within the moisture-resistant encapsulation portion and communicatively connected to the microprocessor; and one or more wireless communications antennas configured within the moisture-resistant encapsulation portion and communicatively connected to the wireless communications processor; wherein the microprocessor is configured to, at least partially in response to receiving the first activation signal from the NFC processor, provide power to the data storage media and the wireless communications processor; and wherein the wireless communications processor is configured to, at least partially in response to receiving power from the microprocessor, establish a wireless communications session with a wireless communications device using the one or more wireless communications antennas.

In particular embodiments, the wireless communications processor is a Wi-Fi processor; the one or more wireless communications antennas are one or more Wi-Fi antennas; and the wireless communications session is a Wi-Fi communications session. In particular embodiments, the wireless communications processor is further configured to: receive a request for healthcare data at the wireless communications processor from the wireless communications device via the wireless communications session; transmit the request for the healthcare data from the wireless communications processor to the microprocessor; retrieve the requested healthcare data from the data storage media by the microprocessor; transmit the requested healthcare data from the microprocessor to the wireless communications processor; receive the requested healthcare data from the microprocessor at the wireless communications processor; and transmit the requested healthcare data from the wireless communications processor to the wireless communications device via the wireless communications session using the one or more wireless communications antennas. In particular embodiments, the requested healthcare data comprises a sequence of encoded bytes. In particular embodiments, the NFC processor is further configured to detect a breaking of the NFC field; and at least partially in response to detecting the breaking of the NFC field, the NFC processor is further configured to transmit a deactivation signal to the microprocessor. In particular embodiments, at least partially in response to receiving the deactivation signal from the NFC processor, the microprocessor is configured to transmit an instruction to the wireless communications processor to terminate the wireless communications session with the wireless communications device. In particular embodiments, the housing is a band suitable for attachment about a human arm or a human leg. In particular embodiments, the housing is a bandage suitable for attachment to human skin.

A method of operating a healthcare data processing system, according to various embodiments, may include: establishing, by a near-field communications (NFC) processor via an NFC antenna, an NFC field with an NFC initiator device, wherein the NFC processor and the NFC antenna are encapsulated in a moisture-resistant bandage housing; transmitting an activation signal from the NFC processor to a microprocessor, wherein the microprocessor is encapsulated in the moisture-resistant bandage housing; at least partially in response to receiving the activation signal from the NFC processor, providing power, by a battery via the microprocessor, to a Bluetooth processor and data storage media, wherein the battery, the Bluetooth processor, and the data storage media are encapsulated in the moisture-resistant bandage housing; at least partially in response to receiving power from the battery via the microprocessor, establishing, by the Bluetooth processor via one or more Bluetooth antennas, a Bluetooth communications session with the NFC initiator device; wherein the one or more Bluetooth antennas are encapsulated in the moisture-resistant bandage housing; exchanging data, by the Bluetooth processor using the one or more Bluetooth antennas, via the Bluetooth communications session with the NFC initiator device; detecting, at the Bluetooth processor via the one or more Bluetooth antennas, a termination of the Bluetooth communications session with the NFC initiator device; at least partially in response to detecting the termination of the Bluetooth communications session with the NFC initiator device, transmitting, from the Bluetooth processor, a deactivation signal to the microprocessor; and at least partially in response to receiving the deactivation signal from the Bluetooth processor, ceasing, by the microprocessor, providing power from the battery to the Bluetooth processor and the data storage media.

In particular embodiments, the method may also include establishing, by the Bluetooth processor using the one or more Bluetooth antennas, one or more Bluetooth sessions with one or more respective health data sensors configured on a human user; receiving, via the one or more Bluetooth sessions with the one or more respective health data sensors, by the Bluetooth processor using the one or more Bluetooth antennas, health measurement data; transmitting, from the Bluetooth processor to the microprocessor, the health measurement data; receiving, at the microprocessor from the Bluetooth processor, the health measurement data; and storing, by the microprocessor, the health measurement data in the data storage media. In particular embodiments, one or more of the one or more health data sensors is a sensor selected from a group consisting of: (a) a heart rate sensor; (b) a body temperature sensor; (c) a sweat sensor; (d) a biosensor; and (e) an environmental sensor. In particular embodiments, exchanging data via the Bluetooth communications session with the NFC initiator device comprises: retrieving, by the microprocessor, a subset of the health measurement data from the data storage media; transmitting the subset of the health measurement data from the microprocessor to the Bluetooth processor; receiving the subset of the health measurement data from the microprocessor at the Bluetooth processor; and transmitting the subset of the health measurement data from the Bluetooth processor to the NFC initiator device via the Bluetooth communications session with the NFC initiator using the one or more Bluetooth antennas.

A data processing system for processing healthcare data, according to various embodiments, may include: a housing; a moisture-resistant encapsulation portion configured within the housing; a microprocessor configured within the moisture-resistant encapsulation portion; data storage media configured within the moisture-resistant encapsulation portion and communicatively connected to the microprocessor; a near-field communications (NFC) processor configured within the moisture-resistant encapsulation portion and communicatively connected to the microprocessor; an NFC antenna configured within the moisture-resistant encapsulation portion and communicatively connected to the NFC processor, wherein the NFC processor is configured to: at least partially in response to receiving an NFC signal from an NFC initiator device via the NFC antenna, establish an NFC field with the NFC initiator device; and at least partially in response to establishing the NFC field with the NFC initiator device, transmit an activation signal to the microprocessor; a power supply configured within the moisture-resistant encapsulation portion and configured to supply power to the microprocessor; a wireless communications processor configured within the moisture-resistant encapsulation portion and communicatively connected to the microprocessor; and one or more wireless communications antennas configured within the moisture-resistant encapsulation portion and communicatively connected to the wireless communications processor; wherein the microprocessor is configured to: at least partially in response to receiving the activation signal from the NFC processor, provide power to the data storage media and the wireless communications processor; receive a request for healthcare data from the wireless communications processor; at least partially in response to receiving the request for healthcare data from the wireless communications processor, retrieve requested healthcare data from the data storage media; and transmit the requested healthcare data to the wireless communications processor; and wherein the wireless communications processor is configured to: at least partially in response to receiving power from the microprocessor, establish a wireless communications session with a wireless communications component of a remote computing device using the one or more wireless communications antennas; receive the request for the healthcare data from the remote computing device via the wireless communications session; transmit the request for the healthcare data to the microprocessor; receive the requested healthcare data from the microprocessor; and transmit the requested healthcare data to the remote computing device via the wireless communications session using the one or more wireless communications antennas.

In particular embodiments, the wireless communications processor is a Wi-Fi processor; the one or more wireless communications antennas are one or more Wi-Fi antennas; and the wireless communications session is a Wi-Fi communications session. In particular embodiments, the remote computing device comprises one of: (a) a laptop computer; (b) a desktop computer; or (a) a server computer. In particular embodiments, the wireless communications processor configured to transmit the requested healthcare data to the remote computing device via the wireless communications session using the one or more wireless communications antennas comprises: the wireless communications processor configured to transmit the requested healthcare data to the remote computing device via the wireless communications session for relay to a cloud-based system using the one or more wireless communications antennas. In particular embodiments, the NFC processor is further configured to detect a breaking of the NFC field; and at least partially in response to detecting the breaking of the NFC field, the NFC processor is further configured to transmit a deactivation signal to the microprocessor. In particular embodiments, at least partially in response to receiving the deactivation signal from the NFC processor, the microprocessor is configured to transmit an instruction to the wireless communications processor to terminate the wireless communications session with the wireless communications device. In particular embodiments, the housing is a disposable bandage component configured to removably accept the moisture-resistant encapsulation portion; and the moisture-resistant encapsulation portion is a durable component and configured to be removably affixed to a plurality of disposable bandage components. In particular embodiments, the disposable bandage component is a bandage suitable for attachment to human skin.

A user-affixable device configured to perform data processing of healthcare data, according to various embodiments, may include: a bandage comprising an adhesive portion, an absorbent portion, and a removable water-resistant flexible encapsulation portion, wherein the removable water-resistant flexible encapsulation portion is configured to encapsulate plurality of electronic components, and wherein the plurality of electronic components comprises: a microprocessor; data storage media communicatively connected to the microprocessor; a communications processor communicatively connected to the microprocessor; a communications signal reception component communicatively connected to the communications processor, wherein the communications processor is configured to: at least partially in response to receiving an activation signal from an external device via the communications signal reception component, establish a communications session with the external device; at least partially in response to receiving the activation signal from the external device via the communications signal reception component, transmit an activation signal to the microprocessor; receive a request for healthcare data from the external device via the communications signal reception component; transmit the request for the healthcare data to the microprocessor; receive the requested healthcare data from the microprocessor; transmit the requested healthcare data to the external device via the communications signal reception component; detect a termination of the communications session with the external device; and at least partially in response to detecting the termination of the communications session with the external device, transmit a deactivation signal to the microprocessor; and a power supply configured to supply power to the microprocessor.

In particular embodiments, the communications processor is further configured to: receive power via the communications signal reception component; and supply power one or more of the plurality of electronic components. In particular embodiments, the communications signal reception component is a physical communications signal reception component comprising one of: (a) a universal serial bus (USB) component; (b) a mini-USB component; or (c) a micro-USB component. In particular embodiments, the communications signal reception component is a wireless communications signal reception component comprising one of: (a) a Bluetooth component; (b) a near-field communications (NFC) component; or (c) a Wi-Fi component. In particular embodiments, the communications processor configured to transmit the requested healthcare data to the external device via the communications signal reception component comprises: the communications processor configured to transmit the requested healthcare data to the external device via the communications signal reception component for integration with one or more existing healthcare records. In particular embodiments, the plurality of electronic components further comprise: a Bluetooth processor communicatively connected to the microprocessor; and a Bluetooth antenna communicatively connected to the Bluetooth processor; wherein the microprocessor is configured to, at least partially in response to receiving the activation signal from the communications processor, provide power to the data storage media and the Bluetooth processor; and wherein the Bluetooth processor is configured to, at least partially in response to receiving power from the microprocessor, establish a Bluetooth communications session with a wireless communications device. In particular embodiments, the Bluetooth processor is configured to: receive a Bluetooth beacon transmission comprising location data via the Bluetooth antenna; and transmit the location data to the microprocessor for storage at the data storage media.

A method of operating a healthcare data processing system, according to various embodiments, may include: receiving, by a communications processor via one or more communications signal reception components, a power signal from a remote computing device, wherein the communications processor and the one or more communications signal reception components are encapsulated in a reusable moisture-resistant housing removable affixed to a portable component; establishing, by the communications processor via the one or more communications signal reception components, a communications session with the remote computing device; at least partially in response to establishing the communications session with the remote computing device, transmitting an activation signal from the communications processor to a microprocessor, wherein the microprocessor is encapsulated in the reusable moisture-resistant bandage housing; receiving, by the communications processor via the one or more communications signal reception components, power from the remote computing device; at least partially in response to receiving the power from the remote computing device, providing power, by the communications processor, to the microprocessor, data storage media, and a battery, wherein the microprocessor, the data storage media, and the battery are encapsulated in the moisture-resistant bandage housing; exchanging data, by the communications processor via the one or more communications signal reception components, with the remote computing device; detecting, by the communications processor via the one or more communications signal reception components, a termination of the communications session with the remote computing device; at least partially in response to detecting the termination of the communications session with the remote computing device, transmitting, from the communications processor, a deactivation signal to the microprocessor; and at least partially in response to detecting the termination of the communications session with the remote computing device, ceasing, by the communications processor, providing power to the microprocessor, data storage media, and a battery.

In particular embodiments, receiving, by the communications processor via the one or more communications signal reception components, the power signal from the remote computing device comprises receiving a near-field communications (NFC) signal from the remote computing device; and establishing, by the communications processor via the one or more communications signal reception components, the communications session with the remote computing device comprises establishing an NFC field with the remote computing device. In particular embodiments, detecting, by the communications processor via the one or more communications signal reception components, the termination of the communications session with the remote computing device comprises detecting, by the communications processor via the one or more communications signal reception components, a breaking of the NFC field. In particular embodiments, receiving, by the communications processor via the one or more communications signal reception components, the power signal from the remote computing device comprises receiving a Bluetooth signal from the remote computing device; and establishing, by the communications processor via the one or more communications signal reception components, the communications session with the remote computing device comprises establishing a Bluetooth communications session with the remote computing device. In particular embodiments, detecting, by the communications processor via the one or more communications signal reception components, the termination of the communications session with the remote computing device comprises detecting, by the communications processor via the one or more communications signal reception components, a termination of the Bluetooth communications session with the remote computing device. In particular embodiments, the portable component is a disposable bandage suitable for attachment to human skin.

BRIEF DESCRIPTION OF THE DRAWINGS

Various embodiments are described below. In the course of this description, reference will be made to the accompanying drawings, which are not necessarily drawn to scale, and wherein.

DETAILED DESCRIPTION

Various embodiments now will be described more fully hereinafter with reference to the accompanying drawings. It should be understood that the invention may be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

Exemplary System

Figure 1:
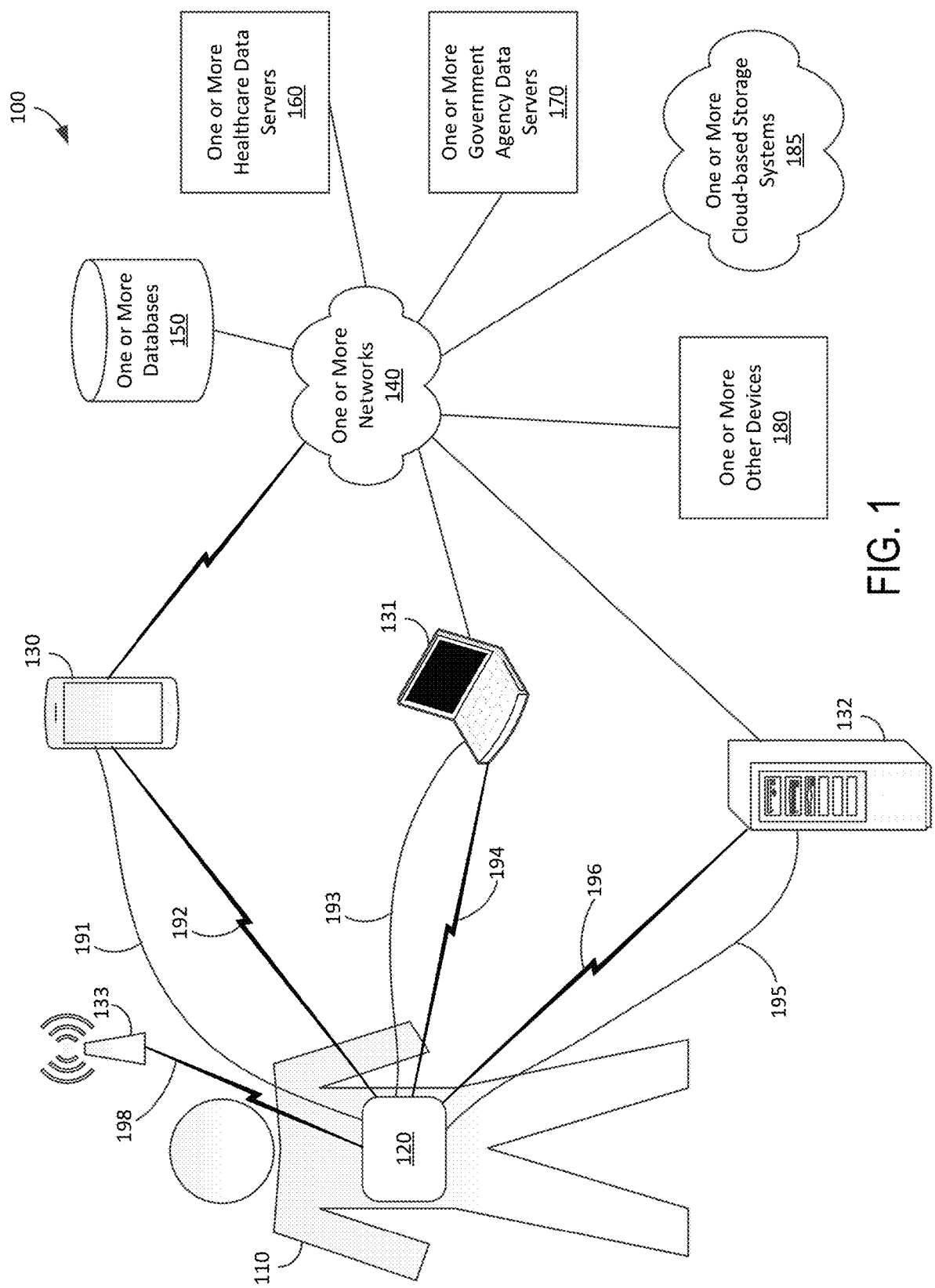
FIG. 1 is a diagram illustrating an exemplary system in which various embodiments may be implemented.

FIG. 1 illustrates an exemplary system 100 in which various embodiments may be implemented. In system 100, a person (e.g., patient) 110 may be experiencing some type of medical issue. For example, the patient 110 may be experiencing a serious condition that renders the patient 110 unconscious or otherwise unable to communicate with healthcare providers, such as a traumatic injury or a debilitating illness (e.g., viral infection, bacterial infection, etc.). Note that animal patients (as opposed to human patients) are also contemplated herein and are typically incapable of substantive communication with human healthcare providers. In other examples, the patient 110 may be less affected by illness or injury, or may not be affected at all. In still other examples, the patient 110 may be any individual in a healthcare system where healthcare data and other related information may be of use to those providing healthcare to the patient 110. In such situations, the patient 110 may not be able to provide his or her own healthcare data due to incapacity and/or inability to easily recite such data. Furthermore, the healthcare providers attending to the patient 110 may not have immediate access to remote computing devices, network connectivity, etc. in order to retrieve the patient 110's healthcare data, for example, where such healthcare providers are operating in DIL conditions.

A wearable data storage and transmission device 120 (e.g., as described herein according to various embodiments, and which may also be referred to as a "smart bandage") may be affixed to the patient 110. As described in more detail herein, the smart bandage 120 may include various components (e.g., electronic components) and may execute various modules to facilitate the collection, storage and processing of healthcare data and other information that may, for example, be associated with the patient 110. The smart bandage 120 may include one or more bandage components that may serve to cover one or more wounds and/or to absorb moisture and/or liquids, such as those excreted by the patient 110. In particular embodiments, the smart bandage 120 may serve as a healthcare data storage and processing apparatus and may perform data compression, wireless communications, and/or wired communications as described herein.

A healthcare provider or other user may operate a mobile device 130 to wirelessly communicate with the smart bandage 120. The mobile device 130 may be any type of mobile computing device that may interact with a smart bandage, such as, but not limited to, a non-smart mobile phone, a dedicated healthcare data processing device, a smart phone, a laptop computer, a tablet computer, etc. The mobile device 130 may be any type of mobile computing device that is capable of communicating with another device (e.g., the smart bandage 120) using wireless communications technology, such as NFC, Wi-Fi, Bluetooth, and/or any other short-range wireless communications technology. Using a suitable wireless communication means (e.g., near field communications (NFC), Bluetooth, Wi-Fi, any other form of short-range wireless communications, etc.), the mobile device 130 may wirelessly transmit data to and/or receive data from the smart bandage 120 via the wireless communications connection 192, as described in more detail herein. The mobile device 130 may use various data compression techniques (such as those described herein) in order to compress, transmit, and store healthcare data more efficiently on the smart bandage 120. The mobile device 130 may also, or instead, use the decompression techniques described herein with healthcare data received from the smart bandage 120 in order to process, store, and/or transmit such data.

In various embodiments, the mobile device 130 may instead, or also, transmit data to and/or receive data from the smart bandage 120 using a wired communications means, as described in more detail herein. For example, the mobile device 130 may connect to the smart bandage 120 using a cable 191 (e.g., USB cable, mini-USB cable, micro-USB cable, etc.) and exchange data via such a cable 191. In such embodiments, as with wireless embodiments, the mobile device 130 may use various data compression techniques (such as those described herein) in order to compress, transmit, and store healthcare data more efficiently on the smart bandage 120. The mobile device 130 may also, or instead, use the various decompression techniques described herein with healthcare data received from the smart bandage 120 in order to process, store, and/or transmit such data.

The mobile device 130 may be configured to communicate with one or more other devices via one or more networks 140 that may include any type of network and any combination of multiple networks. For example, the one or more networks 140 may include, but are not limited to, a wireless communications network (e.g., 3G, 4G, 5G, CDMA, etc.), a wireless local area network (WLAN) (e.g., Wi-Fi, etc.), a wired network (e.g., local area network (LAN), a wide area network (WAN), etc.), and/or any other type of communications network.

The devices and systems with which the mobile device 130 may communicate may be any of a variety of other devices or systems. Such devices may include, but are not limited to, one or more databases 150 that may store healthcare data and related data, one or more healthcare data servers 160 that may store and/or process healthcare data and related data, one or more government agency data servers 170 that may store and/or process healthcare data and related data on behalf of a government agency (e.g., Department of Defense, etc.), and any one or more other devices 180 that may store and/or process healthcare data and related data.

In particular embodiments, the mobile device 130 may also transmit to and/or receive data from (e.g., data exchanged with the smart bandage 120) one or more cloud-based storage systems 185. For example, the mobile device 130 may collect and relay data from the smart bandage 120 to a cloud-based healthcare records processing and storage system (e.g., represented as the one or more cloud-based storage systems 185) for use by any suitable users and devices at another time and/or location.

In various embodiments, the mobile device 130 may communicate with one or more other devices via the one or more networks 140 at a different time than when the mobile device 130 to communicate with the smart bandage 120. For example, a user may first use mobile device 130 to communicate with the smart bandage 120 in a DIL environment and then later upload data retrieved from the smart bandage 120 to another device when the user is in a non-DIL environment (e.g., an environment with Internet connectivity). Similarly, a user may download data from one or more various devices while operating the mobile device 130 in a non-DIL environment and later, when working with the patient 110 in a DIL environment, use such data in communication exchanges with the smart bandage 120.

Devices and systems other than mobile devices may also, or instead, be used to communicate and exchange data with the smart bandage 120. Any one or more remote devices may be used for data exchange with the smart bandage 120. In various embodiments, a healthcare provider or other user may operate a laptop computer 131 (representing any type of portable computing device) to communicate with the smart bandage 120. Such communications may be wired and/or wireless. The laptop computer 131 may be any type of portable computing device that may interact with a smart bandage, such as, but not limited to, a portable dedicated healthcare data processing device, a laptop computer, a tablet computer, etc.

In particular embodiments, the laptop computer 131 may be a portable computing device that is capable of communicating with another device (e.g., the smart bandage 120) using wireless communications technology, such as NFC, Wi-Fi, Bluetooth, and/or any other short-range wireless communications technology. Using a suitable wireless communication means (e.g., NFC, Bluetooth, Wi-Fi, any other form of short-range wireless communications, etc.), the laptop computer 131 may wirelessly transmit data to and/or receive data from the smart bandage 120 using the wireless communications connection 194, as described in more detail herein. The laptop computer 131 may use various data compression techniques (such as those described herein) in order to compress, transmit, and store healthcare data more efficiently on the smart bandage 120. The laptop computer 131 may also, or instead, use the decompression techniques described herein with healthcare data received from the smart bandage 120 in order to process, store, and/or transmit such data.

In various embodiments, the laptop computer 131 may instead, or also, transmit data to and/or receive data from the smart bandage 120 using a wired communications means, as described in more detail herein. For example, the laptop computer 131 may connect to the smart bandage 120 using a cable 193 (e.g., USB cable, micro-USB cable, etc.) and exchange data via such a cable 193. In such embodiments, as with wireless embodiments and mobile device embodiments, the laptop computer 131 may use various data compression techniques (such as those described herein) in order to compress, transmit, and store healthcare data more efficiently on the smart bandage 120. The laptop computer 131 may also, or instead, use the various decompression techniques described herein with healthcare data received from the smart bandage 120 in order to process, store, and/or transmit such data.

Like the mobile device 130, the laptop computer 131 may be configured to communicate with any one or more of a variety of other devices and systems (e.g., as described in regard to the embodiments employing the mobile device 130) via the one or more networks 140. As noted above, such devices may include, but are not limited to, one or more databases 150 that may store healthcare data and related data, one or more healthcare data servers 160 that may store and/or process healthcare data and related data, one or more government agency data servers 170 that may store and/or process healthcare data and related data on behalf of a government agency (e.g., Department of Defense, etc.), one or more cloud-based storage systems 185 (e.g., one or more cloud-based healthcare records processing and storage system), and any one or more other devices 180 that may store and/or process healthcare data and related data. The laptop computer 131 may communicate with any of such one or more other devices via the one or more networks 140 at any time (e.g., during interaction with the smart bandage 120, immediately following such interaction, or at a later time).

In various embodiments, a healthcare provider or other user may operate a non-portable computer 132 (representing any type of typically non-portable or less portable computing device) to communicate with the smart bandage 120. Here again, such communications may be wired and/or wireless. The computer 132 may be any type of portable computing device that may interact with a smart bandage, such as, but not limited to, a desktop dedicated healthcare data processing device, a server computer, a desktop computer, multiple communicatively connected computers, a rack mounted computer, etc.

In particular embodiments, the computer 132 may be a computing device that is capable of communicating with another device (e.g., the smart bandage 120) using wireless communications technology, such as NFC, Wi-Fi, Bluetooth, and/or any other short-range wireless communications technology. Using a suitable wireless communication means (e.g., NFC, Bluetooth, Wi-Fi, any other form of short-range wireless communications, etc.), the computer 132 may wirelessly transmit data to and/or receive data from the smart bandage 120 using the wireless communications connection 196, as described in more detail herein. The computer 132 may use various data compression techniques (such as those described herein) in order to compress, transmit, and store healthcare data more efficiently on the smart bandage 120. The computer 132 may also, or instead, use the decompression techniques described herein with healthcare data received from the smart bandage 120 in order to process, store, and/or transmit such data.

In various embodiments, the computer 132 may instead, or also, transmit data to and/or receive data from the smart bandage 120 using a wired communications means, as described in more detail herein. For example, the computer 132 may connect to the smart bandage 120 using a cable 195 (e.g., USB cable, micro-USB cable, etc.) and exchange data via such a cable 195. In such embodiments, as with wireless embodiments, laptop embodiments, and mobile device embodiments, the computer 132 may use various data compression techniques (such as those described herein) in order to compress, transmit, and store healthcare data more efficiently on the smart bandage 120. The computer 132 may also, or instead, use the various decompression techniques described herein with healthcare data received from the smart bandage 120 in order to process, store, and/or transmit such data.

Like the mobile device 130 and the laptop computer 131, the computer 132 may be configured to communicate with any one or more of a variety of other devices and systems (e.g., as described in regard to the embodiments employing the mobile device 130 or the laptop computer 131) via the one or more networks 140. As noted above, such devices may include, but are not limited to, one or more databases 150 that may store healthcare data and related data, one or more healthcare data servers 160 that may store and/or process healthcare data and related data, one or more government agency data servers 170 that may store and/or process healthcare data and related data on behalf of a government agency (e.g., Department of Defense, etc.), one or more cloud-based storage systems 185 (e.g., one or more cloud-based healthcare records processing and storage system), and any one or more other devices 180 that may store and/or process healthcare data and related data. The laptop computer 131 may communicate with any of such one or more other devices via the one or more networks 140 at any time (e.g., during interaction with the smart bandage 120, immediately following such interaction, or at a later time).

In various embodiments, the smart bandage 120 may communicate with one or more beacons, such as Bluetooth beacon 133, via wireless communications connection 198. The Bluetooth beacon 133 may transmit data such as a location, a date, a time, etc., that can be collected and stored by the smart bandage 120 for future use and reference, for example in contact tracing applications as described in more detail below.

Note that the various combinations of devices and communications means are illustrated in FIG. 1 to provide a complete description of contemplated embodiments. Any subset of such devices and communications means are contemplated as within the scope of the disclosed embodiments. For example, in particular embodiments, any one of the exemplary devices 130, 131, and 132 may exchange any type of data with the smart bandage 120 using (e.g., solely) wired or wireless communications means. In other examples, in particular embodiments, multiple such devices may communicate with the smart bandage 120 using either or both wired and wireless communications means.

In various embodiments, the system may provide data collected and stored by its components for integration into long term and/or longitudinal record for a particular user. For example, the system may collect data on a soldier during a deployment (and perhaps during the treatment for an injury). This data may be periodically collected from the system and provided to a healthcare records processing and storage system (e.g., that may be a cloud-based system) for integration with that soldier's existing healthcare records. In this way, the healthcare information generated while the soldier was deployed will retained and included in the soldiers permanent healthcare records so that better medical treatment may be provided based on complete information. This will also allow for improved planning and preparation as such records would be more current and available for decisions involving the soldier and his or her organization. The healthcare data for individual soldiers can also be aggregated to determine a more general state of health of particular organizational units to further facilitate planning and preparation. Deployments, logistics, asset movements, and other preparations may be adjusted on a real-time basis using up-to-date healthcare information by using the disclosed embodiments.

In various embodiments, rather than use as a bandage or other apparatus affixed to a human user, the disclosed embodiments may be used to store and transport data for any item for which up-to-date and/or detailed information is important. For example, in particular embodiments, the system may be used to receive, store, transport, and transmit information regarding the source and storage conditions of biological material while be affixed (e.g., proximate) to such material. For example, the system may include an adhesive sticker with housing components that are configured to store information regarding blood supplies to which the system is attached (e.g., blood type, date collected, tests performed on the blood, etc.). The system may be used with other biological material, such as organs, platelets, plasma, medications, etc. The system may also be used with other non-biological material for which up-to-date and/or detailed information is important, such as munitions, food, mechanical parts, etc. For example, the system may be used to store details on the manufacture, maintenance, and lifespan of particular engine parts or munitions components. One skilled in the art will recognize the many situations in which the disclosed systems may be of value.

Exemplary Computer Architecture

Figure 2:
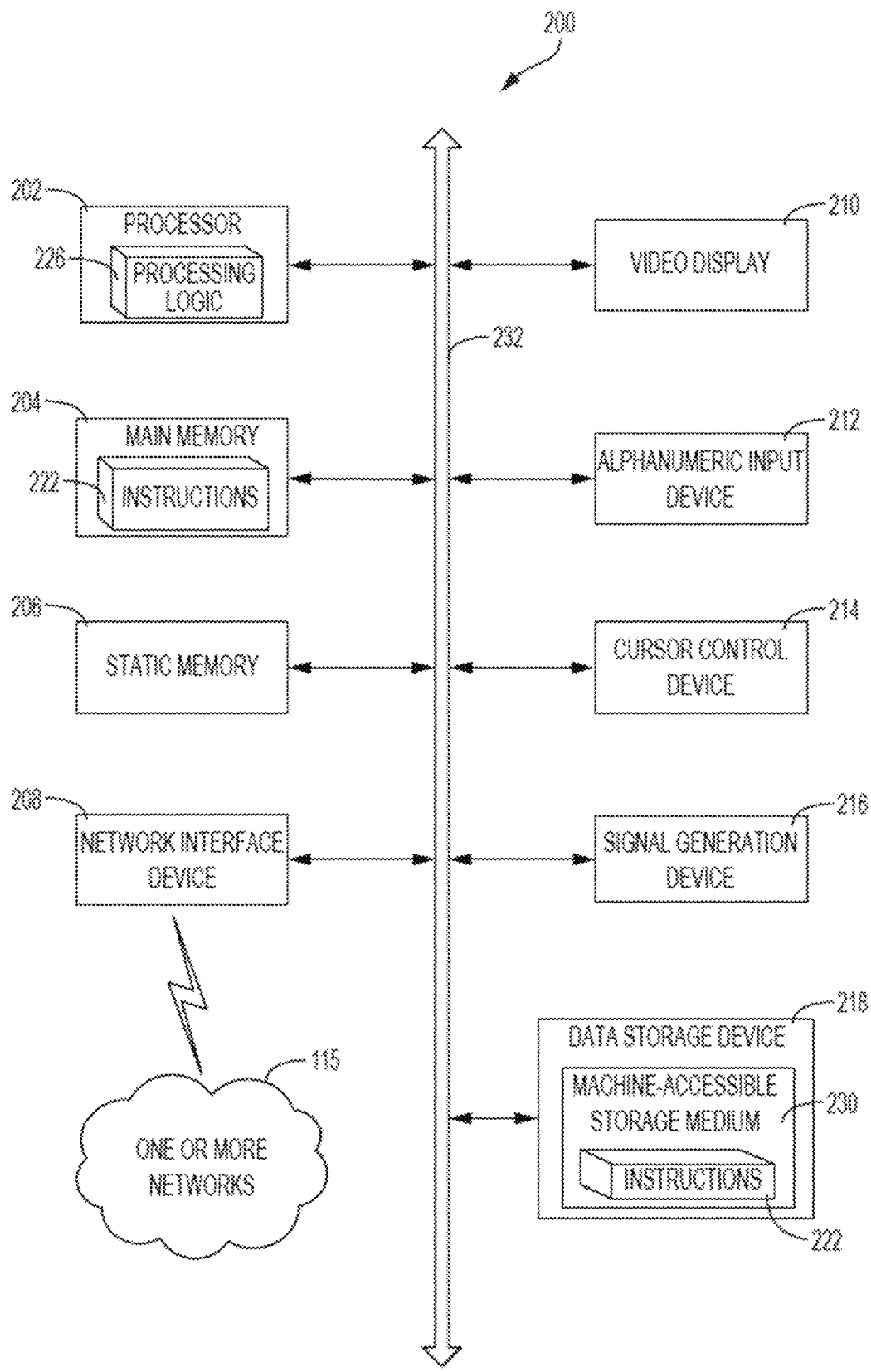
FIG. 2 is a diagram illustrating an exemplary computer that may be used in one or more exemplary system in which various embodiments may be implemented, such as exemplary system 100 of FIG. 1.

FIG. 2 illustrates a diagrammatic representation of a computer architecture of a computer 200 that may be used within a bandage, sticker, band, or other similar device for storing and transmitting large amounts of data and to implement structured and configurable data compression, for example, as described herein. In particular embodiments, the computer 200 may be suitable for use as a computer disposed within a bandage, sticker, or band as described herein that is configured to receive input from a device, sensors, etc. and store, process, and transmit such data.

In particular embodiments, the computer 200 may be connected (e.g., networked) to one or more other computers using Bluetooth, NFC, another form of short-range wireless communications, and/or other wireless communications technologies. The computer 200 may also, or instead, be communicatively connected to one or more other computers using a physical connection and/or cable (e.g., USB, mini-USB, micro-USB, standard USB of any type, etc.). The computer 200 may also, or instead, connect to other computers using a LAN, an intranet, an extranet, and/or the Internet (e.g., using any wired and/or wireless communications connection). The computer 200 may be, or may be based on, any type of device having one or more processors and data storage capabilities and capable of executing a set of instructions (sequential or otherwise) that specify actions to be taken by that computer. Further, while only a single computer is illustrated, the term "computer" shall also be taken to include any collection of computers that individually or jointly execute a set (or multiple sets) of instructions to perform any one or more of the methodologies discussed herein, such as the data compression and/or decompression methods described in more detail below.

The computer 200 may include a processing device 202 (e.g., one or more computer processors) and a main memory 204 (e.g., read-only memory (ROM), random access memory (RAM), flash memory, dynamic random-access memory (DRAM) such as synchronous DRAM (SDRAM) or Rambus DRAM (RDRAM), etc.) storing instructions 222 that may be executed by the processor 202. The computer 200 may also include a static memory 206 (e.g., flash memory, static random-access memory (SRAM), etc.) and a data storage device 218. All such components of the computer 200 may communicate with each other via a bus 232.

The processor 202 represents one or more general-purpose processing devices such as a microprocessor, a central processing unit, and the like. More particularly, each processing device of the processor 202 may be a complex instruction set computing (CISC) microprocessor, reduced instruction set computing (RISC) microprocessor, very long instruction word (VLIW) microprocessor, Scalar Board, a processor implementing other instruction sets, or a processor implementing a combination of instruction sets. Each processing device of the processor 202 may also, or instead, be one or more special-purpose processing devices such as an application specific integrated circuit (ASIC), a field programmable gate array (FPGA), a digital signal processor (DSP), a network processor, and the like. The processor 202 may be configured to execute processing logic 226 for performing various operations and steps discussed herein.

The computer 200 may further include a network interface device 208 that may include one or more NFC components, Bluetooth components, any other type of short-range wireless communications components, and/or any other wireless communications components that may allow communication directly with any other device (e.g., a smart bandage) and/or via any type of network. The network interface device 208 may also, or instead, include one or more wired communications components that may facilitate wired communications via a physical connection to one or more other devices (e.g., USB, mini-USB, micro-USB, standard USB of any type, etc.). The computer 200 also may include a video display unit 210 (e.g., a flexible computer display, a liquid crystal display (LCD), an LED display, or any other suitable display), an alphanumeric or other type of input device 212 (e.g., a keyboard, a touchscreen, etc.), a cursor control or other input device 214 (e.g., touch-sensitive input device, or other suitable input device, etc.), and a signal generation device 216 (e.g., a speaker).

The data storage device 218 may include a non-transitory computer-accessible storage medium 230 (also known as a non-transitory computer-readable storage medium or a non-transitory computer-readable medium) on which may be stored one or more sets of instructions (e.g., software 222) embodying any one or more of the methodologies or functions described herein. The software 222 may also reside, completely or at least partially, within the main memory 204 and/or within the processor 202 during execution thereof by the computer 200. The main memory 204 and the processing device 202 may also constitute computer-accessible storage media. The software 222 may further be transmitted or received directly from another device and/or over a network (e.g., one or more networks 140) via the network interface device 208.

While the computer-accessible storage medium 230 is shown in an exemplary embodiment to be a single medium, the terms "computer-accessible storage medium," "computer-readable storage medium," and "computer-readable medium" should be understood to include a single medium or multiple media (e.g., a centralized or distributed database and/or associated caches and servers) that store the one or more sets of instructions. The terms "computer-accessible storage medium," "computer-readable storage medium," and "computer-readable medium" should also be understood to include any medium that is capable of storing, encoding, or carrying a set of instructions for execution by the computer and that cause the computer to perform any one or more of the methodologies of the present invention. The terms "computer-accessible storage medium," "computer-readable storage medium," and "computer-readable medium" should accordingly be understood to include, but not be limited to, solid-state memories, optical media, magnetic media, etc.

Also, while the computer 200 is shown in FIG. 2 as including various components, it should be understood that the computer 200 may include greater or fewer components in other embodiments. For example, in certain embodiments 200, the computer may not include a video display 210, signal generation device 216, or other components shown in FIG. 2.

Smart Bandage Overview

In most modern industries and businesses, storing and transmitting large amounts of data using computing devices and networks is common. The healthcare industry is no exception and the use of modern computing devices and networks has greatly increased the efficacy of modern healthcare. However, situations may arise where the communication of healthcare data beyond the immediate area is much more limited or even impossible, such as in "disconnection, intermittent, or low-bandwidth" (DIL) environments (e.g., battlefields, remote operations, temporary hospitals, emergency facilities, in natural disasters, any other situations where the normal infrastructure has been rendered inoperable, etc.). In such situations, the need to collect, store, and exchange healthcare information remains. To accommodate data storage needs in such difficult environments, the various disclosed embodiments provide for a device that can store and transmit large amounts of data quickly and securely, especially to support situations where direct device to device transmission is limited or (e.g., practically) impossible.

In DIL situations, healthcare providers may be operating in a temporary medical facility (e.g., in an operational battlefield, in a temporary medical facility set up to address a pandemic, in a temporary medical facility set up to address a natural disaster, etc.). In such environments, healthcare providers may need to treat patients at the point of injury and/or at the location where they experienced an onset of illness (e.g., wounded soldiers in the battlefield, victims of natural disaster proximate to the impact of the disaster, victims of disease (e.g., viral and/or bacterial infection) at the location of symptom onset, etc.). Often in these scenarios, the healthcare providers and others are operating in forward deployed situations where there is little or no access to high-speed communications technologies.

Various embodiments provide specialized solutions that allow a healthcare provider operating in such DIL environments to digitally capture medical information on a mobile device and document the care of an injured or ill patient. In various embodiments, the healthcare provider may convey the medical information physically along with the patient as the patient moves from the forward operating environment to a brick-and-mortar hospital or other, more permanent, medical facility. Various disclosed systems and methods provide for a device that is easy to use, can be affixed to, and move with, the patient, and can carry sufficient amounts of data (e.g., pictures, video, medical records, recordings, etc.) to improve the information available about the care received by the patient and prevent important medical data from lagging behind the patient.

In various embodiments, the disclosed apparatus may be used in DIL environments and may be configured to be affixed to a patient. In particular embodiments, the disclosed apparatus may serve at least one other purpose, such as also functioning as a bandage. Various embodiments may be configured to store relatively large amounts of data and to transmit, receive, read, and/or present such data as the patient moves along various points in the path of care, for example, from point of injury to a hospital or other care location. While various embodiments set forth herein may be described using examples related to providing medical care to an injured or ill patient in a DIL environment, various embodiments of the disclosed systems and methods may be implemented in any suitable situations and environments, and implemented in any suitable systems and configurations, such as, but not limited to, equipment tags, engine maintenance tags, medical products, and/or any other devices and systems that may electronically store maintenance records and/or a history of how an associated item has been handled. Various embodiments of the disclosed systems and methods may allow a record associated with an item to be affixed to, and travel with, the item itself without requiring the use of a centralized database or network communications to retrieve the information in such a record.

Smart Bandage System and Apparatus

Figure 3:
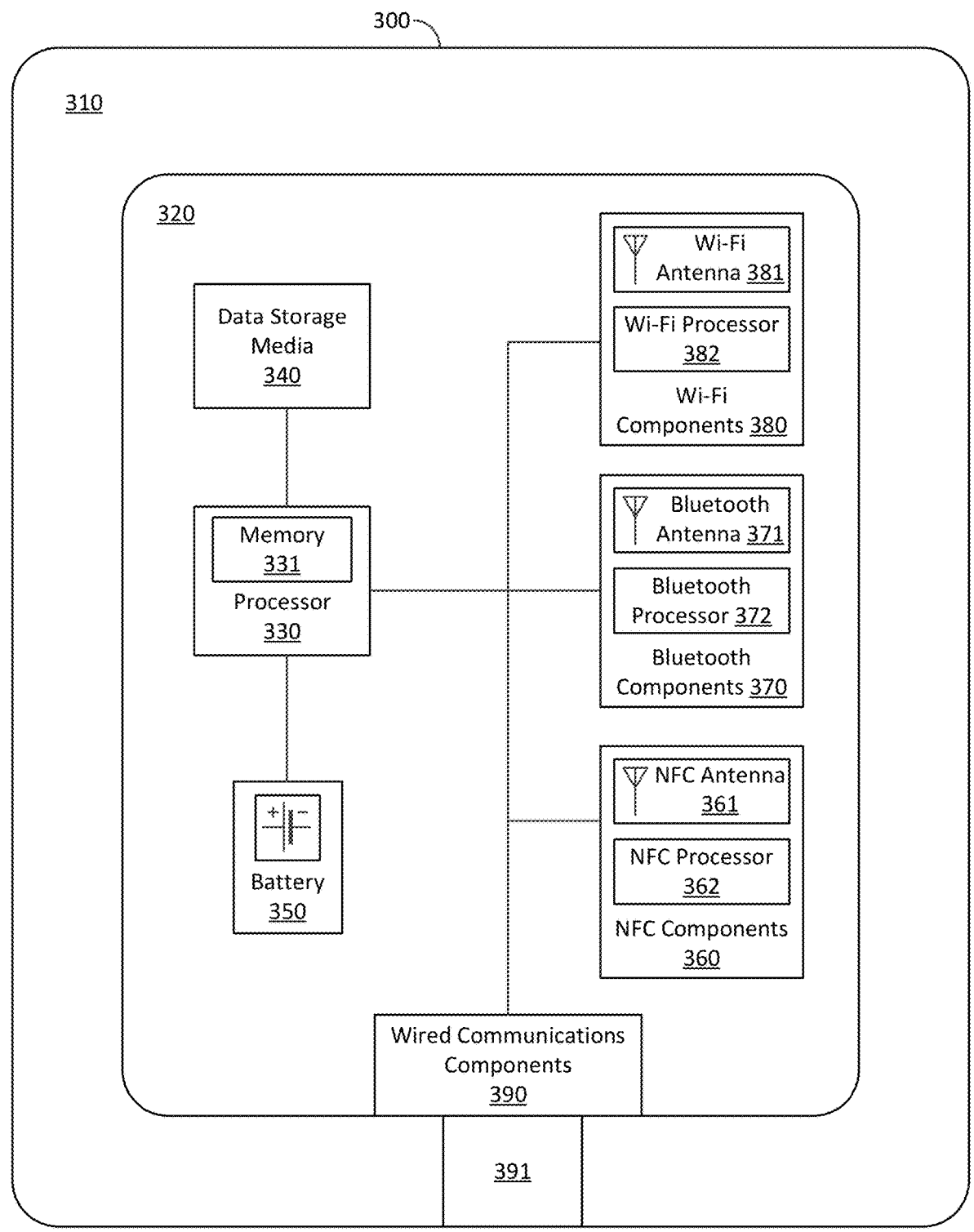
FIG. 3 is a diagram illustrating an exemplary wearable storage and transmission device in which various embodiments may be implemented.

FIG. 3 illustrates a block diagram representing an exemplary wearable data storage and transmission device (also referred to herein as a "smart bandage") 300. Note that, while the embodiments described herein may be referred to for explanatory purposes as a "bandage," various embodiments may take the form of a bandage, sticker, tag, label, band (e.g., wrist band, ankle band, leg band, etc.), any other type of wearable data storage and transmission device, and/or any other device, system, or apparatus that may be configured according to one or more of the disclosed embodiments. In various embodiments, the wearable data storage and transmission device 300 may be configured to encapsulate the various electronic components of the system (e.g., components to transmit, receive, and/or store data) and the connections therebetween. In particular embodiments, the wearable data storage and transmission device 300 may be implemented as a bandage that may be used in an operational battlefield environment or other DIL environment to carry patient data while physically attached to the patient. The wearable data storage and transmission device 300 may have a size of about 2×2 inches, 4×4 inches, or any other suitable size. In a particular embodiment, the wearable data storage and transmission device may have the dimensions of 2.75 inches×2.1 inches×0.355 inches and weigh approximately 40 grams. The wearable data storage and transmission device 300 may include typical bandage and/or sticker components, such as an adhesive section 310 that may be configured to adhere to a patient or some other object. In particular embodiments where the wearable data storage and transmission device 300 serves as a bandage, the component housing section 320 may be configured with absorbent material designed to absorb liquids that may emanate from a wound or sore. Alternatively, the adhesive section 310 may include absorbent material designed to absorb liquids that may emanate from a wound or sore.

The component housing section 320 may encapsulate, according to particular embodiments, various electronic components described below in a waterproof or water-resistant housing. The component housing section 320, including any waterproof or water-resistant housing encompassing one or more electronic components, may be flexible and allow for the use of the smart bandage 300 as a wound dressing. In alterative embodiments, one or more of the various electronic components may be disposed on the outside of the bandage. In particular embodiments, the component housing section 320 may be removably affixed to the adhesive section 310 so that the adhesive section 310 may be discarded while the component housing section 320 (and the component housed therein) may be durable and may be re-used. For example, where the smart bandage 300 is used to dress a wound, the adhesive section 310 and any accompanying absorbent material may be periodically removed and discarded as they become soiled from absorbing fluids from the wound. The component housing section 320 may be retained and inserted or otherwise affixed to a new adhesive section 310. This allows for the reuse of the components housed in the component housing section 320, and therefore the retention of any data stored therein, while enabling the proper treatment of a wound.

In a particular embodiment, the component housing section 320 may be issued to a user (e.g., a soldier) and initialized with data associated with that user, for example, prior to a deployment. The user may simply carry the component housing section 320 with them as they perform their duties. If the user becomes injured, the component housing section 320 may then be affixed or inserted into an adhesive section 310 that may be used to treat the user's injuries. Alternatively, the user may wear the component housing section 320 with an affixed adhesive section 310 despite having no injury, for example, simply to ensure that the component housing section 320 and its components and data are always with the user. Regardless of whether the user ends up using the component housing section 320 with an adhesive section 310, data on components of the component housing section 320 may be periodically updated, for example, during routine medical exams, thereby generating a healthcare record for the user regardless of health condition.

As a particular example, the electronic components enclosed in the section 320 may be embedded into the bandage such that the smart bandage 300 may have dual utility to a field medic in that the smart bandage 300 may serve as a bandage for covering one or more wounds and also provide the capability of transmitting and storing patient medical data. In particular embodiments where the smart bandage 300 is used as a bandage, the smart bandage 300 may receive patient medical data from a mobile device operated by a first healthcare provider, store the patient medical data, and transmit the patient medical data to a mobile device operated by a second healthcare provider. By using the smart bandage 300 as a bandage, a healthcare provider may not need to use multiple bandages for a patient or use a separate device to move patient medical data with the patient from one point of care to another (e.g., from the point of injury to the hospital). Various embodiments may also reduce the training that may otherwise be needed in the operation of a separate patient medical data capture device (e.g., if patient medical capture was performed using a device that was separate from a bandage and/or dedicated to patient medical data capture). In various non-medical embodiments, encapsulating the components of the disclosed systems in a sticker or bandage may facilitate the use of the system in other contexts by allowing the disclosed embodiments to be affixed to various items, devices, equipment, etc. and thereby enabling the system to easily travel with the object to which the system is affixed. In various embodiments, the components of the disclosed systems may be encapsulated in a band that may be worn by a human or animal in a medical or non-medical context, for example, worn around the wrist, ankle, leg, or arm of a wearer of such a band.

In various embodiments, the smart bandage 300 (or other wearable smart device) includes a processor 330 that may be communicatively connected to one or more of the other components within the component housing section 320. In particular embodiments, the processor 330 may be coupled to, or otherwise include, a memory 331 of any suitable type. The system may include operating system software embedded on the processor 330 (e.g., stored in the memory 331 of the processor 330). For data storage, the smart bandage 300 may be configured with a data storage media 340 as described herein. The data storage media 340 may be any type of data storage media suitable for storing relatively large amounts of data, such as healthcare data (e.g., a solid-state storage media device of any type). The smart bandage 300 may also be configured with a battery 350 for providing power to the processor 330. The battery 350 may be any suitable portable power supply capable of providing power to the electrical components of the smart bandage 300. The battery 350 may provide power to the other electrical components of the smart bandage 300, either directly or via the processor 330.

In various embodiments, the smart bandage 300 may comprise one or more NFC components 360 that may include one or more of an NFC antenna 361 and/or an NFC processing chip 362. The NFC components 360 may be communicatively connected to the processor 330. While the NFC components 360 may receive power wirelessly from an external mobile device (e.g., as in a typical NFC operation), the NFC components 360 may also, or instead, draw power from the battery 350 directly or via the processor 330.

In various embodiments, the smart bandage 300 may also, or instead, be configured with one or more Bluetooth communications components 370 that may include one or more of a Bluetooth antenna 371 and/or a Bluetooth processing chip 372. The Bluetooth components 370 may be communicatively connected to the processor 330. The Bluetooth components 370 may draw power from the battery 350 directly or via the processor 330. In particular embodiments, the Bluetooth components 370 may also, or instead, receive power wirelessly (e.g., similar to NFC components).

In various embodiments, the smart bandage 300 may be configured to communicate using IEEE 802.11 wireless technologies and/or Wi-Fi Alliance technologies, commonly referred to as "Wi-Fi." In such embodiments, the smart bandage 300 may also, or instead, be configured with one or more Wi-Fi communications components 380 that may include one or more of a Wi-Fi antenna 381 and a Wi-Fi processing chip 382. The Wi-Fi components 380 may be communicatively connected to the processor 330. The Wi-Fi components 380 may draw power from the battery 350 directly or via the processor 330. In particular embodiments, the Wi-Fi components 380 may also, or instead, receive power wirelessly (e.g., similar to NFC components).

In various embodiments, the smart bandage 300 may also, or instead, be configured with one or more other types of wireless communications components that may include any suitable one or more wireless communications antennas and wireless communications processors. Such one or more wireless communications may be communicatively connected to the processor 330. These wireless communications components may draw power from the battery 350 directly or via the processor 330. In particular embodiments, these wireless communications components may also, or instead, receive power wirelessly (e.g., similar to NFC components).

In various embodiments, the smart bandage 300 may serve as an improved type of NFC tag that has much greater storage and communications capabilities for processing information, such as, but not limited to, healthcare information. The smart bandage 300 may integrate NFC capabilities while addressing the limitations of typical NFC devices, such as limited storage space and communications capabilities. In various embodiments, the smart bandage 300 utilizes the NFC components 360 to establish one or more communication channels with at least one other device (e.g., a mobile phone, a laptop, a tablet computer, etc.) to transmit and receive data (e.g., healthcare data) that can be stored on the system itself.

In various embodiments, the smart bandage 300 may comprise one or more wired communications components 390 that may include one or more ports 391 that may facilitate a physical communications connection to one or more other devices (e.g., a USB port, a mini-USB port, a micro-USB port, a standard USB port of any type, etc.). The wired communications components 390 may include a communications processor and/or may relay signals received via the port 391 to the processors 330 for processing. The wired communications components 390 may be communicatively connected to the processor 330. The wired communications components 390 may receive power via the port 391 and a physical connection to another device configured to supply such power. The wired communications components 390 may provide power received via the port 391 to the battery 350 for charging. Alternatively, or in addition, the wired communications components 390 may draw power from the battery 350 directly or via the processor 330.

NFC Antenna and Processing Chip as On/Off Switch in a Smart Bandage

Typical NFC tags and devices derive their power from a field generated between an initiator device (e.g., a smartphone) and the NFC device. Via this field, a small NFC chip within the NFC device receives instructions to transmit its small data payload to the initiator device and/or receive data from the initiator device. The power available to typical NFC devices may be quite small because the generated field is their sole source of power. Therefore, the amount of processing that such devices may perform may be very limited.

In various embodiments, the processor 330 of the smart bandage 300 is capable of running much more complex algorithms than a typical NFC device and has access to the much larger data storage capacity of the data storage media 340 as well as its own memory 331. This is due, at least in part, to the processor 330 being coupled to an independent, stand-alone power supply, the battery 350. While the battery 350 may supply power to any of the electronic components of the smart bandage 300, in various embodiments the battery 350 may be configured to not power the components of the smart bandage 300 continuously in order to minimize the use of power by the smart bandage 300. This may enable longer term access and storage of information so that such information is accessible to other devices for a sustained amount of time.

In various embodiments, the system may use the NFC components 360, and particularly the NFC antenna 361, as an on/off switch for the internal power supply of the smart bandage 300 (e.g., the battery 350). The smart bandage 300 may receive a signal from an NFC initiator device (e.g., a smartphone, a laptop computer, a tablet computer, etc.) via the NFC antenna 361 and may, in response to detecting the signal at the NFC antenna 361, establish an NFC field with NFC initiator device using the NFC components 360. In response to establishing this NFC field, the NFC components 360 may transmit a signal to the processor 330 instructing the processor 330 to "turn on" and/or "boot up." The processor 330 may activate the battery 350 to supply greater, continuous power to the processor 330 and to the other components of the smart bandage 300. In response to establishing this NFC field, the NFC components 360 may also, or instead, transmit a signal directly to the battery 350 instructing the battery 350 to turn on and thereby send power to the processor 330 that causes the processor 330 to boot up. The processor 330 in conjunction with the battery 350 may then supply greater, continuous power to the other components of the smart bandage 300.

After activating using the power supplied by the battery 350, the processor and other components of the smart bandage 300 may then stay powered for as long as the initiator device maintains contact with the NFC components 360. While in contact with the initiator device, the smart bandage 300 may exchange data using NFC, but process and/or otherwise handle the data using the processor 330 and the other components of the smart bandage 300. For example, the smart bandage 300 may receive data for storage from the initiator device via NFC using the NFC components 360, process the data using the processor 330, and store the processed data on the data storage media 340. Similarly, the smart bandage 300 may receive an instruction to provide stored data from the initiator device via NFC and, in response, may retrieve the data from the data storage media 340, process the data as needed at the processor 330, and transmit the data to the initiator device via NFC using the NFC components 360.

In various embodiments, in response to the initiator device being removed and/or the NFC field being broken between the initiator device and the smart bandage 300, the NFC processor 362 may automatically power down the processor and any other powered components of the smart bandage 300, or otherwise instruct such components to power down, thereby conserving battery power.

Using Bluetooth Components in Conjunction with NFC Components in a Smart Bandage In various embodiments, the smart bandage 300 may include one or more Bluetooth components 370 that may include one or more of a Bluetooth antenna 371 and/or Bluetooth processor 372. The Bluetooth components 370 may use any suitable version and/or specification of Bluetooth. In particular embodiments, the Bluetooth components 370 use Bluetooth Low Energy (BT LE) and Bluetooth Specification 5.0 or later. By using the Bluetooth components 370 in conjunction with the NFC components 360, the smart bandage 300 may achieve higher transfer speeds and/or may not require a continuous NFC field maintained by an NFC initiator device for operation.

In various embodiments, NFC may be used to "wakeup" the smart bandage 300 as described above, when an NFC initiator device establishes an NFC field with the NFC components 360 of the smart bandage 300. In response to the smart bandage 300 detecting the NFC initiator device, the NFC components 360 boot the processor 330 and power the data storage media 340 and the Bluetooth components 370, enabling the Bluetooth components 370 to transmit and receive data. The NFC components 360 may then transmit a specialized NFC Data Exchange Format (NDEF) message to the initiator device that indicates that the smart bandage 300 has Bluetooth capabilities and can use BT LE to transfer data instead of using NFC. This specialized message may include a BT LE device address associated with the Bluetooth components 370. If the initiator device is Bluetooth enabled, it can use the BT LE address transmitted by the smart bandage 300 to "bond" to the Bluetooth components 370. Using a customized handshake of proprietary commands, the initiator device may inform the smart bandage 300 via Bluetooth that the initiator device wants to read data from the smart bandage 300 and/or inform the smart bandage 300 via Bluetooth that the initiator device wants to write data to the smart bandage 300.

If the initiator device is in read mode (e.g., has instructed the smart bandage 300 to transmit stored data), the smart bandage 300 may retrieve data from the data storage media 340 and transmit the retrieved data to the initiator device using the Bluetooth generic attribute (GATT) profile via the Bluetooth components 370. When the smart bandage 300 completes sending the requested data using the Bluetooth components 370, the smart bandage 300 may transmit a termination command (e.g., a proprietary command) to the initiator device via the Bluetooth components 370 to inform the initiator device that all requested data has been sent.

If the initiator device is in write mode (e.g., has instructed the smart bandage 300 to receive and store data), the initiator device will transmit the data to the smart bandage 300 via Bluetooth and the smart bandage 300 will receive the data using the Bluetooth components 370. The smart bandage 300 will process the received data as needed and store the received data in the data storage media 340. When the initiator device has completed transmitting the data to be stored to the smart bandage 300, the initiator device will transmit an end-of-transmission command to the smart bandage 300.

When the interaction (e.g., read or write) with the initiator device via Bluetooth is complete, the BT LE bond may be broken. In response to the breaking of this bond, the Bluetooth components 370 may be configured to return the smart bandage 300 to a "sleep" or low power mode by instructing the processor 330 and any other powered components of the smart bandage 300 to power down, thereby conserving the power stored by the battery 350.

In various embodiments, upon activation following an NFC initiation, the Bluetooth components 370 may transmit a Bluetooth code allowing the smart bandage 300 to be detected by other Bluetooth-capable devices. A user may enable Bluetooth scanning on an external device (e.g., a laptop, smartphone, etc., that may or may not be the same device as the initiator device) and detect the smart bandage 300's Bluetooth code. The user may then select that code and establish a Bluetooth communications session with the smart bandage 300 to exchange data, for example, using point-to-point Bluetooth data transfer.

Using Wi-Fi Components in Conjunction with NFC Components in a Smart Bandage

In various embodiments, the smart bandage 300 may include one or more Wi-Fi components 380 that may include one or more of a Wi-Fi antenna 381 and/or Wi-Fi processor 382. The Wi-Fi components 380 may use any suitable version and specification of any wireless communications technology, such as IEEE 802.11. By using the Wi-Fi components 380 in conjunction with the NFC components 360, the smart bandage 300 may achieve higher transfer speeds and/or may not require a continuous NFC field maintained by an NFC initiator device for operation.

In various embodiments, NFC may be used to "wakeup" the smart bandage 300 as described above, in response to an NFC initiator device establishing an NFC field with the NFC components 360 of the smart bandage 300. When the smart bandage 300 detects the NFC initiator device, the NFC components 360 boot the processor 330 and power the data storage media 340 and the Wi-Fi components 380, enabling the Wi-Fi components 380 to transmit and receive data. The NFC components 360 may then transmit a specialized NFC Data Exchange Format (NDEF) message to the initiator device that indicates that the smart bandage 300 has Wi-Fi capabilities and can use Wi-Fi to transfer data instead of using NFC. This specialized message may include a device MAC address associated with the one or more Wi-Fi components 380. If the initiator device is Wi-Fi enabled, it can use the MAC address associated with the Wi-Fi components 380 transmitted by the smart bandage 300 (e.g., directly or via a Wi-Fi router) to establish an Internet Protocol (IP) communications session with the smart bandage 300 using the Wi-Fi components 380. The initiator device may inform the smart bandage 300 via this communications session that the initiator device wants to read data from the smart bandage 300 and/or inform the smart bandage 300 via this communications session that the initiator device wants to write data to the smart bandage 300.

In various embodiments, following activation after an NFC initiation, a user may enable Wi-Fi scanning on an external device (e.g., a laptop, smartphone, etc., that may or may not be the same device as the initiator device) and detect the smart bandage 300. The user may then select the smart bandage 300 as a device with which to establish a point-to-point Wi-Fi connection that can then be used to exchange data. Alternatively, the smart bandage 300 may establish a Wi-Fi connection via one or more intermediary devices, such as one or more Wi-Fi hubs, routers, and switches.

If the initiator device is in read mode (e.g., has instructed the smart bandage 300 to transmit stored data), the smart bandage 300 may retrieve data from the data storage media 340 and transmit the retrieved data to the initiator device using the Wi-Fi components 380. When the smart bandage 300 completes sending the requested data using the Wi-Fi components 380, the smart bandage 300 may terminate the communications session via the Wi-Fi components 380 and/or inform the initiator device that all requested data has been sent.

If the initiator device is in write mode (e.g., has instructed the smart bandage 300 to receive and store data), the initiator device will transmit the data to the smart bandage 300 via the IP communications session and the smart bandage 300 will receive the data using the Wi-Fi components 380. The smart bandage 300 will process the received data as needed and store the received data in the data storage media 340. When the initiator device has completed transmitting the data to be stored to the smart bandage 300, the initiator device may terminate the communications session and/or inform the smart bandage 300 that all data has been sent.

As noted above, in response to determining that the interaction (e.g., read or write) with the initiator device via Wi-Fi is complete, the system may terminate the communications session. In response to the termination of the communications session using Wi-Fi, the Wi-Fi components 380 may be configured to return the smart bandage 300 to a "sleep" or low power mode by instructing the processor 330 and any other powered components of the smart bandage 300 to power down, thereby conserving the power stored by the battery 350. In particular embodiments, in response to detecting the breaking of the NFC bond with the NFC initiator device, the NFC components 360 may transmit a deactivation signal to the processor 330, which may, in response, transmit a signal to the Wi-Fi components 380 to terminate the Wi-Fi communications session and then power down.

In particular embodiments, any of the described wireless and wired communications technologies may be used in combination with short-range wireless communications technologies other than NFC. For example, one or more short-range wireless communications components (e.g., one or more non-NFC short-range wireless communications components) may establish a short-range wireless communications session (e.g., a non-NFC short-range wireless communications session) with one or more remote computing devices. In response to establishing this communications session, the one or more short-range wireless communications components may transmit an activation signal to one or more Wi-Fi and/or Bluetooth components. In response to the termination of this communications session, the one or more short-range wireless communications components may transmit a deactivation signal to the one or more Wi-Fi and/or Bluetooth components. The system may perform these and other aspects described herein using any alternative, non-NFC short-range wireless communications technology.

Wired Communications Components as on/Off Switch in a Smart Bandage

As noted above, the battery 350 may supply power to any of the electronic components of the smart bandage 300, but may be configured to not power the components of the smart bandage 300 continuously in order to minimize the use of power by the smart bandage 300, enabling longer term access and storage of information so that such information is accessible to other devices for a sustained amount of time. In various embodiments, the system may use the wired communications components 390 in combination with the port 391 as an on/off switch for the internal power supply of the smart bandage 300 (e.g., the battery 350). The wired communications components 390 of the smart bandage 300 may detect a signal and/or power received via the port 391 and may, in response to detecting the power and/or signal (e.g., voltage, amperage, current, etc.), transmit a signal to the processor 330 instructing the processor 330 to "turn on" and/or "boot up." The processor 330 may activate the battery 350 to supply greater, continuous power to the processor 330 and to the other components of the smart bandage 300. In response to detecting the power and/or signal, the wired communications components 390 may also, or instead, transmit a signal directly to the battery 350 instructing the battery 350 to turn on and thereby send power to the processor 330 that causes the processor 330 to boot up. The processor 330 in conjunction with the battery 350 may then supply greater, continuous power to the other components of the smart bandage 300. Alternatively, or in addition, the components of the smart bandage 300 may draw power for operation from the external device using the wired communications components 390 in combination with the port 391 instead of drawing power from the battery 350, thereby saving power stored in the battery 350. The mart bandage may also be configured to charge the battery 350 using power received from the wired communications components 390 in combination with the port 391.

After activating using the power supplied by the battery 350, the processor and other components of the smart bandage 300 may then stay powered for as long as a signal and/or power is detected at the wired communications components 390 via the port 391. While in contact with an external device via the port 391 and the wired communications components 390, the smart bandage 300 may exchange data with the external device using the wired communications components 390 in combination with the port 391. The smart bandage 300 may process and/or otherwise handle such data using the processor 330 and the other components of the smart bandage 300. For example, the smart bandage 300 may receive data for storage from the external device via the wired communications components 390 and the port 391, process the data using the processor 330, and store the processed data on the data storage media 340. Similarly, the smart bandage 300 may receive an instruction to provide stored data from the external device via the port 391 and, in response, may retrieve the data from the data storage media 340, process the data as needed at the processor 330, and transmit the data to the external device via the port 391 using the wired communications components 390.

In various embodiments, in response to the external device ceasing communications with the smart bandage via the port 391 and the wired communications components 390 (e.g., the signal and/or power received from the external device is no longer detected by the wired communications components 390), the wired communications components 390 may automatically power down the processor and any other powered components of the smart bandage 300, or otherwise instruct such components to power down, thereby conserving battery power.

Note that any of the aspects of the various embodiments described herein may be used in combination. For example, the smart bandage may be powered up in response to detecting a signal at the physical port 391, but may then set up a Bluetooth communications session or a Wi-Fi communications session that is used to exchange data with an external device. Any other combination can be used in various particular embodiments.

Transmitting and Receiving Large Amounts of Data Using NFC on a Smart Bandage

As noted herein, current NFC devices are very limited in the amount of data they can store, largely due to the limited power available to such devices due to using an NFC field as a power source. In various embodiments, by using an on-board power supply such as the battery 350, a processor such as the processor 330, and storage components such as the data storage media 340, the disclosed embodiments may provide much greater data storage capacity. To further increase the data storage capabilities of the disclosed embodiments, the smart bandage 300 may use one or more methods and/or algorithms based on current NFC technology that allow the smart bandage 300 to emulate a standard Type2 NFC tag. By using such tag emulation, the processor 330 may be able to communicate, via the NFC components 360, with an initiator device to send and/or receive data using "chunks" that are constrained by the limitations and data transfer speeds of NFC technology. The processor 330 may use this method to continually receive and/or transmit data via these chunks between the smart bandage 300 and the initiator device until all required data is sent and/or received.

While the smart bandage 300 is writing data to the data storage media 340 (e.g., receiving data from the initiator device and storing the data to the data storage media 340), the smart bandage 300 may use the processor 330 and a chunking algorithm to write data to the data storage media 340, saving each chunk as it is successfully received. The processor 330 may monitor the storage of such data at the data storage media 340 for success or failure and transmit the appropriate NFC commands back to the initiator device to confirm whether the data has been written successfully or not.

While the smart bandage 300 is reading data from the data storage media 340 (e.g., retrieving data from the data storage media 340 and transmitting the retrieved data to the initiator device), the smart bandage 300 may use the processor 330 and a chunking algorithm to read data from the data storage media 340 and transmit that data using a maximum data chunk size and the current NFC transmission capabilities to the initiator device. The processor 330 may monitor the success or failure of this data transfer process and may transmit the appropriate NFC commands back to the initiator device to confirm whether the data has been retrieved and transmitted successfully or not.

Security and Encryption of Data Stored on a Smart Bandage

Current NFC technology uses NFC tags that lack the ability to encrypt data (e.g., on the fly) and therefore any device capable of activating a current NFC device can read the data stored on the NFC device. However, the smart bandage 300, because it includes the processor 330, the data storage media 340, and the on-board power supply battery 350, may programmatically encrypt data, for example as it is received, processed, and/or transmitted. Therefore, the disclosed embodiments may be configured for specific users (e.g., customers, government, military, etc.) with unique encryption keys that may limit the ability of any device to read data from the smart bandage 300 without the appropriate keys or exchange of information. For example, should the smart bandage 300 be lost or stolen and end up in the hands of unauthorized users (e.g., enemy combatants, criminals) such unauthorized users would not be able to read data on the device.

Because various embodiments of the smart bandage 300 include a microprocessor such as the processor 330 and, in some examples, Bluetooth components such as the Bluetooth components 370, various disclosed embodiments may also serve as active data logging devices for biosensors that use BT LE capabilities. In various embodiments, the smart bandage 300 or other suitable smart wearable device, such as a patch, sticker, bandage, or band may be worn by a user (e.g., an active-duty soldier) along with one or more other biosensors such as one or more of a heart monitor, a sweat monitor, a heat monitor, an environmental biosensor, and/or any other type of similar device (e.g., planned, in use, or envisioned to be worn by a soldier). The smart bandage 300 may connect to these biosensors and, because of its greater storage and processing capabilities, process and record readings from these sensors. A healthcare provider or monitor may then use a suitable computing device (e.g., a smartphone) to connect to and communicate with the smart bandage 300 as described herein to obtain readings collected from the sensors attached to the user (e.g., to assess a wearer's ongoing readiness and apply interventions as needed).

Because the smart bandage 300 may include one or more components having the ability to execute algorithms and code, the smart bandage 300 may use specific algorithms to measure and/or summarize one or more sensor readings, and/or to generate and transmit one or more alerts to a healthcare provider or suitable monitor via a mobile device communicating with the smart bandage 300. In a particular embodiment, the system may generate and transmit an alert in response to detecting a measurement or calculation that indicates that a problem has been detected with a wearer of the smart bandage 300. For example, the smart bandage 300 may execute an algorithm to capture sweat sensor data and calculate a quantity and/or salinity of the wearer's sweat. Using one or more predetermined values and/or thresholds, the smart bandage 300 may generate an alert that the wearer is dehydrated based on, for example, one or more changes in the volume of sweat that the wearer is producing and the calculated salinity of the wearer's sweat. The smart bandage 300 may transmit this alert to another device to notify that device's user (e.g., a healthcare provider or monitor) of the alert in response to the smart bandage 300 being activated by that device, for example, as described above.

In various non-military embodiments, various disclosed embodiments may alternatively be implemented as a personal wearable (e.g., a band, a patch, etc.) for people wearing one or more medical sensors that require long term observations at home or in a hospital, which may give such people much greater mobility as compared to wired monitoring devices or bulky worn monitoring devices currently in use. In other embodiments, athletes may wear one or more sensors and one or more versions of a smart bandage or other smart wearable device such as those discussed above during sporting events so that coaches or trainers can measure their medical signs. In particular embodiments, the components and functions of the smart bandage 300, and any of the disclosed systems and methods, may be implemented in implantable medical devices surgically implanted into a user and capable of one or more of the aspects described herein.

In a particular embodiment, a smart bandage or other smart wearable device as described herein may be used in a pandemic situation. For example, a patient reporting symptoms of a virus (e.g., COVID-19) may report to a hospital emergency room wherein healthcare providers may determine that the patient requires transport to a specialized medical facility. The healthcare providers at the emergency room may attach a smart bandage or other smart wearable device as described herein to the patient and load the smart bandage/device with information related to the patient's symptoms, diagnosis, and care provided thus far. The patient may then be transported to the specialized medical facility, where specialized healthcare providers may retrieve this patient's medical data and provide the appropriate care.

Sensor Data Collection and Aggregation System and Apparatus

In various embodiments, one or more of the exemplary wearable data storage and transmission devices and systems described herein (e.g., wearable data storage and transmission device 120, wearable data storage and transmission device 300) may implemented in a system that collects data from a wearer using one or more sensors configured on the wearer and/or on apparel or other items attached and/or proximate to the wearer. For example, one or more sensors may be affixed to a wearer and/or a wearer's clothing using adhesive (e.g., in the form of a sticker). In another example, one or more sensors may be configured on an exoskeleton configured about a wearer. Each such sensor may be configured to communicate with a wearable data storage and transmission device that is also configured on or about the wearer. Such communication may be wireless (e.g., via Bluetooth) or wired via a physical connection between the sensor and the wearable data storage and transmission device. In particular embodiments, rather than, or in addition to, communicatively connecting directly to a wearable data storage and transmission device, a first sensor may be configured to communicatively connect to second sensor that then relays or otherwise transmits data received from the first sensor to the wearable data storage and transmission device.

Each such sensor may collect, detect, and/or otherwise generate any type of data, including any type of data described herein. In various embodiments, a particular sensor may be configured to collect health data associated with the wearer, such as heart rate, body temperature, sweat rate, hydration, caloric consumption, energy usage, physical exertion, and/or any other type of biological and/or physiological data. In various embodiments, a particular sensor may also, or instead, be configured to collect data not necessarily directly related to a wearer, such as environmental data for the environment in which the wearer is operating, geographical data, location data, movement data, position data, and/or any other data that may be collected by a sensor. Each such sensor may transmit its collected data to a wearable data storage and transmission device automatically (e.g., periodically, upon collection of new data, etc.) and/or in response to an instruction received from wearable data storage and transmission device. Alternatively, or in addition, each such sensor may store collected data (current data and/or historical data) for retrieval by a wearable data storage and transmission device.

In various embodiments, a wearable data storage and transmission device may periodically collect data from each of one or more sensors with which it is in communication using wireless communications means (e.g., Bluetooth, NFC, etc.) and/or wired communications means. A wearable data storage and transmission device may also, or instead, receive instructions (e.g., from an external device) to collect data from sensors and, in response, poll the one or more sensors with which it is in communication for sensor data. In various embodiments, the wearable data storage and transmission device may be configured, for example by an external device as described herein, to collect sensor data at particular periodic time intervals (e.g., every 30 seconds, every minute, every 5 minutes, every hour, etc.). The wearable data storage and transmission device may be configured to collect data from every sensor at a single time period. Alternatively, the wearable data storage and transmission device may be configured to collect data from particular sensors at particular time periods that differ from other time periods for other sensors. For example, the wearable data storage and transmission device may be configured to collect health-related data from biosensors every five minutes and to collect location data from a positioning sensor once per hour.

In various embodiments, the wearable data storage and transmission device may store the collected sensor data along with any associated data (e.g., time and date collected, etc.) for retrieval by an external device. In particular embodiments, the wearable data storage and transmission device may store the collected data and associated data as raw (e.g., unaltered and uncompressed) data. In other embodiments, the wearable data storage and transmission device may encode, compress, and/or store the collected sensor data in one or more structured data records, such as the structured data records described herein. In various embodiments, the system may aggregate the most recently collected sensor data (e.g., in raw form and/or in encoded/compressed/record form) with previously collected (e.g., historical) sensor data (e.g., that may also be in raw form and/or in encoded/compressed/record form) and then store the aggregated sensor data.

In various embodiments, the wearable data storage and transmission device may use artificial intelligence and/or machine-learning techniques to process and interpret collected sensor data and take one or more action in response. For example, the wearable data storage and transmission device may compare a most recently collected biosensor data value to a historical average value for that biosensor and determine whether the recently collected value differs significantly (e.g., exceeds a threshold difference) from the historical average. If so, the wearable data storage and transmission device may be configured to take one or more actions, such as initiate an audible or visible alert to the wearer and/or transmit an alert communication to an external device. Alternatively, or in addition, the wearable data storage and transmission device may be configured to store, with the recently collected value, a flag or other indicator that indicates that the value is outside of an average or expected range of values.

The actions taken in response to the wearable data storage and transmission device detecting an abnormal sensor value may also include a dynamic alteration to its data collection configuration. For example, the wearable data storage and transmission device may detect a heart rate that is significantly greater than normal (e.g., higher than the average for the past several hours by a particular threshold (e.g., 50% higher, 100% higher, etc.)). In response, the wearable data storage and transmission device may alter its heart rate biosensor data collection schedule from once every five minutes to once every 30 seconds, once every second, substantially continuously, etc., until the average heartrate returns to the previous average. Further in response to detecting such an abnormal condition, the wearable data storage and transmission device may be configured to store a baseline average (e.g., the average heart rate before detecting the elevated rate) for future comparison purposes so that it may determine whether future collected sensor data returns to "normal."

In response to detecting an abnormal condition in data collected from a particular sensor, the wearable data storage and transmission device may also, or instead, adjust a collection schedule for one or more other sensors. For example, in response to detecting a heart rate that is significantly greater than normal form data collected from a heart rate sensor, the wearable data storage and transmission device may collect hydration data from a hydration biosensor (e.g., that may be a sensor distinct from the heart rate sensor) more often (e.g., adjust from once every five minutes to once every minute or once every 30 seconds). Any adjustment of a data collection schedule for any particular sensor based on data collected any that sensor and/or any other sensor may be implemented by the wearable data storage and transmission device.

In various embodiments, the wearable data storage and transmission device may also, or instead, perform calculations and/or processes using the data collected to determine whether and how to dynamically adjust sensor data collection schedules. For example, the wearable data storage and transmission device may determine, based on a detected increased heart rate and a detected geographical elevation in the wearer's geographical location, to collect wearer oxygen level data more frequently from a biosensor configured to detect the wearer's oxygen levels.

Figure 4:
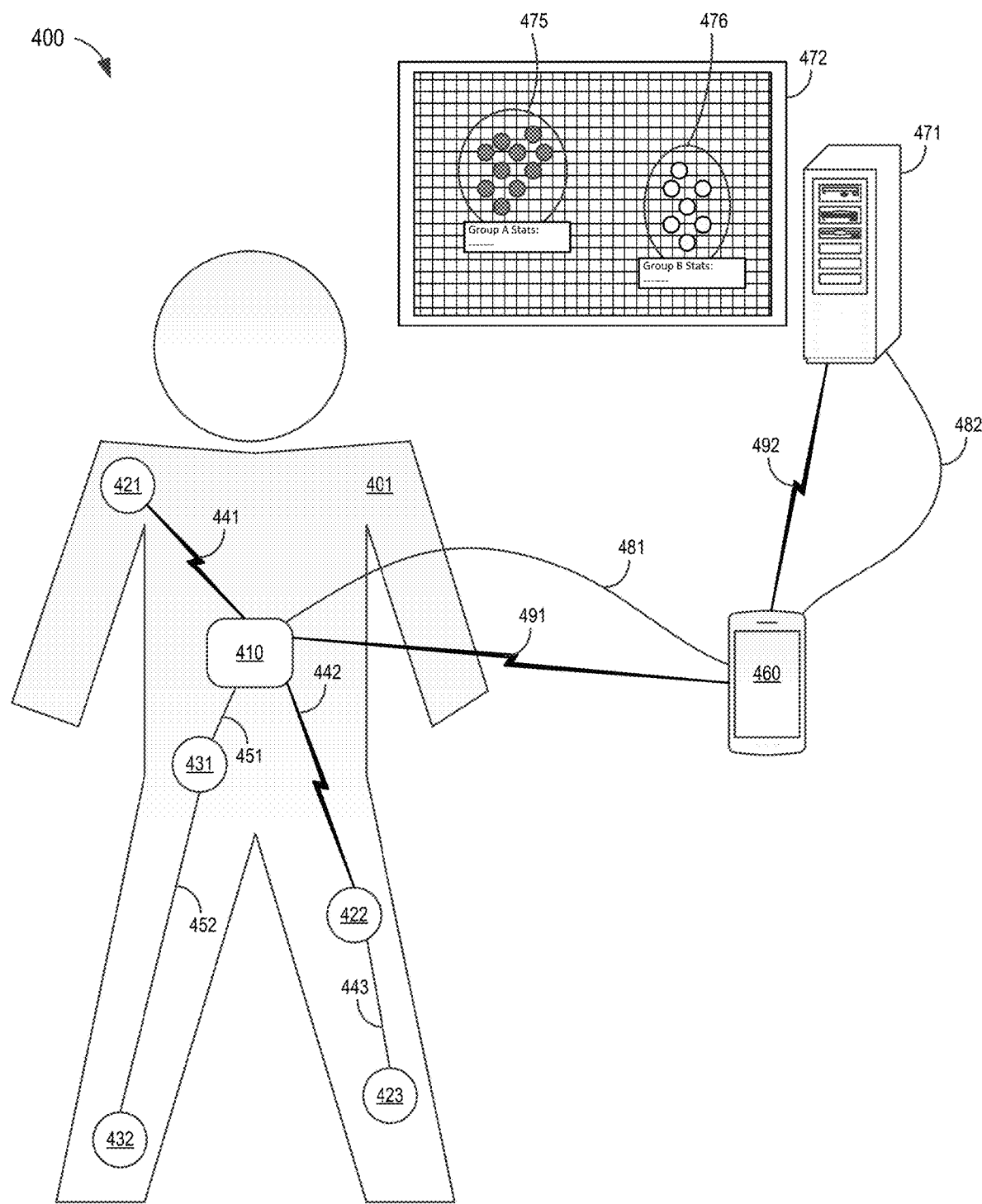
FIG. 4 is a diagram illustrating an exemplary wearable storage and transmission system in which various embodiments may be implemented.

FIG. 4 illustrates a block diagram representing an exemplary wearable data storage and transmission device and system 400. In this figure, an example wearer 401 is wearing, or is otherwise configured with, a wearable data storage and transmission device 410 and several sensors 421, 422, 423, 431, 432. The wearable data storage and transmission device 410 may be any wearable data storage and transmission device as described herein and/or configured to perform any of the various aspects of the disclosed systems and methods. Each of the sensors 421, 422, 423, 431, 432 may be any type of sensor, including a biosensor, an environmental sensor, any other type of sensor described herein, or any other type of sensor suitable for use in a wearable data storage and transmission device and system.

Each sensor may be configured to communicate with the wearable data storage and transmission device 410. In various embodiments, either or both wired and wireless communications means may be used. For example, the sensor 421 may be configured to wirelessly connect to the wearable data storage and transmission device 410 via a wireless communications connection 441. In a particular embodiment, the sensor 421 may be configured with one or more Bluetooth Low Energy (BT LE) components and/or capabilities. The wireless communications connection 441 may be a Bluetooth communications connection (e.g., utilizing a Bluetooth specification) established between the wearable data storage and transmission device 410 and the sensor 421. Similarly, the sensor 422 may be configured to wirelessly connect to the wearable data storage and transmission device 410 via wireless communications connection 442, which may also be a Bluetooth communications connection. Alternatively, other wireless communications means may be used for wireless communications between one or more sensors and a wearable data storage and transmission device. The sensor 431 may be configured to communicate with the wearable data storage and transmission device 410 via a wired communications connection 451. For example, the sensor 431 may be connected directly to the wearable data storage and transmission device 410 via a physical wire and connections.

In various embodiments, one or more sensors may serve as relays for one or more other sensors, or otherwise facilitate the transmission of data from one or more other sensors. For example, the sensor 431 may receive data from the sensor 432 via a wired communications connection 452. The sensor 431 may then transmit that data, via the wired communications connection 451, to the wearable data storage and transmission device 410. In particular embodiments, the sensor 431 may simply relay data received from the sensor 432 unaltered to the wearable data storage and transmission device 410, while in other embodiments, the sensor 431 may process, augment, or otherwise alter the data received from the sensor 432 before transmission to the wearable data storage and transmission device 410.

In another example, a sensor may provide wireless communications relay for a sensor that does not have wireless communications capabilities. For example, the sensor 422 may receive data from the sensor 423 via a wired communications connection 443. The sensor 422 may then transmit that data, via the wireless communications connection 442, to the wearable data storage and transmission device 410. The sensor 422 may wirelessly relay data received from the sensor 423 unaltered to the wearable data storage and transmission device 410 or may process, augment, or otherwise alter the data received from the sensor 423 before wireless transmission to the wearable data storage and transmission device 410.

The wearable data storage and transmission device 410 may be configured to poll each of the sensors to which it is connected for sensor data periodically and/or in response to receiving an instruction to do so (e.g., from an external device such as device 460). In various embodiments, the wearable data storage and transmission device 410 may be configured to "wake up" periodically (e.g., as described herein) and retrieve sensor data from each sensor, or from a subset of one or more sensors, with which it may be configured to communicate. The wearable data storage and transmission device 410 may then store the collected sensor data for later retrieval by an external device. In particular embodiments, the wearable data storage and transmission device 410 may simply store the raw data as collected, in some embodiments along with any associated data, while in other embodiments the wearable data storage and transmission device 410 may compress the collected sensor data and/or store the collected sensor data using any of the data structure generation techniques set forth herein.

The wearable data storage and transmission device 410 may be configured to communicate with an external device 460 using either or both wired and wireless communications means. In particular embodiments, the wearable data storage and transmission device 410 may be activated by the external device 460 using wireless means (e.g., NFC or Bluetooth as described herein) and configured to transfer the collected sensor data to the external device 460, automatically and/or on demand, via the wireless communications connection 491. The external device 460 may also, or instead, use the wireless communications connection 491 to exchange data with the wearable data storage and transmission device 410. For example, the external device 460 may transmit configurations, instructions, and/or to adjust the functionality of the wearable data storage and transmission device 410 (e.g., adjust sensor data collection periods, alert thresholds, etc.) and/or otherwise configure the device 410 via the wireless communications connection 491.

Alternatively, or in addition, the wearable data storage and transmission device 410 may be activated by the external device 460 using wired means (e.g., as described herein) and configured to transfer the collected sensor data to the external device 460, automatically and/or on demand, via the wired communications connection 481. The external device 460 may also, or instead, use the wired communications connection 481 to exchange data with the wearable data storage and transmission device 410. For example, the external device 460 may transmit configurations, instructions, and/or to adjust the functionality of the wearable data storage and transmission device 410 (e.g., adjust sensor data collection periods, alert thresholds, etc.) and/or otherwise configure the device 410 via the wired communications connection 481.

The external device 460 provide data collected from the wearable data storage and transmission device 410 to a system 471 for additional processing. For example, the external device 460 may transmit data collected from the wearable data storage and transmission device 410 wirelessly to the system 471 via the wireless communications connection 492. The wireless communications connection 492 may be any combination of one or more types of wireless communications means, such as Wi-Fi, cellular, Bluetooth, etc. Alternatively, or in addition, the external device 460 may transmit data collected from the wearable data storage and transmission device 410 via wired means to the system 471 via the wired communications connection 482. The wired communications connection 482 may be any combination of one or more types of wired communications means. In particular embodiments, the communications means used to facilitate communications between the external device 460 and the system 471 may be a combination of wired and wireless communications means.

In various embodiment, the system 471 may collect data from multiple wearers of wearable data storage and transmission devices, such as the wearable data storage and transmission device 410, provided via one or more external devices, such as the external device 460. The system may aggregate this data for processing and/or presentation to a user, enabling the user to view and/or manipulate individual and/or aggregated wearer sensor data. For example, the system 471 may generate a graphical user interface 472 that presents aggregated and/or individual sensor data for groups of wearers. The group 475 may represent a group of wearers associated with one another (e.g., a unit of soldiers, a team of athletes, etc.) and the group 476 may represent another group of wearers associated with one another (e.g., a different unit of soldiers, an opposing team of athletes, etc.). The system may present information for each wearer within each of groups 475 and 476 and/or aggregated sensor data for each group (e.g., group average sensor data, group extreme sensor data, group outlier sensor data, etc.).

Individual and/or aggregated wearer sensor information, as provided by a system such as system 471 working in conjunction with wearable data storage and transmission devices such as device 410 and/or external devices such as device 460, may assist a user in making more informed decisions regarding groups of wearers dispersed across an environment. For example, the collected wearer sensor data may be used by a commander to determine more efficient allocation of resources for soldiers in a combat or training environment and to assist in making better decisions regarding troop allocations and movements. In another example, the collected wearer sensor data may be used by a coach to determine player conditions and training and gameplay adjustments for both the team and for individual players.

Wearable Data Storage and Transmission Device Wireless Control Process

Figure 5:
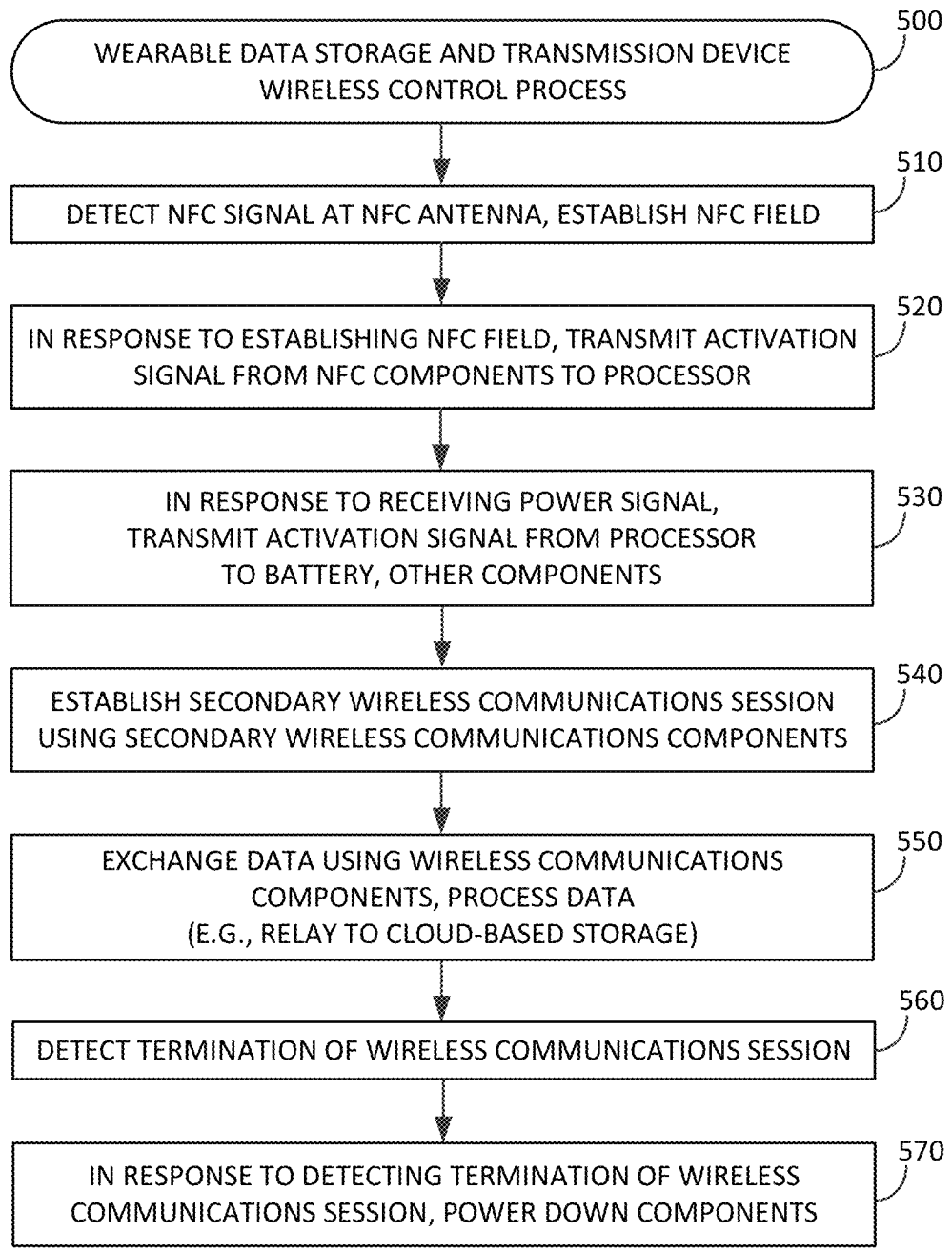
FIG. 5 is a flow chart showing an example of a wireless control process according to various embodiments.

FIG. 5 illustrates an example Wearable Data Storage and Transmission Device Wireless Control Process 500 that may be performed by a wearable data storage and transmission device (e.g., a smart bandage), such as any of the wearable data storage and transmission device 120, the wearable data storage and transmission device 300, and the wearable data storage and transmission device 410, according to various embodiments. In performing the Wearable Data Storage and Transmission Device Wireless Control Process 500, the system begins at Step 510 where an NFC signal transmitted by an NFC initiator device may be detected by an NFC antenna configured at a wearable data storage and transmission device. In response to detecting the NFC signal, the one or more NFC components of the wearable data storage and transmission device may then establish an NFC field with the initiator device.

At Step 520, in response to successfully establishing the NFC field, one or more NFC components of the system, such as an NFC processor, may transmit an activation signal to a system processor. In particular embodiments, at Step 520 the NFC processor may also transmit an activation signal to one or more other components of the system, such as a battery or other power source.

At Step 530, in response to receiving the activation signal from the NFC processor, the system processor may transmit an activation signal to one or more other components of the wearable data storage and transmission device, or otherwise cause such components to power up. In particular embodiments, the processor may instruct the battery to power on, which may in turn provide power to one or more of the other components of the wearable data storage and transmission device, causing such components to power on.

At Step 540, secondary (e.g., non-NFC) wireless communications components of the wearable data storage and transmission device may attempt to establish a wireless communications session using their respective technology. In particular embodiments, the system may not be configured with any other wireless communications capabilities other than NFC. In such embodiments, Step 540 may be bypassed. In other particular embodiments, the system may be configured with secondary wireless communications components that may be one or more Bluetooth components, one or more Wi-Fi components, and/or one or more other wireless communications components, for example, as described above. At Step 540, the system, after powering such secondary wireless communications components at Step 530, may use the secondary wireless communications to establish a communications session that the system may use to wirelessly exchange data with another device (e.g., the NFC initiator device, any other device).

At Step 550, the system may exchange data wirelessly with one or more remote computing devices. The system may use one or more NFC components, Bluetooth components, Wi-Fi components, and/or other wireless communications components to perform this data exchange. Further at Step 550, the system may process the exchanged data in any suitable manner (e.g., store, transmit, compress, decompress, etc.). In particular embodiments, data may be received from and/or transmitted to a remote system such as a cloud-based system for storage and/or processing of such data. The system may relay such the data between itself and a cloud-based system via one or more intermediary devices (e.g., laptop computer, desktop computer, server computer, table computer, smartphone, network device, etc.).

At Step 560, the system may detect the termination of one or more wireless communications sessions. For example, the system may detect the breaking of the NFC field with the NFC initiator device, the breaking of a Bluetooth bond with another device, the termination of an IP or TCP communication session with another computing device, etc. At Step 570, in response to detecting the termination of the wireless communications session, the system may power down. In particular embodiments, the processer may transmit one or more signals to each other component of the wearable data storage and transmission device that cause those components to power off.

In particular embodiments, the system may have multiple wireless communications sessions active at one time, as described above. For example, the system may initially establish an NFC field with an NFC initiator device and then establish a Bluetooth bond with a device (that may or may not be the NFC initiator device) for data exchange. In such embodiments, the termination of either or both such wireless communications sessions may cause the system processor to power down the system. For example, the system may be configured to maintain power to its components for the duration of an active NFC field, while establishing and terminating several Bluetooth bonds and/or Wi-Fi communications session while that NFC field is active, and only powering down its components when the NFC field is broken. In another example, the system may be configured to maintain power to its components for the duration of an active Bluetooth bond, regardless of whether an active NFC field is maintained, only powering down its components when the Bluetooth bond is broken. The system may be configured to power up and/or power down its components based on any combination of wireless communications session establishment and termination.

Wearable Data Storage and Transmission Device Wired Control Process

Figure 6:
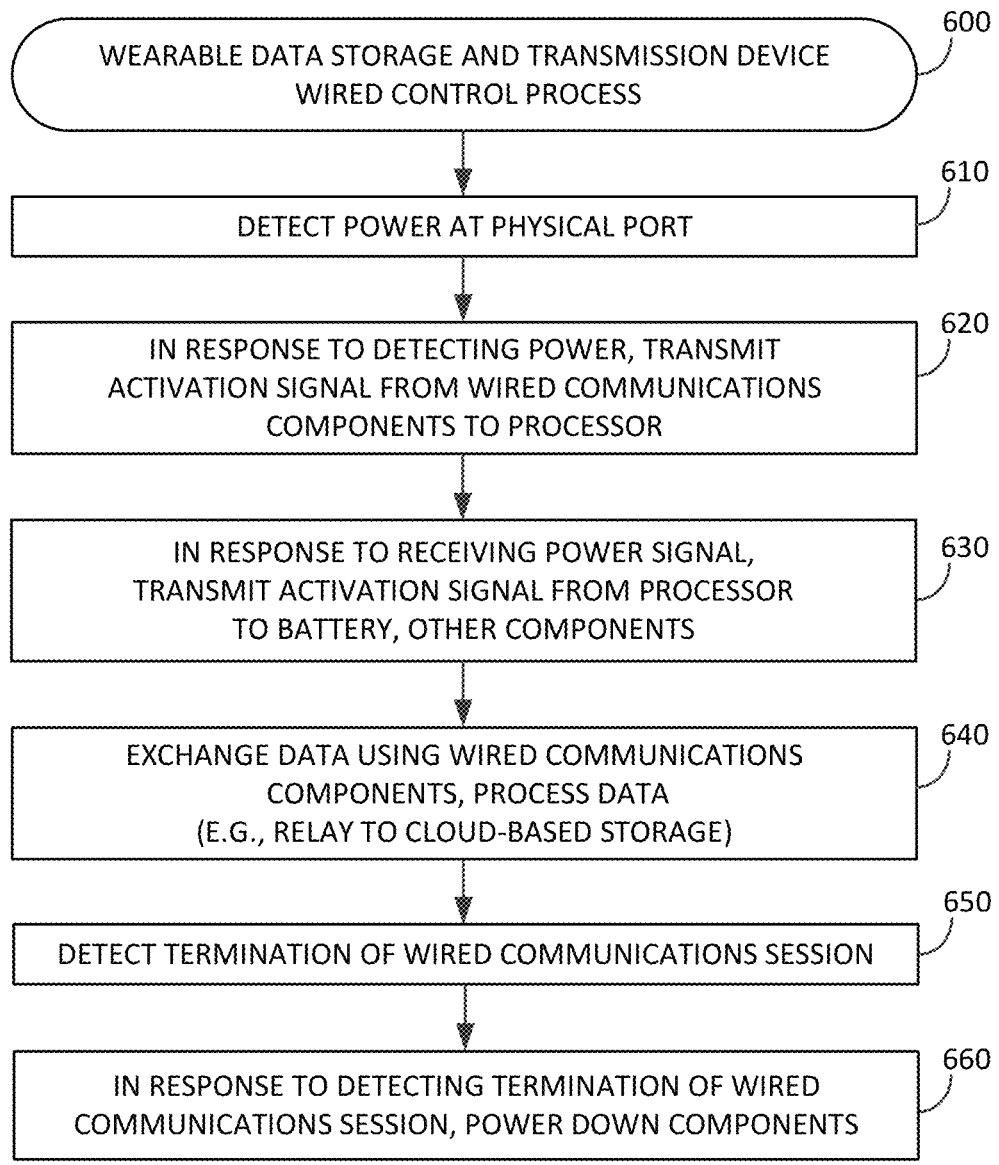
FIG. 6 is a flow chart showing an example of a wired control process according to various embodiments.

FIG. 6 illustrates an example Wearable Data Storage and Transmission Device Wired Control Process 600 that may be performed by a wearable data storage and transmission device (e.g., a smart bandage), such as any of the wearable data storage and transmission device 120, the wearable data storage and transmission device 300, and the wearable data storage and transmission device 410, according to various embodiments. In performing the Wearable Data Storage and Transmission Device Wired Control Process 600, the system begins at Step 610 where the system may detect power or a signal (e.g., voltage, amperage, current, any other electrical signal, etc.) at a physical port configured at a wearable data storage and transmission device, thereby indicating that a connector has been seated in the physical port.

At Step 620, in response to detecting the power or signal, the one or more wired communications components of the wearable data storage and transmission device that are connected to the port may transmit an activation signal to a system processor. In particular embodiments, at Step 620 the one or more wired communications components may also transmit an activation signal to one or more other components of the system, such as a battery or other power source.

At Step 630, in response to receiving the activation signal from the one or more wired communications components, the system processor may transmit an activation signal to one or more other components of the wearable data storage and transmission device, or otherwise cause such components to power up. In particular embodiments, the processor may instruct the battery to power on, which may in turn provide power to one or more of the other components of the wearable data storage and transmission device, causing such components to power on.

At Step 640, the system may establish a communications session to exchange data via a physical medium with one or more external computing devices (e.g., a physically connected laptop, computer, tablet, etc.). The system may exchange data using wired communications means with the one or more external computing devices. The system may use one or more wired communications components to perform this data exchange. In particular embodiments, the system may be detected and used in a similar manner as a typical USB device (e.g., as an external drive). Further at Step 640, the system may process the exchanged data in any suitable manner (e.g., store, transmit, compress, decompress, etc.). In particular embodiments, data may be received from and/or transmitted to a remote system such as a cloud-based system for storage and/or processing of such data. The system may relay such the data between itself and a cloud-based system via one or more intermediary devices (e.g., laptop computer, desktop computer, server computer, table computer, smartphone, network device, etc.).

At Step 650, the system may detect the termination of one or more wired communications sessions. For example, the system may detect the separation of a physical connector from a port configured at the system (e.g., by detecting the cessation of a signal or power via the port). Alternatively, or in addition, the system may receive a signal from one or more external computing devices indicating the one or more external computing devices are terminating the wired communications session with the system. In particular embodiments, the system may detect the termination of an IP or TCP communication session with the one or more external computing devices. At Step 660, in response to detecting the termination of the wired communications session, the system may power down. In particular embodiments, the processor may transmit one or more signals to each other component of the wearable data storage and transmission device that cause those components to power off.

In particular embodiments, the system may have multiple wired and/or wireless communications sessions active at one time, as described above. For example, the system may initially establish an NFC field with an NFC initiator device and then establish a wired communications session for data exchange. In such embodiments, the termination of either or both such communications sessions may cause the system processor to power down the system. For example, the system may be configured to maintain power to its components for the duration of an active NFC field, while establishing and terminating several Bluetooth bonds, Wi-Fi communications sessions, and/or wired communications sessions while that NFC field is active, and only powering down its components when the NFC field is broken. In another example, the system may be configured to maintain power to its components for the duration of an active wired communications session, regardless of whether a wireless communications session is active or not, only powering down its components when the wired communications session is terminated. For example, the system may maintain a wired communications session to provide power to the system components and/or charge the system battery while using one or more various wireless communications sessions to transmit and received data. The system may be configured to power up and/or power down its components based on any combination of wired and/or wireless communications session establishment and termination.

Wearable Data Storage and Transmission Device Contact Tracing Process

In various embodiments, the system may be used to assist in contact tracing, for example during a viral outbreak or other pandemic event (e.g., COVID-19 pandemic). In such situations, governments and/or public health organizations may desire to trace the past locations of particular individuals that test positive for a virus or other contagious disease so that they can steps to locate others who may be infected. Similarly, militaries may wish to track the locations of solders who are found to be infected with a contagion to determine when and where a contagious disease may have spread to other soldiers. The system may be used to collect data regarding the locations and times of presence of the individual wearing the system that can later be used in such contact tracing.

Figure 7:
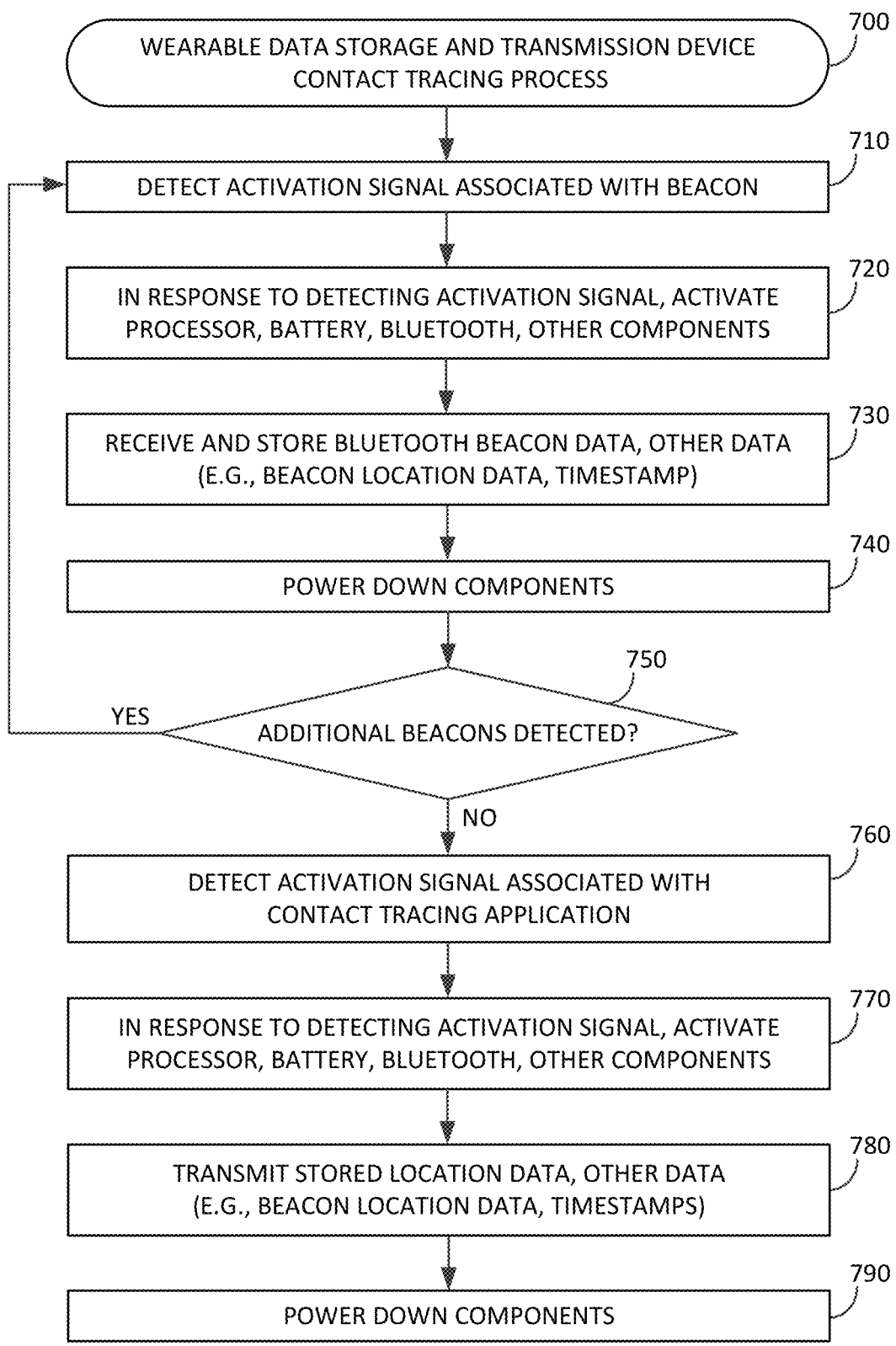
FIG. 7 is a flow chart showing an example of a contact tracing process according to various embodiments.

FIG. 7 illustrates an example Wearable Data Storage and Transmission Device Contact Tracing Process 700 that may be performed by a wearable data storage and transmission device (e.g., a smart bandage), such as any of the wearable data storage and transmission device 120, the wearable data storage and transmission device 300, and the wearable data storage and transmission device 410, according to various embodiments. In performing the Wearable Data Storage and Transmission Device Contact Tracing Process 700, the system begins at Step 710 where the system may detect an activation, for example, an activation signal associated with a Bluetooth beacon. In particular embodiments, the activation signal may not be associated with the Bluetooth beacon, but may be received proximate to such a beacon (e.g., via an entry authorization device used for access to a room in which a Bluetooth beacon is located). In various embodiments, the activation signal may be an NFC signal transmitted by an NFC initiator device and may be detected by an NFC antenna configured at a wearable data storage and transmission device as described herein. As described above, in response to detecting the NFC signal, the one or more NFC components of the wearable data storage and transmission device may then establish an NFC field with the initiator device. In various embodiments, the system may detect another type of activation signal at Step 710, such as a Bluetooth signal or any other type of wireless activation signal.

At Step 720, in response to detecting the activation signal, the system may transmit an activation signal to a system processor, battery, and/or any other system components, and/or may otherwise activate such components. Among such activated components, the system may activate its Bluetooth components. In particular embodiments, at Step 720 an NFC processor may transmit such an activation signal to one or more components of the system. In particular embodiments, a Bluetooth processor may transmit the component activation signal to one or more components of the system.

At Step 730, the system may detect or receive a Bluetooth transmission (e.g., broadcast) from the Bluetooth beacon. This transmission may include location identifying information that can be used to determine a physical location of the beacon (and therefore a current physical location of the system). The system may store this received location information along with an indication of the current time and date so that the system has a record stored reflecting the location of the system user at the current time. The system may determine the current time and/or date from one or more system components (e.g., a system clock) and/or based on the Bluetooth transmission received from the Bluetooth beacon.

At Step 740, the system may power down one or more of its components based on determining that the communication with Bluetooth beacon is complete. For example, the system may be configured to the power down after receiving current location information from a Bluetooth beacon. In another example, the system may detect the termination of one or more wireless communications sessions (e.g., an NFC session, a Bluetooth session, etc.). In particular embodiments, the system may be configured to power down after a predetermined amount of time after detecting a Bluetooth beacon and/or after being powered on. The system may be configured to power up and/or power down its components based on any combination of wireless and/or wired communications session establishment and termination and/or timeouts. At Step 650, the system may detect additional Bluetooth beacons (e.g., as the system user travels from place to place) and, in response to such detection, may return to Step 710.

At Step 760, the system may detect an activation signa associated with a contact tracing application or system. For example, the system may be attached or otherwise communicatively connected, via wireless and/or wired means, to one or more devices or systems as described herein. Using such a connection, the system may detect an activation signal and, in response, at Step 770 the system transmits an activation signal to the system processor, battery, and/or any other system components, and/or may otherwise activate such components. The system may then establish and/or maintain one or more wireless and/or wired communication sessions with one or more devices or systems as described herein.

Via such one or more communication sessions, at Step 780 the system may receive and respond to an instruction to transmit its stored contact tracing data and/or any other associated data to one or more devices or systems. For example, the system may have been physically attached (e.g., via a micro-USB cable) to another device and may be queried for its contact tracing data from an application executing on that device. The system may transmit other data that may be of user with the contact tracing data, such as user identifying information. This data may then be stored on the other device and/or transferred to one or more other storage systems, such as a cloud-based contact tracing system. Such contact tracing systems may aggregate all such data, and in combination with infection test results, determine potentially infected individuals.

Sensor Data Collection and Aggregation Process

Figure 8:
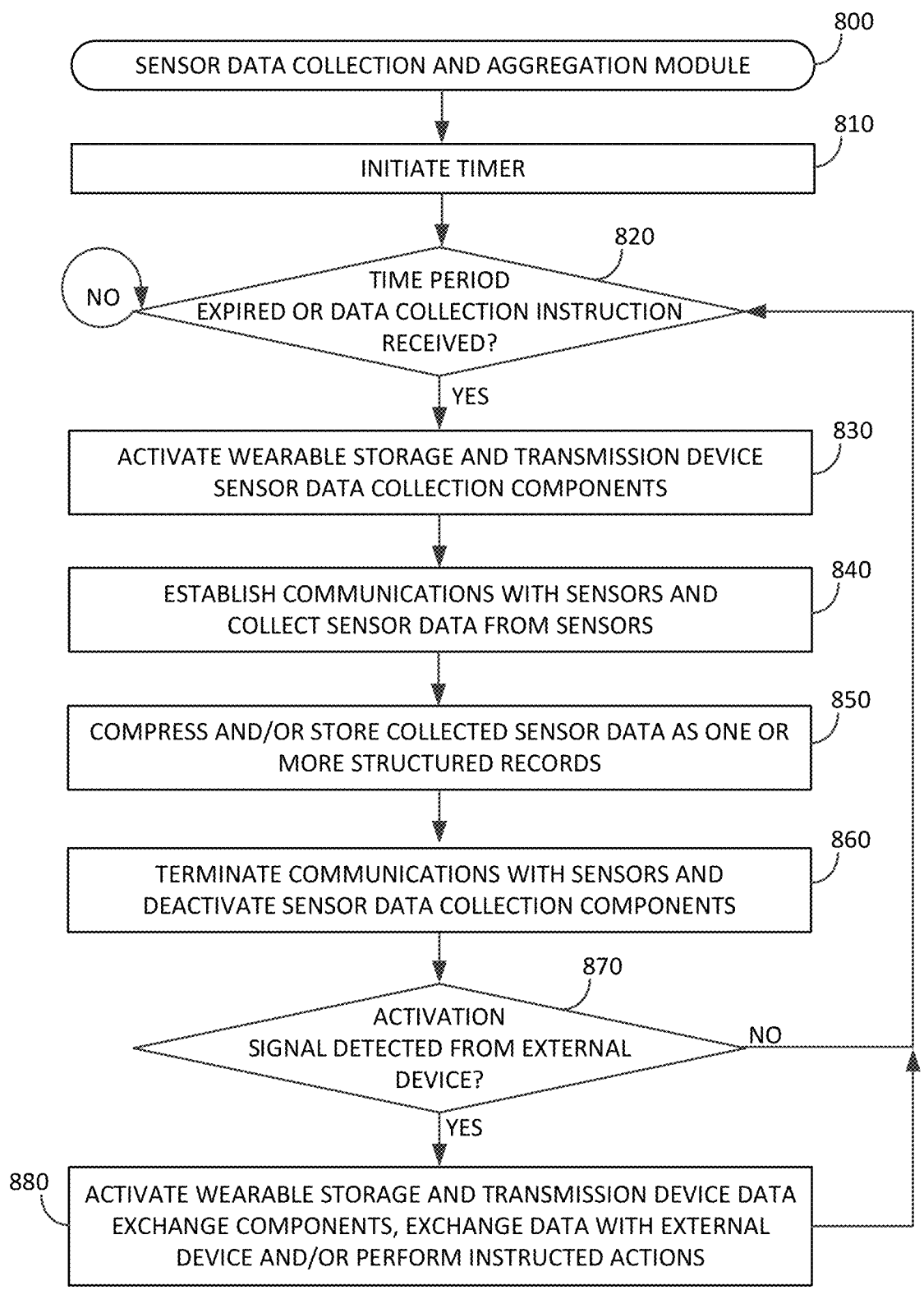
FIG. 8 is a flow chart showing an example of a sensor data collection and aggregation process according to various embodiments.

FIG. 8 illustrates an example Sensor Data Collection and Aggregation Process 800 that may be performed by a wearable data storage and transmission device, such as any of the wearable data storage and transmission device 120, the wearable data storage and transmission device 300, and the wearable data storage and transmission device 410, according to various embodiments. In performing the Sensor Data Collection and Aggregation Process 800, the system begins at Step 810 where the wearable data storage and transmission device may initiate a timer that may be used by the system to determine when to collect data from one or more sensors. As noted above, the system may be configured to periodically collect data from one or more sensors with which it may be in communication. In particular embodiments, the system may collect data from all sensors at a particular time interval, while in other embodiments, the system may collect data from different sensors at different time intervals.

At Step 820, the system may determine whether the time period has expired (e.g., that the time elapses since the last data collection has met the data collection time threshold). If not, the system remains at Step 820 awaiting expiration of the time period. Also, or instead, the system may also determine at Step 820 if the system has received an instruction to collect sensor data. For example, in particular embodiments an external device may transmit (e.g., using wired or wireless communications) an instruction to a wearable data storage and transmission device instructing the device to collect sensor data from one or more of its connected sensors. In response, the system may retrieve (e.g., current) data from the one or more sensors as instructed.

If the system determines that the time period between data collections has expired and/or if a data collection instruction has been received, at Step 830 the system may activate one or more of its various components to initiate communications with one or more sensors. For example, the system may provide power and/or otherwise activate one or more wireless communications components (e.g., Bluetooth components, NFC components, Wi-fi components) and/or one or more wired communications components (e.g., ports, interfaces).

At Step 840, the system may establish communications with the one or more sensor from which it has been configured to retrieve sensor data. In particular embodiments, the system may initiate a Bluetooth bonding process with one or more sensors. The system may also, or instead, establish a communications session of any other type using wired and/or wireless communications means. Further at Step 840, the system may collect sensor data from the one or more sensors. In particular embodiments, for example where the sensor may be a relatively simple device, the system may simply poll the sensor to return its current data. In other embodiments, for example where the sensors may be relatively "intelligent," the system may provide specific instructions requesting particular data and other information from the sensor. In response, the sensor may provide the sensor data or otherwise facilitate collection of the sensor data.

At Step 850, the system may store the data and perform any other processing as configured. For example, the system may compress and/or encode the sensor data, and/or generate one or more structured records (e.g., as described herein) for the sensor data, so that the system may store the data in a manner that improves memory storage space utilization. Various methods and systems for encoding and compressing such data are described in detail below.

At Step 860, the communications sessions with the one or more sensors may be terminated and the sensor data collection components may be deactivated or otherwise powered down. Alternatively, the sensor data collection components may simply be deactivated or powered down, thereby terminating any communications sessions with any sensors. By powering down the sensor data collection components when not in use, the system may reduce power usage and prolong battery life.

At Step 870, the system may determine whether an activation signal has been received from an external device. If not, the system returns to Step 820 to await the expiration of the time period for the next sensor data collection, the receipt of an instruction to collect sensor data, and/or the receipt of an activation signal from an external device.

If, at Step 870, the system detects an activation signal form an external device, at Step 870 the system activates the components needed to communicate with the external device and exchanges data with the external device. For example, the system may detect an NFC signal and may activate components needed to establish communications with the external device (e.g., NFC, Wi-Fi, Bluetooth, etc.). In another example, the system may detect a physical connection to the external device and activate components needed to establish communications with the external device (e.g., wired communications components and/or wireless components, etc.). Once a communications session is established, the system may then provide the external device with sensor data and/or exchange other data with the external device (e.g., receive configurations, provide other data, etc.). The communications session may then be terminated. Various methods and systems for activating a wearable data storage and transmission device and exchanging data using an external device are described in detail herein. Once data exchange with the external device is complete, the system may resume sensor data collection, returning to Step 820.

Structured and Configurable Data Compression—Overview

In modern computing environments, data may be exchanged between mobile devices, computers, and applications quickly and reliably using networks capable of transmitting large volumes of data at high speeds. Devices operating in such environments often include wireless capabilities that further increase the ease with which large amounts of data may be quickly exchanged. As discussed above, in most modern computer environments, there is usually little need to reduce or minimize the size, type, and structure of data being exchanged because the devices and the network used to exchange the data can typically transmit, receive, and store large volumes of data at low cost and without sacrificing the user experience. This has resulted in the proliferation of verbose and complex data structures and message formats. Such data structures and message formats are designed to exchange data between applications and allow computers to process and interpret the structures and messages into actionable records.

For example, in the medical space, computing devices may use the Health Level 7 (HL7) data structures and message formats to provide robust data exchange. HL7 is designed to facilitate the communication of medical information in a standardized manner using structured formats, allowing the movement and sharing of patient records between disparate medical applications and systems. In another example, systems may use data structures and message formats defined by the Fast Healthcare Interoperability Resources (FHIR) standard that use a common internet message structure (e.g., JavaScript Object Notation (JSON)) for formatting data that is to be exchanged over the Internet and/or via Web Services. The messages generated using such standards may be lengthy and consume large amounts of storage space. The devices processing such messages may use relatively large amounts of memory to represent the information contained in such messages. The size of such messages is largely due to the manner in which the information within the messages is encoded and the structural nature of the messages themselves. Systems commonly use such data structures and message formats in situations that require the electronic, structured, and computable exchange of important information, such as medical data.

However, it may be difficult or impossible to accommodate such large and complex structured message formats in environments and situations that lack the network infrastructure and device capabilities that would typically facilitate the use of such message structures and formats, such as the DIL environments described above. In such environments and situations, there are limits on the time, size, and/or amount of data that can be transmitted, received, and/or stored at any given time. Therefore, in such environments and situations, it may be advantageous to compress data and/or optimize data transmission to maximize the amount of information that can be transmitted and received in the least amount of time and using the least amount of resources.

Various embodiments are described herein that use algorithms and compression methods for transmitting structured and computable data that may, for example, facilitate data exchange in DIL environments. The disclosed systems and methods may also provide means for transmitting large amounts of structured data more efficiently. While some of the examples used herein may be described specifically in regard to the exchange and storage of medical information in DIL environments, one skilled in the art will recognize that various disclosed embodiments may be applicable to the exchange and storage of any type of data in any type of environment and may be used in any system that transmits, receives, and/or stores data. Various disclosed embodiments may further be used to compress and communicate any suitable structured dataset more efficiently.

In various embodiments, the system may generate a structured, compressed, and transmittable record that increases the amount of data carried by such a record using the methods and algorithms described herein to compress and encode structured data, such as medical data. In various embodiments, such data may be received, stored, and/or processed on a wearable data storage and transmission device and transmitted to other devices from a wearable data storage and transmission device as described herein, such as the smart bandage 300 and the wearable data storage and transmission device 410. In other various embodiments, such data may be received, stored, and/or processed on a computing device for transmittal to a smart bandage or other smart wearable device as described herein, such as the smart bandage 300 and the wearable data storage and transmission device 410. In particular embodiments, such data may be received, stored, and/or processed on a computing device after receipt from such a smart bandage/device.

Byte Level Representation of Coded, Computable Data Elements

In various embodiments, the system may employ a dynamic data model that may be updated and/or modified based on one or more needs of users and one or more issues being addressed by the system. Data models according to various embodiments may be used to structure or otherwise organize computable data (e.g., data that is to be transmitted and/or stored as structured, coded values). In particular embodiments, such computable data may include medical information represented using a predefined terminology set, such as, but not limited to, Logical Observation Identifiers Names and Codes (LOINC), Systematized Nomenclature of Medicine—Clinical Terms (SNOMED-CT), Current Procedural Terminology (CPT), and National Drug Code (NDC) codes. Such codes or terminology used in the data may describe any action, place, and/or entity that is applicable to a patient. For example, the system may use SNOMED-CT codes for heart rate, blood pressure, and oxygen saturation to identify each of these vital signs and indicate its respective value in a data structure that the system may transmit, receive, and/or store.

In various embodiments, the system may use a data model that captures, in one or more data tables, a set of data that may be transmitted. This data model may map the information that would be otherwise require a more complex and lengthier message for transmission to a single byte. The system may use the byte code mapping defined by this data model to encode information (e.g., vital signs, medical data, etc.) and compress the information into a much smaller number of bits of data for transmission, in some examples, into a single byte. In particular embodiments, the system may also, or instead, use a data model that maps information to a code that uses only a few (e.g., 2, 3, 4, 1-10, less than 100, etc.) bytes.

In various embodiments, the system may include a first system, a second system, and one or more intermediate systems, such as a wearable data storage and transmission device, that may have relatively reduced data storage capacity. The first system and the second system may be configured with the encoding tables so that each may be able to compress and decompress (e.g., encode and decode) data to determine the data's full, computable, and readable form. In particular embodiments, the first system may compress and/or encode healthcare data using an encoding table and transmit such data to an intermediate device such as a wearable data storage and transmission device that may store the compressed data. At a later time, the second system may retrieve the compressed data from the intermediate system and decompress and/or decode the data using the same encoding table to reveal the full, computable, and readable form of the data.

Data Structures

In various embodiments, the system may use a targeted layout to minimize the number of bytes needed for each type of data element that the system may encode and/or compress. In a particular embodiment, the system may stack one or more computed byte values derived using, for example, a data model or encoding table as described herein, in a particular order. The system may then transmit or otherwise write these stacked values to an output data stream and/or store them in a target device as compressed data. In particular examples, the output data stream of stacked values (the compressed data) may be transmitted to a smart bandage for storage and transport with a patient.

For example, the system may compress medical data such as vital signs using a structured layout for each vital sign, where an example layout may be represented by:

Vital Code, Unit of Measure, Observed Measurement, Timestamp

The system may eliminate the use of separators (e.g., byte-sized indicators) to indicate each of both the beginning and the end of each encoded value (e.g., vital code, unit of measure, etc.), thereby saving two bytes of space in a compressed record. In various embodiments, the system may insert a separator value between an indication of an observed measurement and an indication of a timestamp and/or at the end of a record to facilitate the recognition of these values (e.g., by this and/or other systems), rather than a separator value indicating the end of one of these pieces of data and then another separator indicating the beginning of the next piece of data. A separator byte value may be used to address variable length values and timestamps that may not be predictable. However, even with variable measurement or numeric values such as a timestamp, the system may convert these values to bit value representations that may be represented as bytes. By using bit-level values and corresponding byte representations, the system may eliminate the use of strings for numeric values (e.g., a string representing the characters associated with the numeric value) and compress numbers down significantly by indicating the numeric values in binary. For example, the system may represent the decimal value "1000" as the binary value "1111101000" in bits which can be stored in two bytes, rather than the four bytes that would be required to represent the decimal value "1000" as a string of the characters '1', '0', '0', '0'.

In various embodiments, the system may reserve one or more (e.g., four) byte codes to serve as markers to facilitate the recognition of separations between values. In a particular embodiment, the system may reserve a byte code for representing each of: (1) a separation of individual complete records; (2) a separation of values when the value is of variable length; (3) a separation of sections of data; and/or (4) a demarcation of an end of a complete data record. The system may also, or instead, use other byte values to indicate any other separation or demarcation.

Bit Packing and Optimizing Space

When compressing structured data, storage space may be wasted when the actual amount of data associated with a defined segment of data consumes less space than the allocated or allotted space for that segment in the structured layout of a record. In various embodiments, the system may reduce such wastage by analyzing each segment of data as it is compressed and comparing the space requirements for the actual data to be included in a segment against the allocated space assigned to that segment in the record. If the system determines that the amount of space needed for the actual data as encoded and compressed is less than the space allocated to that segment, the system may use the remaining, unused space for the next segment of data. In this way, the system may ensure that "blank" or empty space in the compressed record is not wasted, thereby reducing the overall storage space consumed by the record. The system may use one or more special byte code designators as described herein to indicate that an end of a data segment or record has been reached (e.g., when the segment or record requires less space than normally used or allotted to it).

By employing these bit packing analysis techniques, some of the various disclosed embodiments may ensure that data is compressed sufficiently to fit within a target record size. For example, the system may compress medical data sufficiently to be stored on one or more small form factor devices, such as near-field communications (NFC) Tag 216 stickers and within Quick Response (QR) codes. NFC Tag 216 stickers have a physical storage limit of 888 bytes, while QR codes have a storage limit of approximately 2900 bytes with limited error correction. In such embodiments, packing data (e.g., as bytes) efficiently may help maximize the amount of information that can be transmitted within the space constraints of the device/sticker. In other embodiments, the system may compress medical data in order to optimize the use of data storage media on devices that have relatively larger storage capacity, such as a smart bandage.

Data Compression Prioritization

In various embodiments, the system may prioritize the compression of one or more specific data segments in determining how to utilize unused space in a data structure. The system may designate one or more particular data segments and/or structures as being higher priority when performing bit packing and/or compression. For example, when attempting to meet a maximum byte threshold that may be based on a target device's storage capacity or other criteria, the system may prioritize particular data segments and/or structures in determining an order in which to compress segments or structures.

For example, in a medical information messaging and data exchange scenario, the system may specify that one or more particular types of information are more important and should take precedence over other information when the total amount of data being processed (e.g., compressed, bit packed, etc.) exceeds data storage limitations of the target device following the processing. In a particular embodiment, the system may specify that medication administration events and vital observations collected for a patient have a higher priority than demographic information or general observation notes. By applying this prioritization, the system may rearrange the data within a record to be transmitted and/or stored, tailoring the compressed dataset to the storage size of a recipient target device. In this way, the system may ensure that the most important information is stored on, and/or transmitted to, a recipient device by tailoring the compression of the data based on structure, data type, and importance. The system may ensure that the important data is stored and/or transmitted first, and if any data is ultimately unable to fit in the allotted space, the prioritization will ensure that the data left off is less important data.

Exemplary Algorithm for Structured and Configurable Data Compression/Decompression HL7 messages, such as FHIR, may transmit computable medical data on a patient using a structure such as the example shown below in Table 1 for a set of vital signs on a patient. As can be seen, this structure may be complex and may use multiple levels of nesting to establish a hierarchy of information to describe and transmit a patient's vital signs, such as respiratory rate, heart rate, blood pressure, and body temperature.

TABLE 1

Example HL7 Message Structure

```
{
  "resourceType": "Observation",
  "id": "vitals-panel"
  "meta": {
    "profile": [
       "http://hl7.org/fhir/StructureDefinition/vitalsigns"
    ]
  },
  "text": {
    "status": "generated",
    "div": "<div xmlns=\"http://www.w3.org/1999/xhtml\"><p><b>Generated Narrative with Details</b></p><p><b>id</b>: vitals-panel</p><p><b>meta</b>: </p><p><b>status</b>: final</p><p><b>category</b>: Vital Signs <span>(Details : {http://terminology.hl7.org/CodeSystem/observation-category code 'vital-signs' = 'Vital Signs', given as 'Vital Signs'})</span></p><p><b>code</b>: Vital signs Panel <span>(Details : {LOINC code '85353-1' - 'Vital signs, weight, height, head circumference, oxygen saturation & BMI panel', given as 'Vital signs, weight, height, head circumference, oxygen saturation and BMI panel'})</span><p><p><b>subject</b>: <a>Patient/example </a></p><p><b>effective</b>: 02/07/1999</p><p><b>hasMember</b>: </p><ul><li><a>Respiratory Rate</a></li><li><a>Heart Rate</a></li><li><a>Blood Pressure </a></li><li><a>Body Temperature</a></li></ul></div>"
  },
  "status": "final",
  "category": [
    {
      "coding", [
        {
          "system": "http://terminology.hl7.org/CodeSystem/observation-category",
          "code": "vital-signs",
          "display": "Vital Signs"
        }
      ],
      "text": "Vital Signs"
    }
  ],
  "code": {
    "coding": [
```

TABLE 1-continued

Example HL7 Message Structure

```
            {
                "system": "http://loinc.org",
                "code": "85353-1",
                "display": "Vital signs, weight, height, head circumference, oxygen saturation and BMI panel"
            }
        ],
        "text": "Vital signs Panel"
    },
    "subject": {
      "reference": "Patient/example"
    },
    "efectiveDateTime" "1999-07-02",
    "hasMember": [
        {
            "reference": "Observation/respiratory-rate",
            "display": "Respiratory Rate"
        },
        {
            "reference": "Observation/heart-rate",
            "display": "Heart Rate"
        },
        {
            "reference": "Observation/blood-pressure",
            "display": "Blood Pressure"
        },
        {
            "reference": "Observation/body-temperature",
            "display": "Body Temperature"
        }
    ]
}
```

Values used in a message structure such as that shown in Table 1 may be encoded as shown in the example provided in Table 2 below. In this example, a single body temperature observation of 36.5 C is represented using coded terminology sets to define that the measure is body temperature (LOINC Code 8310-5) and the unit of measure of the temperature value is in Celsius. In addition, the time of the observation is encoded.

TABLE 2

Example Value Encoding

```
{
  "resourceType": "Observation",
  "id": "body-temperature"
  "meta": {
    "profile": [
       "http://hl7.org/fhir/StructureDefinition/vitalsigns"
    ]
  },
  "text": {
    "status": "generated",
        "div": "<div xmlns=\"http://www.w3.org/1999/xhtml\"><p><b>Generated Narrative with Details</b></p><p><b>id</b>: body-temperature</p><p><b>meta</b>: </p><p><b>status</b>: final</p><p><b>category</b>: Vital Signs <span>(Details : {http://terminology.hl7.org/CodeSystem/observation-category code 'vital-signs' = 'Vital Signs', given as 'Vital Signs'))</span></p><p><b>code</b>: Body temperature <span>(Details : {LOINC code '8310-5' - 'Body temperature', given as 'Body temperature'})c/span></p><p><b>subject</b>: <a>Patient/example</a></p><p><b>effective</b>: 02/07/1999</p><p><b>value</b>: 36.5 C<span>(Details: UCUM code Cel = 'Cel')</span></p></div>"
  },
  "status": "final",
  "category": [
    {
      "coding", [
        {
          "system": "http://terminology.hl7.org/CodeSystem/observation-category",
          "code": "vital-signs",
          "display": "vital Signs"
        }
      ],
      "text": "Vital Signs"
    }
  ],
  "code": {
```

TABLE 2-continued

Example Value Encoding

```
    "coding": [
      {
        "system": "http://loinc.org",
        "code": "8310-5",
        "display": "Body temperature"
      }
    ],
    "text": "Body temperature"
  },
  "subject": {
    "reference": "Patient/example"
  },
  "efectiveDateTime" "1999-07-02",
  "valueQuantity": {
    "value": 36.5,
    "unit": "C",
    "system": "http://unitsofmeasure.org":
    "code": "Cel"
  }
}
```

In various embodiments, the system may reduce the repetitiveness and nested structure of a record storing such information, as well as reduce the size of representations of coded values. Rather than representing a coded value using a lengthy code (e.g., the LOINC value 8310-5 seen in the tables above), the system may perform byte level encoding using the following structure and representation of that value within a record to compress the data, as shown in the example of Table 3.

TABLE 3

Example Byte Level Value Encoding

```
"code": {
  "coding": [
    {
      "system": "http://loinc.org",
      "code": "8310-5",
      "display": "Body temperature"
    }
  ],
  "text": "Body temperature"
},
```

The system may use one or more look-up tables for encoding. Such look-up tables may be updated, amended, and expanded as needed. Look-up tables may be domain-specific (e.g., specific to lab values, vital signs, medications, procedures, units of measure, etc.) and may contain the information such as coding system, code value, and display. Look-up tables may include one or more "byte values" that may each be a special character that is unique to the code the system is encoding and to the associated domain, as shown in the following example look-up of Table 4.

TABLE 4

Example Encoding Look-up Table

| Code System | Code Value | Display Text | Encoding Byte |
|---|---|---|---|
| http://loinc.org | 8310-5 | Body Temperature | 126 (~) |

By using a table for vital observations as shown in Table 4 above, the system may encode a body temperature code value using an encoding byte value of 126. Thus, the system may represent a structural encoded body temperature as a single byte of data. In this example, the value for the body temperature may be represented in binary at the $126^{th}$ byte. Because the system is using an encoding table specific to vitals and a byte, it will not be limited to only 256 bytes because the system may use both context (vital) and an encoding byte (126) to enable the encoding of 256 unique vital entries according to the table and for use in the disclosed embodiments. If even more values are needed, the system may use a secondary encoding byte that would provide, for example, 256×256 (65,536) encoding byte pair combinations for use in representing values for any domain type.

By using an encoding byte, the system may reduce the size of a substructure such as that shown in the example for body temperature, for example, from 195 bytes to one byte. By using this approach for mapping, compressing, and ultimately encoding data for all of various domains of data, the system may achieve the same or better compression in representing each of the coded values for a variety of types of data as a single byte. The system may use a known order of bytes in the structure of a message to ensure that the context of each segment of such a message is known and thereby enable the use of look-up tables to determine the information represented by the segments of the message. For example, the system may determine the value for the body temperature in binary and store and/or transmit that binary value as the $126^{th}$ byte of the record generated using the look up table of Table 4. That body temperature value is associated with the LOINC code value 8310-5 and the display text "Body Temperature." By using a similar look up table at a receiving device, the receiving device can readily determine the $126^{th}$ byte of the received record is a binary representation of body temperature associated with the LOINC code value 8310-5 and the display text "Body Temperature."

In various embodiments, the system may use a data structure similar to that of HL7 2.x formats for encapsulating patient records and to take advantage of the disclosed encoding and context-aware compression methods. Note that the example data structures and record configurations described herein are meant to be representative and other structures and implementations may be used without departing from the scope of this disclosure. The following example shown in Table 5 is an example of a generic data structure according to various embodiments that does not necessarily take into account any specific target but rather illustrates a general approach to structuring data at the byte level to achieve the compression goals described.

In a particular embodiment, the system structures a patient record based on a patient that has one or more encounters (e.g., visits or interactions with a care provider). In this example, a Tactical Combat Casualty Care (TCCC) card may be used to record traumatic injuries incurred in the battlefield. Each encounter may result in numerous patient vital observations, medications dispensed, procedures performed, and injuries noted that the system may record on the TCCC card. In the operational medicine environment, each such encounter record may represent a role of care from when a patient is wounded and first treated in a DIL environment, through transport where DIL conditions may or may not be present, and ultimately back to a hospital where DIL conditions are no longer be applicable. Table 5 illustrates the layout of an example of such a record.

TABLE 5

Example Encounter Record (1-1)Demographics - First, Last, Gender, Rank, Branch, IDNum
(1..N) Encounter -Timestamp
   (1..N) Vital
      Vital Code, Vital Unit Code, Vital Measurement, Timestamp
   (1..N) Medication
      Medication Code, Dispensed Value, Dispensed Unit, TimeStamp Offset
   (1..N) Injury
      Injury Code, Location Code, TimeStamp Offset
   (1..N) Procedure
      Procedure Code, Location Code, Timestamp Offset In the example record of Table 5, the record may include a structure for patient demographics followed by a structure for a particular encounter that occupies a predefined number of bytes (e.g., 1-N bytes). Within the encounter structure, a first particular set of bytes may be a substructure of a particular number of bytes that represents vital signs, where the order of the bytes indicates the particular vital sign data (e.g., the first byte of the substructure is the vital code, the second byte of the substructure is the vital unit code, the third byte of the substructure is the vital measurement, etc.). After the vital signs substructure, the next substructure may be a particular set of bytes that represents medications, where the order of the bytes indicates the particular medication data (e.g., the first byte of the substructure is the medication code, the second byte of the substructure is the dispensed value, the third byte of the substructure is the dispensed unit, etc.). By using a look up table as described above, the information in a record, such as the exemplary record of Table 5, may be encoded and stored in a minimal amount of space and transmitted using a minimal amount of resources.

Structured and Configurable Data Compression/Encoding Module

Figure 9:
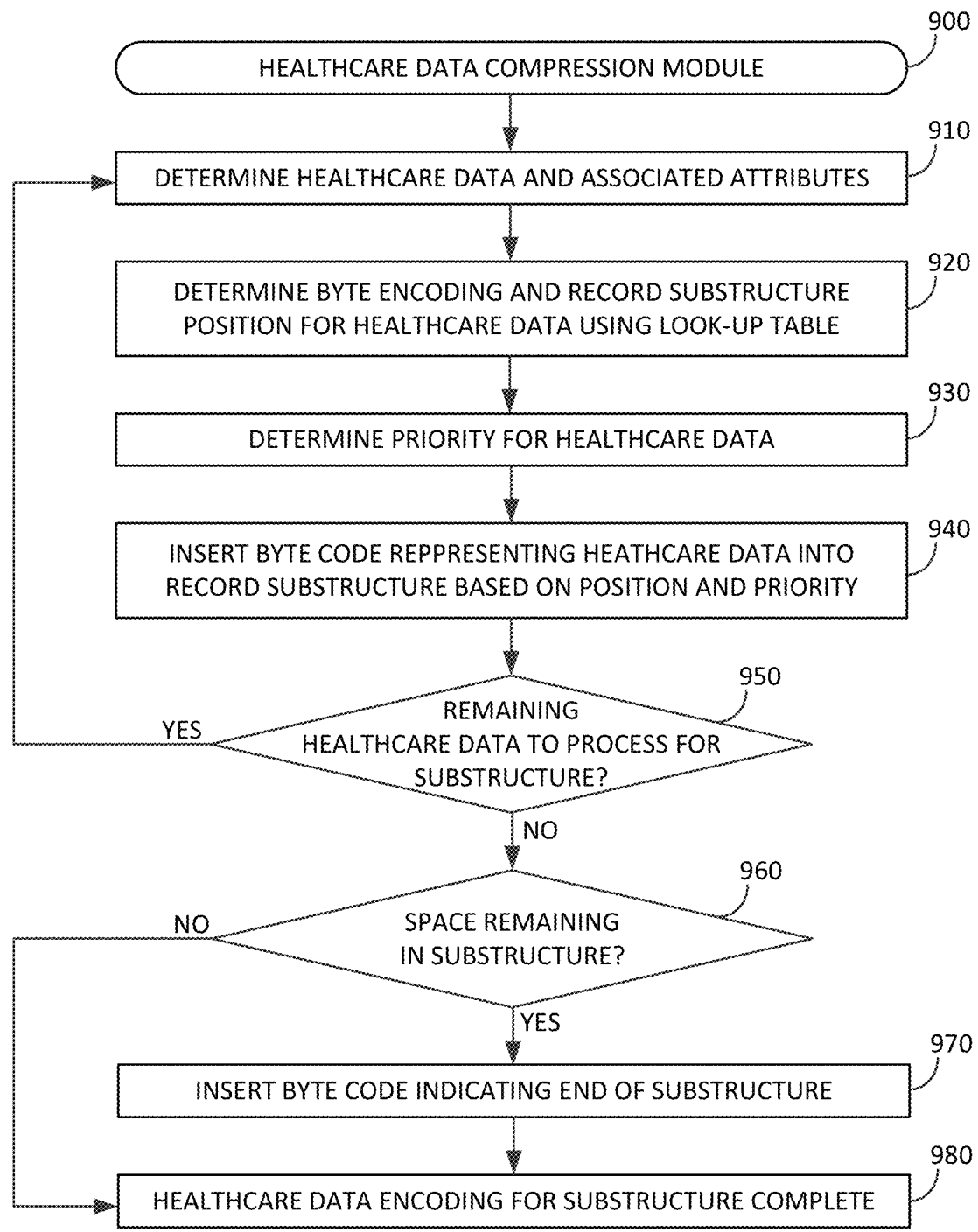
FIG. 9 is a flow chart showing an example of a process performed by a Healthcare Data Compression Module according to various embodiments.

FIG. 9 illustrates an example process that may be performed by a Healthcare Data Compression Module 900 according to the disclosed embodiments. In executing the Healthcare Data Compression Module 900, the system begins at Step 910 where a particular piece of healthcare data may be determined, for example, as entered by a healthcare provider on a mobile device as health measurements are taken on a patient; received as a portion of a transmission of healthcare data, etc. The system may determine attributes of the particular piece of healthcare data at Step 910 that, for example, that may be used to determine the byte-level encoding for the particular piece of healthcare data. For example, the system may determine the numeric value (e.g., represented by characters in s string) of a body temperature along with the associated attributes of the LOINC code value 8310-5 and the display text "Body Temperature."

At Step 920, the system may determine the byte encoding for the particular piece of healthcare data using a look-up table. In a particular embodiment, using the particular piece of healthcare data and, in some embodiments, one or more associated attributes, the system may determine the particular position of the byte to be used to represent the particular piece of healthcare data using a look-up table such as that shown in Table 4. The system may also determine a manner and/or type of encoding (e.g., as a binary value representing the particular piece of healthcare data, as a special byte code designator, etc.). In this particular example, the system may determine that, for the particular piece of healthcare data that is a body temperature with the LOINC code value 8310-5, the position of a byte within the vital signs substructure representing this body temperature in a the $126^{th}$ byte. The look-up table may also specify that the body temperature is to be stored as a binary value representing the body temperature in the $126^{th}$ byte of the appropriate substructure. The look-up table may also, or instead, include any other information that the system may use to map one or more bytes to a piece of healthcare data. Such mapping may take any suitable form, including, by not limited to a position of a byte in a structure, substructure, and/or record associated with a particular type of healthcare data. The look-up table may also, or instead, include any other information that the system may use to specify how the piece of healthcare data is to be encoded in one or more bytes (e.g., an indicator instructing the system to encode the piece of healthcare data as a binary value representing the particular piece of healthcare data, as a special byte code designator, etc.).

At Step 930, the system may determine a priority of the particular piece of healthcare data. As described above, in particular embodiments, where there may be storage limitations to the amount of data that can be stored or transmitted, the system may determine that some information is more important than other information, and may be configured to insert information of greater importance into a stream of encoded information earlier than information that is of lesser importance.

At Step 940, the system may insert (e.g., store, transmit, etc.) the determined byte code for the particular piece of healthcare data into the structure, substructure, and/or record currently being processed (e.g., encoded, compressed) based on the position determined from the look-up table and/or the priority associated with the particular piece of healthcare data.

At Step 950, the system may determine whether there remains any further healthcare data to be processed (compressed, encoded, transmitted, stored, etc.). If there is remaining healthcare data to be processed, the system may return to Step 910 to resume such processing.

If the system determines, at Step 950, that there is no further healthcare data to process, then at Step 960 the system may determine if there is unused space remaining in the sequence of encoded bytes allotted to the sections of healthcare data associated with the healthcare data currently being processed (e.g., remaining space in the associated structure, substructure, record, etc.). If there is remaining space in the particular sequence of encoded bytes associated with the healthcare data being processed, at Step 970 the system may insert a special byte code indicating that the particular sequence of encoded bytes is complete, thereby allowing the system to begin encoding the next sequence of encoded bytes directly after the special byte code, using space that would otherwise have gone unused. This particular special byte code may also serve as indicator to the device receiving or reading the particular sequence of encoded bytes that this particular sequence of encoded bytes is complete.

At Step 980, after processing the particular healthcare data (and, in particular embodiments, after inserting a special byte code indicating the end of this particular sequence of encoded bytes), the processing of the healthcare data is complete. The system may then process other healthcare data, store the encoded healthcare data, transmit the encoded healthcare data, or perform any other suitable functions using the healthcare data.

Structured and Configurable Data Decompression/Decoding Module

Figure 10:
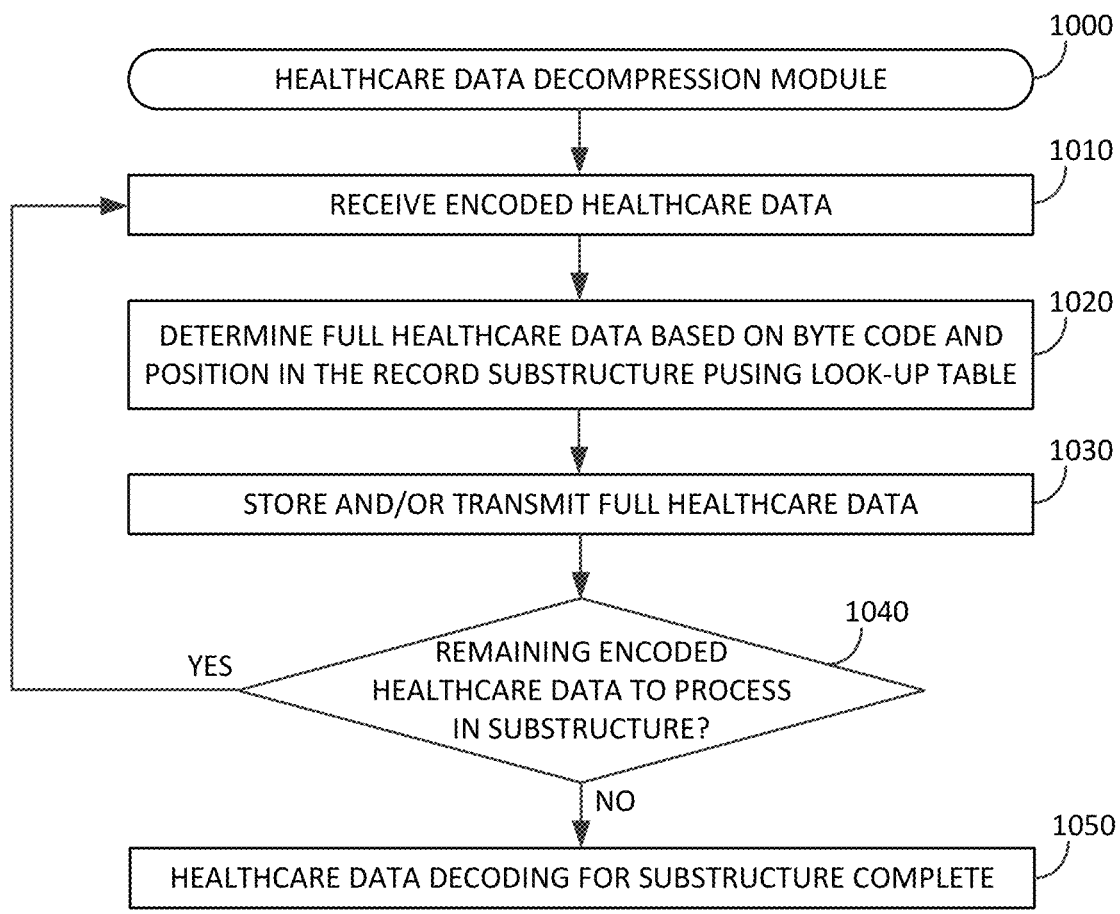
FIG. 10 is a flow chart showing an example of a process performed by a Healthcare Data Decompression Module according to various embodiments.

FIG. 10 illustrates an example process that may be performed by a Healthcare Data Decompression Module 1000 according to the disclosed embodiments. In executing the Healthcare Data Decompression Module 1000, the system begins at Step 1010 by receiving encoded healthcare data, such as a sequence of encoded bytes associated with, for example, a particular type of healthcare data (e.g., a structure, substructure, record, etc.). The system may receive a full sequence of healthcare data encoded bytes for processing or may receive and process individual encoded bytes.

At Step 1020, the system may determine the full health data for a particular encoded byte using a look-up table, such as look-up Table 4 above. In various embodiments, the system may use the look-up table to determine attributes of the particular piece of healthcare data associated with the particular encoded byte by locating the entry in the encoding table associated with the position of the particular encoded byte in its associated particular sequence of encoded bytes. The system may then use this look-up table entry to determine the attributes of the particular piece of healthcare data associated with the particular encoded byte as well as any information that may be used to return the particular encoded byte to its decoded form. For example, the entry associated with the particular encoded byte in the look-up table may indicate that the numeric value contained in the particular encoded byte as a binary value should be represented as a string of characters when decoded. In the particular example illustrated in Table 4, the system may determine that the particular encoded byte in the 126$^{th}$ position of this particular sequence of encoded bytes is associated with a particular piece of healthcare data that is a body temperature having the LOINC code value 8310-5. The look-up table may also specify that the body temperature, as decoded, is to be stored as a numeric value represented by a string of characters. The look-up table may also, or instead, include any other information that the system may use to map one or more encoded bytes to a particular full (e.g., decoded) healthcare record.

At Step 1030, the system may store, transmit, and/or perform any other processing on the decoded particular piece of healthcare data derived from the particular encoded byte. At Step 1040, the system may determine if there are any remaining encoded bytes in this particular sequence of encoded bytes to be processed. If so, the system may return to Step 1010 to continue processing (e.g., decoding, decompressing) the encoded bytes in this particular sequence of encoded bytes. If there are not further encoded bytes in this particular sequence of encoded bytes, at Step 1050 the processing of this particular sequence of encoded bytes may be complete.

As one skilled in the art will recognize, the examples described herein in regard to the specific use, compression, encoding, processing, and transmittal of medical information, including the use of value encoding tables, structured records, bit packing, and prioritization of data, may be applied to any structured dataset across any industry type where information exchange may be performed. Examples of such implementations according to the disclosed embodiments include, but are not limited to, transmittal of hardware data, service records, capturing and tracking audit log information, machine maintenance records, real-time telemetry data, etc. The disclosed embodiments are not limited to any particular device or transmission method.

Structured and Configurable Data Compression Using QR Codes

In various embodiments, the system may generate one or more QR codes that each represent a portion of data compressed and/or represented in one or more structured data records as described herein. These QR codes may then be presented to another device (e.g., mobile device) in order to transmit the encoded data to that device. The receiving device may use a camera or one or more other digital image capture components to capture images of the QR codes and decode them to reconstruct the data represented by the code. Any of the data described herein may be communicated using QR codes as set forth below.

In various embodiments, the system may separate a dataset into sequential portions, each having a size that may be represented by a single QR code. In particular embodiments, the system may leave space within any one particular QR code to include a sequence position indicator (e.g., a code or identifier) that indicates the position of the data represented in the particular QR code within the dataset. The system may also account for error correction data that may be included or represented in the QR code. The sequence position indicator may also indicate a total number of QR codes used to represent the entire dataset. For example, if a dataset is broken down into six portions, each of which may be represented in a single QR code along with a sequence position indicator, the first portion of the dataset may be represented by a QR code that includes a (e.g., encoded) sequence position indicator of "1/6," indicating that this is the first of six QR codes used to represent the dataset. The QR code representing the immediate subsequent portion of the dataset may have a sequence position indicator of "2/6," the QR code representing the portion of the dataset immediately following may have a sequence position indicator of "3/6," and so on. The QR code representing the final portion of the dataset may have a sequence position indicator of "6/6," which a decoding system may use to identify the decoded data associated with that QR code as the final portion of the dataset.

In various embodiments, a series of QR codes representing a complete dataset may be presented for capture by a system using one image. For example, several QR codes, each representing a portion of a dataset, may be printed onto a single piece of paper or displayed on a display device (e.g., screen of a computer or mobile device). A recipient device may capture an image of the several QR codes and decode each of them to determine the represented data and the sequence positions indicator for each QR code. The recipient device may then reassemble the encoded dataset using the sequence position indicators to determine the proper location of each portion of decoded data within the dataset.

In various embodiments, a larger dataset may require the use of more QR codes than can be readably presented on one screen or captured in one image. For example, there may be a limit to the number of QR codes (e.g., nine QR codes) that can be presented on a single mobile device display and still remain resolvable enough to decode due to limitations in display resolution. In such embodiments, the system may generate multiple images of multiple QR codes to create a QR code "movie." Each frame of such a movie may include one or more QR codes that can be decoded by a recipient device. In such an embodiment, the system may generate and use sequence position indicators as described above to ensure that the encoded dataset can be properly reconstructed.

In various embodiments, for example where a relatively small dataset is to be encoded, the system may use a single QR code to represent the entire dataset. In such embodiments, the system may still use a sequence position indicator that indicates that the QR code represents both the first and last portion of the dataset (e.g., "1/1").

Figure 11:
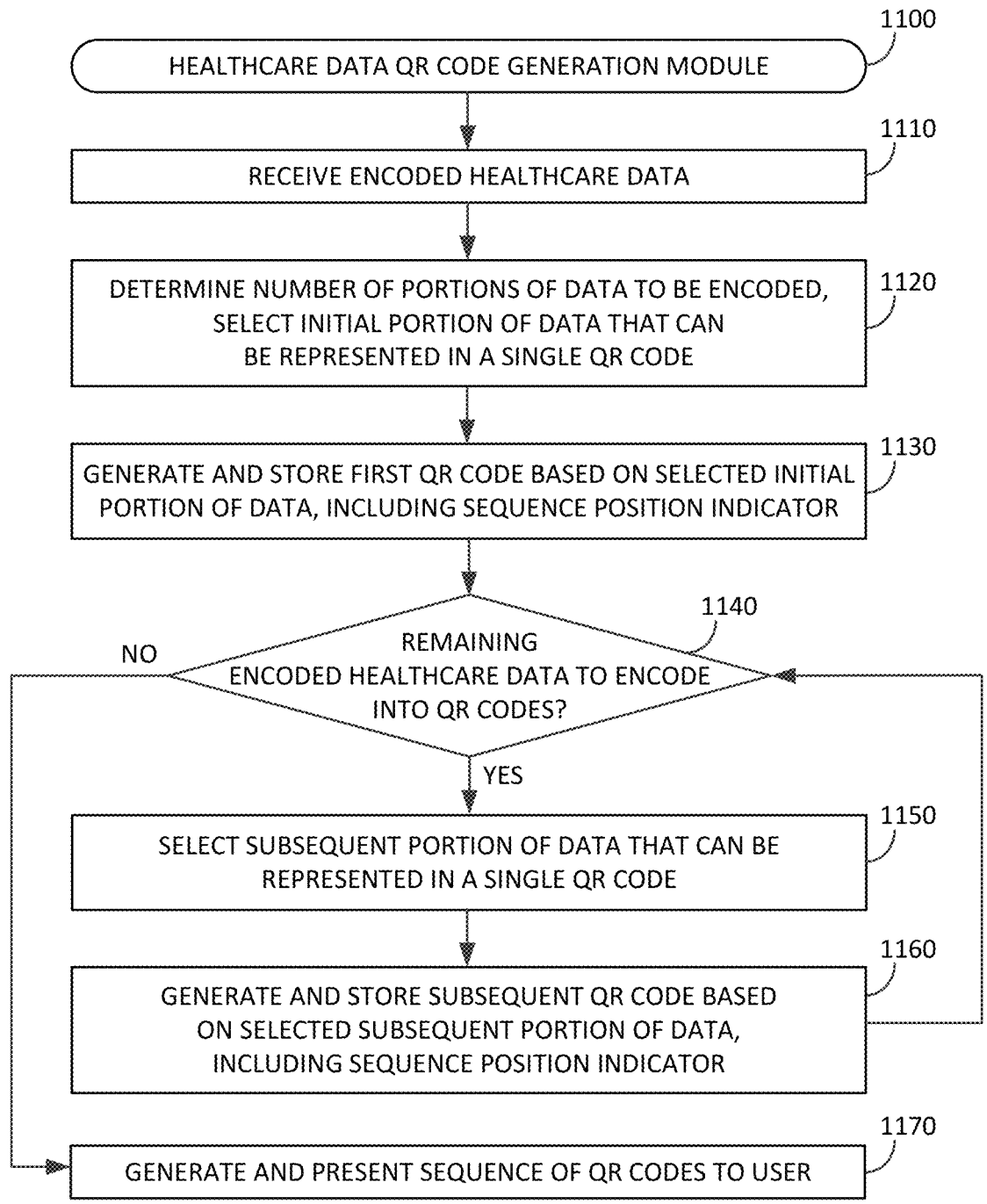
FIG. 11 is a flow chart showing an example of a process performed by a Healthcare Data QR Code Generation Module according to various embodiments.

FIG. 11 illustrates an example process that may be performed by a Healthcare Data QR Code Generation Module 1100 according to the various embodiments. In executing the module, the system may begin at Step 1110 by receiving a dataset to be encoded. This dataset may include data that has been encoded in any manner as described herein.

At Step 1120 the system may break the dataset into one or more portions, each of which is of a size that may be represented by a single QR code, in particular embodiments allowing for the inclusion of a sequence position indicator. In particular embodiments, the system may be configured to break the dataset into 1100-byte portions to ensure that each portion, and its associated sequence position indicator, may be represented in a QR code. In other embodiments, the system may be configured to break the dataset into portions of 2000 bytes, minus the number of bytes used by a sequence position indicator. Other sizes of portions of datasets may be used and may be selected based on various criteria, such as anticipated display, printer, and/or camera resolution, etc. Further at Step 1120, the system may select an initial portion of the dataset for encoding in the first QR code.

At Step 1130, the system may generate the QR code representing the first portion of the dataset and including the sequence position indicator for the first portion (e.g., "1/X" of a dataset broken into X portions).

At Step 1140, the system may determine if there are any portions of the dataset remaining to be encoded into QR codes. If not, the process may move to Step 1170 where the system may generate and present the sequence of one or more QR codes representing the dataset to a user. This may be accomplished by printing the sequence of one or more QR codes onto paper and/or presenting images of the QR code(s) on a display.

If there are remaining portions of the dataset to be encoded, at Step 1150, the system may select a subsequent unencoded portion and generate, at Step 1160, a QR code representing that portion of the dataset and including a sequence position indicator for the that portion. Then the process may return to Step 1140 to determine whether there are any other portions of the dataset remining to be encoded. If so, Steps 1150 and 1160 may be repeated as necessary until the entire dataset has been encoded onto QR codes. As mentioned, once all portions of the dataset have been encoded as QR codes, the process may move to Step 1170 where the system may generate and present the sequence of one or more QR codes representing the dataset to a user (e.g., by printing or displaying the sequence of one or more QR codes). In particular embodiments, a single group of QR codes (e.g., 1-9 codes) may be presented on a display (e.g., mobile device display, computer display) or printed on a piece of paper or a sticker. Alternatively, a series of images (e.g., equivalent to a series of video frames) may be generated that each have one or more QR represented therein.

Figure 12:
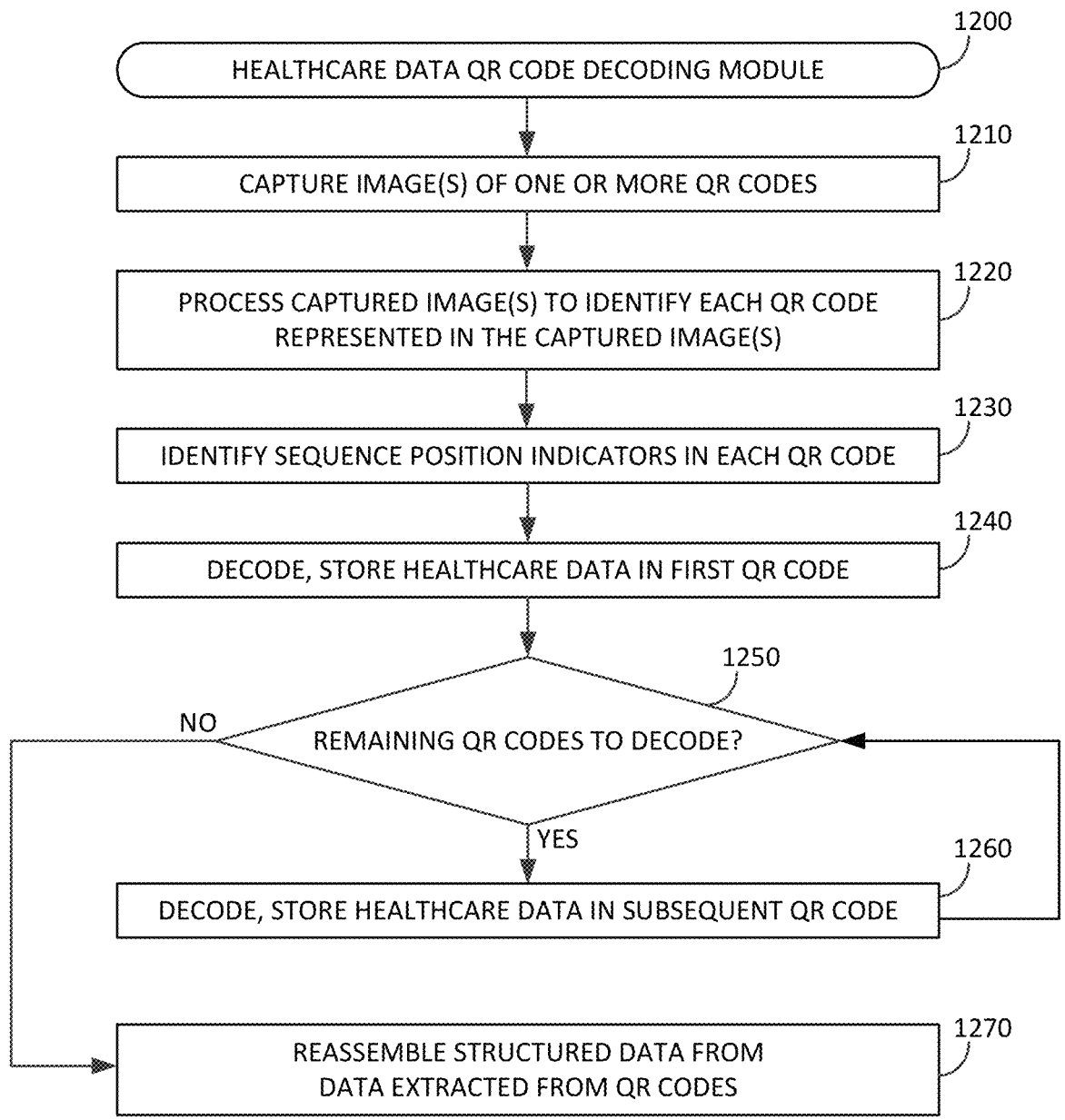
FIG. 12 is a flow chart showing an example of a process performed by a Healthcare Data QR Code Decoding Module according to various embodiments.

FIG. 12 illustrates an example process that may be performed by a Healthcare Data QR Code Decoding Module 1200 according to the various embodiments. In executing the module, the system may begin at Step 1210 by capturing one or more images that each may include one or more QR codes. At Step 1220, the system may process the captured one or more images or identify each individual QR represented in each image. Once each QR code has been identified, at Step 1230 the system may identify the sequence position indicator represented in each QR code. The system may store or otherwise retain this indicator for use in reconstructing the dataset represented by the one or more QR codes.

At Step 1240, the system may decode the data represented in the QR code associated with the first sequence position indicator and store that data. At Step 1250, the system may determine whether there are any other QR codes with data related to the dataset associated with the first QR code. For example, the system may analyze the sequence position indicator to determine whether there are other portions of data remaining (e.g., "1/1" indicates there is only one QR code for this dataset). If there are additional dataset portion represented by further QR codes, the process may move to Step 1260 to decode and store the data represented in a subsequent QR code. After decoding that QR code, the system may return to Step 1250 to determine whether there are any other codes remaining for the dataset. These steps may be repeated until all the codes for a particular dataset have been identified and decoded.

When the system determines that all the QR codes for a particular dataset have been decoded, the process may move to Step 1270 where the dataset may be reconstructed using the decoded data portions and the associated sequence position indicators for each such portion. Note that in various embodiments, the system may reassemble the dataset portions as they are decoded rather than decoding all the portions and then reassembling the dataset. Note also that in various embodiments, the system may decode all detected QR codes in any order, regardless of the associated sequence position indicators, and then reassemble the dataset. Variations on the order of processing, encoding, decoding, and/or reassembling datasets are contemplated as within the scope of this disclosure.

Figure 13:
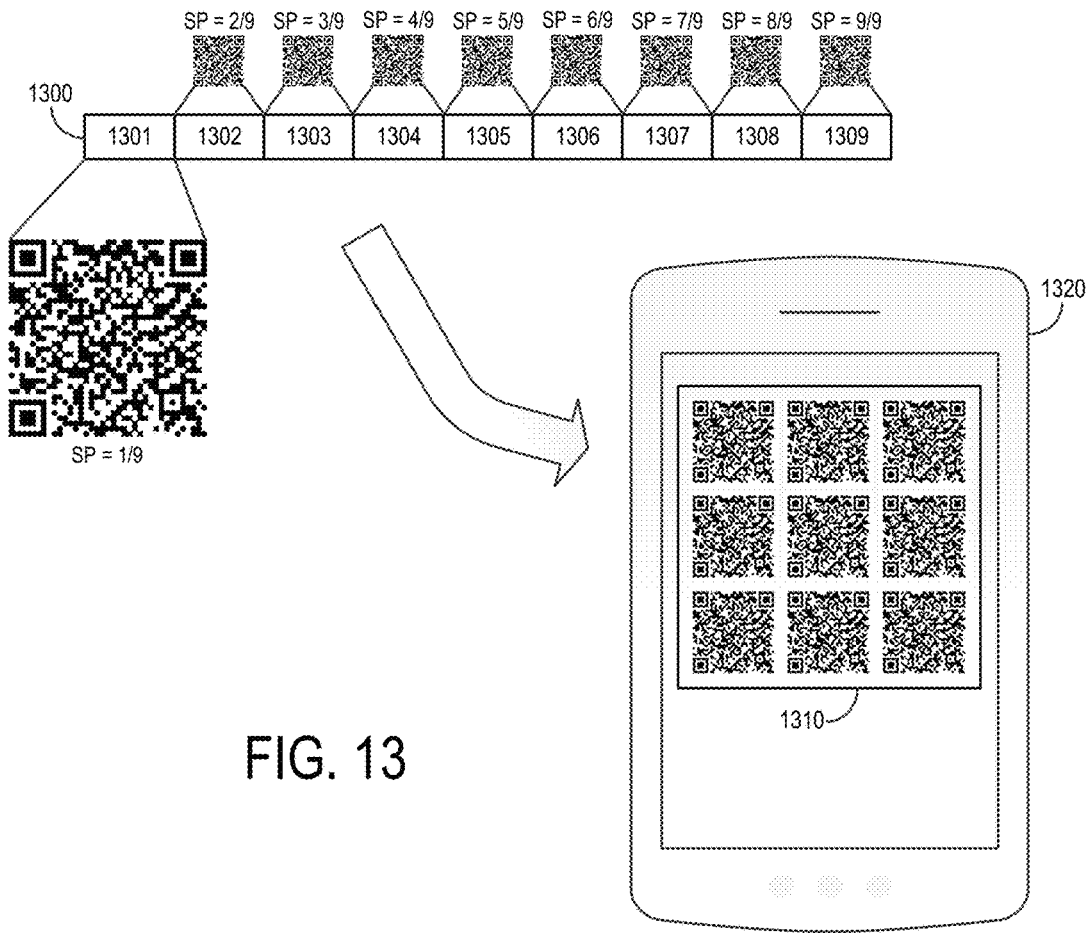
FIG. 13 illustrates exemplary healthcare data encoded as a sequence of QR codes according to various embodiments.

FIG. 13 illustrates a graphical representation of an exemplary dataset 1300 and presentation thereof. The system may separate the dataset 1300 into subsets 1301-1309 of the dataset 1300, each of which may be of a particular size (e.g., 1100 bytes, 2000 bytes, etc.) that is conducive to representation by a single QR code. In various embodiments, the size of each of the dataset subsets 1301-1309 may be determined based on including a sequence position indicator.

As shown in FIG. 13, each dataset subset may include a sequence position indicator that indicates both the assigned position of that subset and the total number of subsets. For example, the first subset 1301 of a nine-subset dataset may have a sequence position indicator of "1/9,", the second subset 1302 may have a sequence position indicator of "2/9," and so on, with the final subset 1309 having a sequence position indicator of "9/9." In decoding multiple QR codes associated with a particular dataset, the system may determine that it is processing the final QR code by determining that the position value for the QR code is equal to the value for the total number of subsets.

Once the QR codes are generated, they may be presented in groups within an image. For example, the group 1310 of QR codes may include each QR code generated for the subsets of the dataset 1300. The group of QR codes may be printed on paper and/or a sticker, and/or may be presented on a device display, such as the display of mobile device 1320 shown in FIG. 13. In particular embodiments, the system may be configured to limit a total number of QR codes presented in a single image based on the resolution of the displaying device and/or of the capturing device's camera. For example, the system may configure no more than six or nine QR codes in a single image to be presented on a device display.

Figure 14:
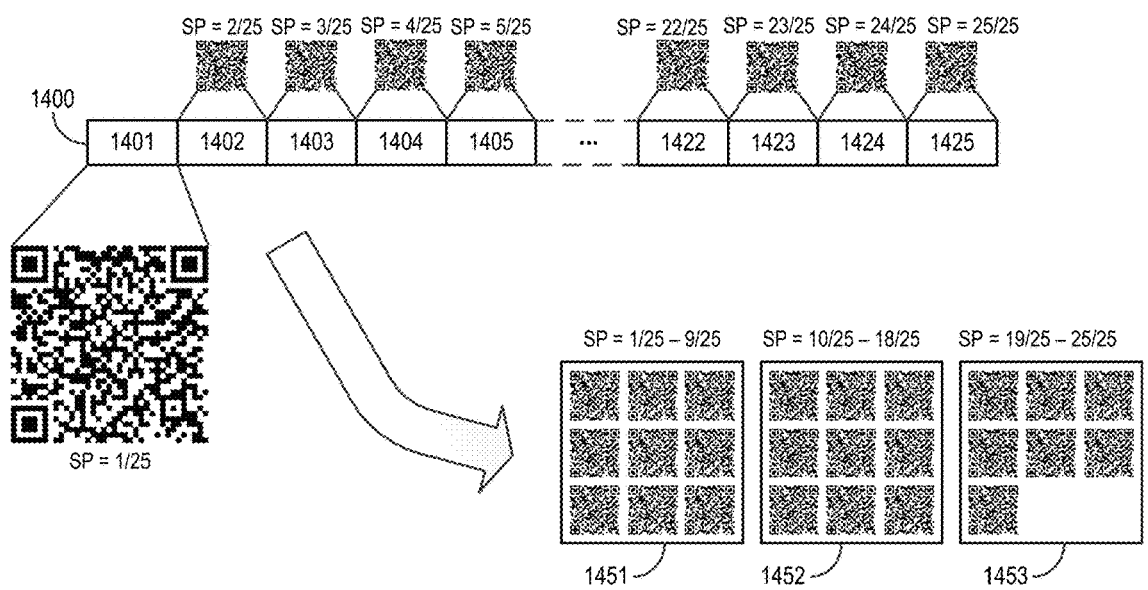
FIG. 14 illustrates exemplary healthcare data encoded as a sequence of QR codes presented in a sequence of video frames according to various embodiments.

In various embodiments, the system may process a dataset that requires more QR code for representation that may be recognizably displayed in a single image. In such embodiments, the system may generate multiple images have one or more QR codes each, similar to multiple frames in video content. FIG. 14 illustrates a graphical representation of an exemplary dataset 1400 and presentation thereof according to such an embodiment. The system may separate the dataset 1400 into subsets 1401-1425 of the dataset 1400, each of which may be of a particular size (e.g., 1100 bytes, 2000 bytes, etc.) that is conducive to representation by a single QR code. Here again, in various embodiments, the size of each of the dataset subsets 1401-1425 may be determined based on the inclusion of a sequence position indicator.

As shown in FIG. 14, each dataset subset may include a sequence position indicator that indicates both the assigned position of that subset and the total number of subsets. For example, the first subset 1401 of a 25-subset dataset may have a sequence position indicator of "1/25,", the second subset 1402 may have a sequence position indicator of "2/25," and so on, with the final subset 1425 having a sequence position indicator of "25/25." In decoding the multiple QR codes associated with the dataset 1400, the system may determine that it is processing the final QR code by determining that the position value for the QR code representing the subset 1425 ("25") is equal to the value for the total number of subsets ("25"), e.g., "25/25."

Once the QR codes are generated, they may be presented in groups within multiple images. In this embodiment, even with several QR codes in each group, the number of QR codes necessitates the use of several images due to the limited number of QR codes that can be included in any single image. For example, the group 1451 of QR codes may include the first nine QR codes generated for the dataset 1400, the group 1452 may include the next nine QR codes generated for the dataset 1400, and the group 1453 of QR codes may include the final seven QR codes generated for the dataset 1400. These groups of QR codes may be printed on one or more pieces of paper and/or one or more stickers. Alternatively, or in addition, these groups of QR codes may be presented (e.g., sequentially) as images on a device display. A recipient device may capture or receive such images as frames in video content process each frame to decide the QR codes represented therein, ultimately reassembling the dataset represented by the QR codes in the video frames.

CONCLUSION

Although embodiments above are described in reference to various data storage and exchange systems, it should be understood that various aspects of the system described above may be applicable to other types of systems, in general.

While this specification contains many specific embodiment details, these should not be construed as limitations on the scope of any invention or of what may be claimed, but rather as descriptions of features that may be specific to particular embodiments of particular inventions. Certain features that are described in this specification in the context of separate embodiments may also be implemented in combination in a single embodiment. Conversely, various features that are described in the context of a single embodiment may also be implemented in multiple embodiments separately or in any suitable sub-combination. Moreover, although features may be described above as acting in certain combinations and even initially claimed as such, one or more features from a claimed combination may in some cases be excised from the combination, and the claimed combination may be directed to a sub-combination or variation of a sub-combination.

Similarly, while operations may be described in a particular order, this should not be understood as requiring that such operations be performed in the particular order described or in sequential order, or that all described operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems may generally be integrated together in a single software product or packaged into multiple software products.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for the purposes of limitation.

What is claimed is:

1. A computer-implemented data processing method for encoding healthcare data, the method comprising:
    transmitting, by one or more near-field communications (NFC) components configured at an NFC initiator device, an NFC initiation signal to a recipient device, wherein the recipient device comprises a water-resistant flexible encapsulation portion configured to encapsulate a plurality of electronic components;
    establishing, by one or more computer processors configured at the NFC initiator device, using the one or more NFC components configured at the NFC initiator device, an NFC field with the recipient device;
    receiving, by the one or more NFC components configured at the NFC initiator device, a data exchange message from the recipient device;
    determining, by the one or more computer processors configured at the NFC initiator device, based at least in part on the data exchange message, a BLUETOOTH address for the recipient device;
    establishing, by one or more BLUETOOTH components configured at the NFC initiator device, a BLU- ETOOTH bond with the recipient device using the BLUETOOTH address for the recipient device;

receiving, by the one or more computer processors configured at the NFC initiator device, healthcare data comprising a plurality of pieces of healthcare data;

compressing, by the one or more computer processors configured at the NFC initiator device, the healthcare data by:
  determining a value of a first piece of healthcare data of the plurality of pieces of healthcare data;
  determining one or more attributes of the first piece of healthcare data;
  determining, using a look-up table, a byte position for the first piece of healthcare data based on the one or more attributes of the first piece of healthcare data;
  determining, using the look-up table, an encoding type for the first piece of healthcare data based on the one or more attributes of the first piece of healthcare data;
  generating, based on the encoding type for the first piece of healthcare data, an encoded byte representing the first piece of healthcare data;
  inserting the encoded byte representing the first piece of healthcare data into a sequence of encoded bytes at the byte position for the first piece of healthcare data; and
  generating a dataset comprising the sequence of encoded bytes;

separating, by the one or more computer processors configured at the NFC initiator device, the dataset into a plurality of subsets of the dataset;

determining, by the one or more computer processors configured at the NFC initiator device, a sequence position for each subset of the plurality of subsets based on a position within the dataset of each respective subset of the plurality of subsets;

generating, by the one or more computer processors configured at the NFC initiator device, a respective quick response (QR) code for each subset of the plurality of subsets, wherein each respective QR code comprises:
  a first visual indicator representing a respective subset of the plurality of subsets; and
  a second visual indicator representing a sequence position for the respective subset of the plurality of subsets; and presenting, by the one or more computer processors configured at the NFC initiator device, to a user, each respective QR code for each subset of the plurality of subsets.

2. The computer-implemented data processing method of claim 1, wherein the second visual indicator further represents a total quantity of subsets in the plurality of subsets.

3. The computer-implemented data processing method of claim 1, wherein separating the dataset into the plurality of subsets of the dataset comprises:
  determining a data capacity of a single QR code;
  determining a size of the dataset;
  determining that the size of the dataset exceeds the data capacity of the single QR code; and
  in response to determining that the size of the dataset exceeds the data capacity of the single QR code, separating the dataset into the plurality of subsets of the dataset.

4. The computer-implemented data processing method of claim 3, wherein determining the data capacity of the single QR code comprises:
  determining a size of a visual indicator representing a sequence position for a subset of the plurality of subsets; and
  determining the data capacity of the single QR code based at least in part on the size of the visual indicator representing the sequence position for the subset of the plurality of subsets.

5. The computer-implemented data processing method of claim 1, wherein each subset of the plurality of subsets has a maximum size of about 1100 bytes.

6. The computer-implemented data processing method of claim 1, wherein presenting the QR code for each subset of the plurality of subsets to the user comprises displaying the QR code for each subset of the plurality of subsets on a display of the NFC initiator device.

7. The computer-implemented data processing method of claim 1, wherein presenting the QR code for each subset of the plurality of subsets to the user comprises printing the QR code for each subset of the plurality of subsets onto one or more stickers.

8. A non-transitory computer-readable medium comprising computer executable instructions for processing data, the computer executable instructions comprising instructions for:
  transmitting, by one or more communications components configured at an initiator device, an initiation signal to a recipient device, wherein the recipient device comprises a data collection device comprising a flexible encapsulation portion configured to encapsulate a plurality of electronic components;
  establishing, by one or more computer processors configured at the initiator device, using the one or more communications components, a communications session with the recipient device;
  transmitting, from the one or more communications components to the recipient device, a request for data collected by the recipient device;
  receiving, by the one or more communications components from the recipient device, the data collected by the recipient device, the data comprising a plurality of pieces of healthcare data;
  compressing, by the one or more computer processors configured at the initiator device, the data by:
    determining a first piece of data of the plurality of pieces of data;
    determining one or more attributes of the first piece of data;
    determining, using a look-up table and based on the one or more attributes of the first piece of data, a byte position for the first piece of data;
    determining, using the look-up table and based on the one or more attributes of the first piece of data, an encoding type for the first piece of data;
    generating, based on the encoding type for the first piece of data, an encoded byte representing the first piece of data;
    inserting the encoded byte representing the first piece of data into a sequence of encoded bytes at the byte position for the first piece of data; and
    generating a dataset comprising the sequence of encoded bytes;
  identifying one or more subsets of the dataset;
  determining a sequence position indicator for each subset of the one or more subsets based on a position within the dataset of each respective subset of the one or more subsets;

generating a respective quick response (QR) code for each subset of the one or more subsets, wherein each respective QR code comprises:
a visual representation of the respective subset of the one or more subsets; and
a visual representation of a sequence position indicator for the respective subset of the one or more subsets; and
presenting each respective QR code for each subset of the one or more subsets to a user.

9. The non-transitory computer-readable medium of claim 8, wherein the data collected by the recipient device comprises sensor data collected from one or more sensors configured on a wearer of the recipient device.

10. The non-transitory computer-readable medium of claim 8, wherein:
the one or more communications components comprise one or more wireless communications components; and
establishing the communications session with the recipient device comprises establishing a wireless communications session with the recipient device.

11. The non-transitory computer-readable medium of claim 8, wherein:
the one or more communications components comprise one or more wired communications components; and
establishing the communications session with the recipient device comprises establishing a wired communications session with the recipient device.

12. The non-transitory computer-readable medium of claim 8, wherein presenting each respective QR code for each subset of the one or more subsets to the user comprises:
generating a plurality of display images, wherein each display image of the plurality of display images comprises one or more QR codes, and wherein each of the one or more QR codes is associated with a respective subset of the one or more subsets; and
sequentially presenting the plurality of display images on a display of the initiator device.

13. The non-transitory computer-readable medium of claim 8, wherein presenting each respective QR code for each subset of the one or more subsets to the user comprises:
generating a plurality of display images, wherein each display image of the plurality of display images comprises one or more QR codes, and wherein each of the one or more QR codes is associated with a respective subset of the one or more subsets; and
storing each display image of the plurality of display images as a video frame in video content data.

14. The non-transitory computer-readable medium of claim 8, wherein each respective QR code further comprises a visual representation of a total quantity of subsets of the one or more sub sets.

15. The non-transitory computer-readable medium of claim 14, wherein the total quantity of subsets of the one or more subsets equals the sequence position indicator.

16. A data processing system for decoding encoded data, the system comprising:
one or more processors;
one or more digital image capture components; and
computer memory storing computer-executable instructions that, when executed by the one or more processors, cause the one or more processors to perform operations comprising:
capturing, by the one or more digital image capture components, one or more images;
identifying, by the one or more processors, one or more quick response (QR) codes in each of the one or more images;
analyzing, by the one or more processors, each of the one or more QR codes to determine, for each respective QR code of the one or more QR codes:
a sequence position for a respective QR code; and
a subset of data represented by the respective QR code;
generating, by the one or more processors, a dataset comprising each subset of data represented by each of the one or more QR codes based at least in part on each respective sequence position for each of the one or more QR codes;
identifying, by the one or more processors, a sequence of encoded bytes within the dataset;
decompressing, by the one or more processors, the dataset by:
determining a first byte position within the sequence of encoded bytes for a first encoded byte of the sequence of encoded bytes;
determining, based on the first byte position within the sequence of encoded bytes for the first encoded byte, using a look-up table, one or more data attributes associated with a first piece of data;
determining, based on the one or more data attributes associated with the first piece of data, a decoding type for the first piece of data;
generating, based on the decoding type for the first piece of data, a value of the first piece of data using the first encoded byte;
storing, in the computer memory, the one or more data attributes associated with the first piece of data and the value of the first piece of data;
associating, in the computer memory, the one or more data attributes associated with the first piece of data and the value of the first piece of data;
generating a structured record comprising the one or more data attributes associated with the first piece of data and the value of the first piece of data;
determining a second byte position within the sequence of encoded bytes for a second encoded byte of the sequence of encoded bytes;
determining, based on the second byte position within the sequence of encoded bytes for the second encoded byte, using the look-up table, that the second encoded byte indicates the end of the structured record; and
storing the structured record in computer memory.

17. The data processing system of claim 16, wherein the sequence position for the respective QR code comprises:
a position of the subset of data within the dataset; and
a total quantity of subsets of data within the dataset.

18. The data processing system of claim 16, wherein capturing the one or more images comprises capturing a sequence of images presented as frames of video content.

19. The data processing system of claim 16, wherein each of the one or more images comprises a plurality of representations of QR codes.

20. The data processing system of claim 16, wherein one or more subsets of data within the dataset comprises healthcare data or sensor data.

* * * * *

UNITED STATES PATENT AND TRADEMARK OFFICE
CERTIFICATE OF CORRECTION

| | |
|---|---|
| PATENT NO. | : 11,177,027 B2 |
| APPLICATION NO. | : 17/316784 |
| DATED | : May 11, 2021 |
| INVENTOR(S) | : Joshua Michael Temkin et al. |

It is certified that error appears in the above-identified patent and that said Letters Patent is hereby corrected as shown below:

In the Specification

Column 1, Line 24, please add the following:
GOVERNMENT LICENSE RIGHTS
This invention was made with government support under W81XWH-19-C-0127, and W81XWH-20-C-0103 awarded by the Defense Health Agency, Medical Research and Development Branch. The government has certain rights in the invention.

Signed and Sealed this
Twenty-third Day of July, 2024

Katherine Kelly Vidal
*Director of the United States Patent and Trademark Office*